United States Patent [19]

Thompson et al.

[11] Patent Number: 5,691,323
[45] Date of Patent: *Nov. 25, 1997

[54] MUSCARINE ANTAGONISTS

[75] Inventors: Wayne J. Thompson, Lansdale; Michael F. Sugrue, Blue Bell; Richard W. Ransom, New Britian; Pierre J. Mallorga, Lansdale; Ian M. Bell, Harleysville; Anthony M. Smith, Green Lane, all of Pa.

[73] Assignee: Merck & Co., Inc., Rahway, N.J.

[*] Notice: The term of this patent shall not extend beyond the expiration date of Pat. No. 5,574,044.

[21] Appl. No.: 440,153

[22] Filed: May 12, 1995

[51] Int. Cl.$^6$ .......................... A61K 31/38; A61K 31/34; C07D 403/14; C07D 403/12

[52] U.S. Cl. .......................... 514/94; 514/253; 514/316; 514/322; 544/295; 544/243; 544/337; 544/364; 544/370; 546/187; 546/193; 546/199

[58] Field of Search .......................... 514/316, 322, 514/253, 94; 546/187, 193, 199; 544/295, 243, 337, 364, 370

[56] References Cited

U.S. PATENT DOCUMENTS

| | | | |
|---|---|---|---|
| 4,066,772 | 1/1978 | Vandenberk et al. | 424/267 |
| 4,076,821 | 2/1978 | Tsuda et al. | 424/263 |
| 4,329,353 | 5/1982 | Stokbroekx et al. | 424/267 |
| 4,397,853 | 8/1983 | Kawakita et al. | 424/250 |
| 4,398,030 | 8/1983 | Schmidt et al. | 548/506 |
| 4,970,217 | 11/1990 | Prücher et al. | 514/327 |
| 5,059,601 | 10/1991 | Salimbeni et al. | 514/255 |
| 5,084,454 | 1/1992 | Varasi et al. | 514/230.5 |
| 5,122,522 | 6/1992 | Laties et al. | 514/220 |
| 5,284,843 | 2/1994 | Stone et al. | 514/213 |
| 5,461,059 | 10/1995 | Bonnet et al. | 514/265 |
| 5,574,044 | 11/1996 | Thompson et al. | 514/316 |

OTHER PUBLICATIONS

H. Bredereck et al., Chem. Ber. 1962, 95, 803–9.
F. Zymalkowski et al., Arch. Pharm. 1966, 299, 363–7.
O. Cervinska et al., Coll. Czechaslov. Chem Commn. 1977, 42, 3464–72.
P. Schenone et al., J. Heterocycl Chem. 1990, 27, 295–305.
B.I. Alo et al., J. Heterocycl Chem. 1992, 69, 61–4.
H. Bredereck et al., Liebigs Ann. Chem. 1971, 766, 73–88.
Chem Abstracts 88: 89666, Tsuda et al., JP52097978, 1977.
Chem Abstracts 88: 190828, Tsuda et al., JP53065174, 1978.

*Primary Examiner*—Matthew V. Grumbling
*Attorney, Agent, or Firm*—Sylvia A. Ayler; Mark R. Daniel

[57] ABSTRACT

Compounds, 1,3-dihydro-1-{1-[piperidin-4-yl]piperidin-4-yl}-2H-benzimidazol-2-ones and 1,3-dihydro-1-{4-amino-1-cyclohexyl}-2H-benzimidazol-2-ones and derivatives thereof, their preparation, method of use and pharmaceutical compositions are described. These compounds are endowed with antimuscarinic activity and are useful in the treatment and/or prevention of myopia (commonly known as nearsightedness).

9 Claims, No Drawings

MUSCARINE ANTAGONISTS

BACKGROUND OF THE INVENTION

This invention relates to control of ocular development in general and, more particularly, to the treatment of the eye to prevent and/or arrest the development of myopia (nearsightedness). Approximately one of every four persons suffer from myopia, i.e., an elongation of the eye along the visual axis. In particular, myopia afflicts 10% to 75% of the youth of the world, depending upon race, geographic distribution and level of education. Myopia is not a trivial maldevelopment of the eye. In its pathologic form, the sclera continues to grow and as result the retina stretches and degenerates resulting in permanent blindness.

Inheritance, environmental forces such as diet, sun intake, and substantial eye use, etc., are but a few theories that have been postulated to explain the on-set of myopia. In that regard, preventive measures such as eye rest, eye exercise, eye glasses, contact lens and drug and surgical therapies have been proposed. However, these measures are neither ideal nor risk-free. The surgical therapies (e.g. corneal surgery using excimer lasers or conventional knives) attempted for this condition are drastic and often unsuccessful. Moreover, neither of the therapies (excimer lasers or conventional knives) are easily reversed or sufficiently predictable in their results. Complications from contact lens wear range from allergic reactions to permanent loss of vision due to corneal ulceration. Even with the complications associated with contact lens wear, there are roughly 24 million wearers in the United States, with the number expected to double in the next 3 years. While eyeglasses eliminate most of the medical risks listed above, they are not an acceptable option as evidenced by the contact lens wearers who tolerate the frustration of contact lens wear.

One particular drug therapy utilized in the treatment of myopia involves the use of cycloplegics. Cycloplegics are topically administered drugs that relax the ciliary muscle of the eye, which is the muscle that focuses the eye by controlling lens dimensions. The classic cycloplegic drug is the belladonna alkaloid atropine, available for over a century. Atropine is a long-acting non-specific antimuscarinic agent that antagonizes the action of the neurotransmitter acetylcholine (ACh) at autonomic effector cells innervated by postganglionic cholinergic nerves of the parasympathetic nervous system. However, use of atropine, is impractical in that it causes mydriasis (increase of pupil size) and its action on the ciliary muscle to inhibit ocular focusing impairs near visual work like reading. There is strong evidence that the receptors in the iris and ciliary muscle responsible for the side effects of atropine are of the M3 subtype. Additionally, studies have shown that muscarinic receptors in the retina of a variety of non-human species are comprised of m1, m2 and m4 subtypes. Accordingly, a muscarinic antagonist with low m3 activity would be efficacious in prevention of the development of myopia without the undesirable side effects associated with the use of atropine.

There is now substantial evidence to link the posterior pan of the eye, specifically image quality at the retina and hence an extension of the nervous system, to the postnatal regulation of ocular growth. There is significant evidence of myopia in an eye that is subjected to retinal image impairment. It has been shown that axial myopia can be experimentally induced, in either birds or primates, in an eye in which the retina is deprived of formed images, e.g., by suturing the eyelids or wearing an image diffusing goggle. The experimental myopia induced in birds or primates such as monkeys mimics, in many respects, the axial myopia of humans.

Thus, the phenomenon of an animal's vision process apparently contributes to the feedback mechanism by which postnatal ocular growth is normally regulated and refractive error is determined. This indicates that this mechanism is neural and likely originates in the retina. R. A. Stone, et al. have found a method of controlling the abnormal postnatal growth of the eye of a maturing animal, which comprises controlling the presence of a neurochemical, its agonist or antagonist, which neurochemical is found to be changed under conditions during maturation leading to abnormal axial length. See U.S. Pat. Nos. 4,066,772 and 5,284,843. Therein it is disclosed that retinal concentrations of dopamine were found to be reduced during such image deprivation and the ocular administration of a dopamine-related agent, e.g., apomorphine, a dopamine agonist, was found to inhibit or actually prevent the axial enlargement of the eye under conditions ordinarily leading to such enlargement.

There have also been recent advances made in the understanding of the cholinergic nervous system and the receptors thereto. Cholinergic receptors are proteins embedded in the wall of a cell that respond to the chemical acetylcholine. Particularly, it is now known that the cholinergic receptors are subdivided into nicotinic and muscarinic receptors and that the muscarinic receptors are not all of the same type. Recent literature indicates that there are at least five types of cholinergic muscarinic receptors (types m1 through m5). Receptors of type m1 are those present in abundance and thought to be enriched in the brain neural tissue and neural ganglia. The other receptors are concentrated in other tissues such as the heart, smooth muscle tissue or glands. While many pharmacological agents interacting with muscarinic receptors influence several types, some agents are known to have a major effect on a single type of receptor with relative selectivity and other agents can have a relatively selective effect on a different single receptor. Still other agents may have a significant effect on more than one or even all types of receptors.

It is known, for example, that pirenzepine, (Gastrozepin, LS 519) 5, 11-Dihydro-11-[4-methyl-1-piperazinyl) acetyl] -6H-pyrido[2,3-b]benzodiazepin-6-one, and its dihydrochloride are anticholinergic, antimuscarinic, and relatively selective for M1 receptors. See U.S. Pat. No. 5,122,522. It is also known that 4-DAMP (4-diphenylacetoxy-N-methylpiperadine methiodide) is a relatively selective antagonist for smooth muscle (ordinarily called M3 type but variously called type M2 or M3, as the current classification of receptors is in flux). Pirenzepine, being primarily an M1 antagonist, inhibits axial elongation, but is far less effective at pupil dilation than atropine or another cycloplegic agent. This makes it possible to suppress the development of myopia without dilating the pupil and paralyzing the accommodation activity of the ciliary muscle. Additionally, the administration of a drug topically into the eye of a developing child for a long period of time makes it desirable to have a minimal likelihood of sensitization of the eye. Pirenzepine and atropine test positive in sensitization assays and this is an undesirable side effect.

SUMMARY OF THE INVENTION

This invention is concerned with novel 1,3-dihydro-1-{1-[piperidin-4-yl]piperidin-4-yl}-2H-benzimidazol-2-ones and 1,3-dihydro-1-{4-amino-1-cyclohexyl}-2H-benzimidazol-2-ones, their compositions and method of use. The novel compounds are selective muscarinic antagonists of the m1, m2, and m4 subtypes with low activity at the m3 subtype. The compounds have good ocular penetration (bioavailability) when dosed as a 0.1–2% aqueous solution, preferably a 0.5–2% solution. The compounds are effective for the treatment and/or prevention of myopia.

DETAILED DESCRIPTION OF THE INVENTION

The novel compounds of this invention are represented by the structural formula:

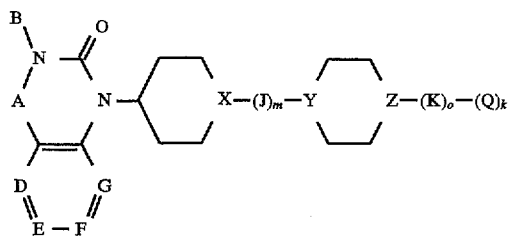

wherein:

C is carbon

H is hydrogen

N is nitrogen

O is oxygen

S is sulfur

P is phosphorus

X, Y, and Z are independently=N, or CH;

J is independently=NB or $CB_2$;

K is independently=NB, $CB_2$, O, carbonyl, thiocarbonyl, sulfonyl, phosphonyl, NBCO, $NBCO_2$, $NBCB_2$, $COCB_2$, CONB, $CO_2$, $CO_2B$, $NB_2$, $NBCONB_2$, $CB_2COCB_2$, $CB_2CONB$, $NBCOCB_2$, or OB;

W is O or $H_2$;

A is $(CH_2)_n$, $(CBH)_n$, $(CB_2)_n$, C=O, or C=S, wherein n is 0, 1 or 2;

m, o & k are 0, 1 or 2;

B is H, Me, Et, Pr, iPr, $CH_2OH$, $CO_2Me$, $CO_2Et$, $CH_2CH_2OH$, $CONH_2$, OH, $NH_2$, NHMe, $NMe_2$, OMe, OEt, CONHMe, or $CONMe_2$

Q is phenyl or heterocycle ring unsubstituted or substituted with Me, Et, Pr, Bu, hydroxyl, alkoxy, F, Cl, Br, I, alkylsulfonyl, phenyl or heterocyclic;

D, E, F & G are chosen from:

| D | E | F | G |
|---|---|---|---|
| N | CR | N | CR |
| CR | CR | CR | CR |
| CR | N | CR | N |
| N | CR | CR | N |
| CR | CR | CR | N |
| CR | CR | N | CR |
| CR | N | CR | CR |
| N | CR | CR | CR |
|  | —S— | CR | CR |
| CR | —S— |  | CR |
| CR | CR |  | —S— |
|  | —O— | CR | CR |
| CR | —O— |  | CR |
| CR | CR |  | —O— |
|  | —NR— | CR | CR |
| CR | —NR— |  | CR |
| CR | CR |  | —NR— |
|  | —NR— | CR | N |
|  | —NR— | N | CR |
| CR | N |  | —NR— |
| N | CR |  | —NR— |
| CR | —NR— |  | N |
| N | —NR— |  | CR |
| N | —S— |  | CR |
| N | —S— |  | N |
| CR | —S— |  | N |
| N | —O— |  | CR |
| N | —O— |  | N |
| CR | —O— |  | N |
| CR | N |  | —S— |
| N | CR |  | —S— |
|  | —S— | CR | N |
|  | —S— | N | CR |
| CR | N |  | —O— |
| N | CR |  | —O— |
|  | —O— | CR | N |
|  | —O— | N | CR | where:

R is independently taken from H, small alkyl, branched alkyl, halo, alkoxy, OH, amino, dialkylamino, or alkylamino.

The term heterocycle or heterocyclic, as used herein except where noted, represents a stable 5- to 7-membered monocyclic heterocyclic ring, which is either saturated or unsaturated, and which consists of carbon atoms and from one to three heteroatoms selected from the group consisting of N, O and S, and including any bicyclic group in which any of the above defined heterocyclic rings is fused to a benzene ring. The heterocyclic ring may be attached at any heteroatom or carbon atom which results in the creation of a stable structure. Examples of such heterocyclic rings include pyridine, pyrazine, pyrimidine, pyridazine, triazine, imidazole, pyrazole, triazole, quinoline, isoquinoline, quinazoline, quinoxaline, phthalazine, oxazole, isoxazole, thiazole, isothiazole, thiadiazole, oxadiazole, pyrrole, furan, thiophene, hydrogenated derivatives of these heterocyles such as piperidine, pyrrolidine, azetidine, tetrahydrofuran, and N-oxide derivatives of heterocyles containing basic nitrogen. Any fused combinations of any of these above-defined heterocyclic rings is also a pan of this definition.

The term alkyl is intended to include both branched and straight chain saturated aliphatic hydrocarbon groups having the specified number of carbon atoms (Me is methyl, Et is ethyl, Pr is propyl, Bu is butyl).

The term alkoxy represents an alkyl group of indicated carbon atoms attached through an oxygen linkage.

The term alkylamino represents an alkyl group of indicated carbon atoms attached through a nitrogen atom linkage.

The term dialkylamino represents two alkyl groups of indicated carbon atoms attached through a nitrogen atom linkage.

The term small alkyl is intended to indicate those alkyls with C1 to C4 carbon atoms, either branched or linear in connection.

The term alkylsulfonyl represents an alkyl group of indicated carbon atoms attached through an sulfonyl ($SO_2$) linkage.

The term halo as used herein, represents fluoro, chloro, bromo or iodo.

A preferred embodiment of the novel compounds of this invention is realized when, 1) X=N, Y=CH, m=0;
2) X=CH, Y=CH, J=NH, m=1; or
3) X=CH, Y=N, m=0.

A more preferred embodiment of the novel compounds of this invention is realized when, 1) X=N, Y=CH, m=0, A is not present, and D,E,F and G are CR where R is defined as above.

The pharmaceutically acceptable salts of the compounds of formula I include the conventional non-toxic salts or the quarternary ammonium salts of the compounds of formula I formed e.g. from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The compounds of the present invention may have asymmetric centers and occur as racemates, racemic mixtures, and as individual diastereomers, with all possible isomers, including optical isomers, being included in the present invention.

Examples of the novel compounds of this invention are as follows:

1,3-dihydro-1-{1-[1-(4-nitrobenzoyl)piperidin-4-yl]piperidin-4-yl}-2H-benzimidazol-2-one, 1,3-dihydro-1-{1-[1-(3-nitrobenzoyl)piperidin-4-yl]piperidin-4-yl}-2H-benzimidazol-2-one, 1,3-dihydro-1-{1-[1-benzyl-4-piperidinyl]piperidin-4-yl}-2H-benzimidazol-2-one, 1,3-dihydro-1-{1-[1-(3-pyridinecarbonyl)piperidin-4-yl]piperidin-4-yl}-2H-benzimidazol-2-one, 1,3-dihydro-1-{1-[1-(2-pyridinecarbonyl)piperidin-4-yl]piperidin-4-yl}-2H-benzimidazol-2-one, 1,3-dihydro-1-{1-[1-(4-pyridinecarbonyl)piperidin-4-yl]piperidin-4-yl}-2H-benzimidazol-2-one, 1,3-dihydro-1-{1-[1-benzoylpiperidin-4-yl]piperidin-4-yl}-2H-benzimidazol-2-one, 1,3-dihydro-1-{1-[1-(3-pyridinecarbonyl)-4-piperidinylmethyl]piperidin-4-yl}-2H-benzimidazol-2-one, 1,3-dihydro-1-{1-[1-(4-pyridinecarbonyl)-4-piperidinylmethyl]piperidin-4-yl }-2H-benzimidazol-2-one, 1,3-dihydro-1-{1-[1-(2-furoyl)piperidin-4-yl]piperidin-4-yl}-2H-benzimidazol-2-one, 1,3-dihydro-1-{-[1-(3,5-dichlorobenzoyl)piperidin-4-yl]piperidin-4-yl}-2-H-benzimidazol-2-one, 1,3-dihydro-1-{1-[1-(2,3,4,5,6-pentafluorobenzoyl)piperidin-4-yl]piperidin-4-yl}-2H-benzimidazol-2-one, 1,3-dihydro-1-{1-[1-(3-benzo[b]thiophenecarbonyl)piperidin-4-yl]piperidin-4-yl}-2H-benzimidazol-2-one, 1,3-dihydro-1-{1-[1-(5,6-dichloro-3-pyridinecarbonyl)piperidin-4-yl]piperidin-4-yl}-2H-benzimidazol-2-one, 1,3-dihydro-1-{1-[1-(2-benzofurancarbonyl)piperidin-4-yl]piperidin-4-yl}-2H-benzimidazol-2-one, 1,3-dihydro-1-{1-[trans-1-benzyloxycarbonylamino-4-cyclohexylmethyl]piperidin-4-yl)-2H-benzimidazol-2-one, 1,3-dihydro-1-{1-[trans-1-phthalimido-4-cyclohexylmethyl]piperidin-4-yl}-2H-benzimidazol-2-one, 1,3-dihydro-1-{1-[trans-4-phthalimidomethyl-1-cyclohexyl]piperidin-4-yl}-2H-benzimidazol-2-one, 1,3-dihydro-1-{1-[1-(2-napthyl)piperidin-4-yl]piperidin-4-yl}-2H-benzimidazol-2-one, 1,3-dihydro-1-{1-[1-(3,4-dichlorobenzoyl)piperidin-4-yl]piperidin-4-yl}-2H-benzimidazol-2-one, 1,3-dihydro-1-{1-[1-(2-methoxybenzoyl)piperidin-4-yl]piperidin-4-yl}-2H-benzimidazol-2-one, 1,3-dihydro-1-{1-[1-(3-chloro-2-benzo[b]thiophenecarbonyl)piperidin-4-yl]piperidin-4-yl}-2H-benzimidazol-2-one, 1,3-dihydro-1-{1-[1-(2,4,6-trichlorobenzoyl)piperidin-4-yl]piperidin-4-yl}-2H-benzimidazol-2-one, 1,3-dihydro-1-{1-[1-(5-isoxazolyl)piperidin-4-yl]piperidin-4-yl}-2H-benzimidazol-2-one, 1,3-dihydro-1-{1-[1-(3,5-dimethyl-4-isoxazolyl)piperidin-4-yl]piperidin-4-yl}-2H-benzimidazol-2-one, 1,3-dihydro-1-{1-[trans-1-(4-nitrobenzamido)-4-cyclohexylmethyl]piperidin-4-yl}-2H-benzimidazol-2-one, 1,3-dihydro-1-{1-[trans-4-ethoxycarbonyl-1-cyclohexyl]piperidin-4-yl}-2H-benzimidazol-2-one, 1,3-dihydro-1-{1-[1-(4-nitrobenzyl)-4-piperidinyl]piperidin-4-yl}-2H-benzimidazol-2-one, 1,3-dihydro-1-{1-[1-(benzyloxycarbonyl)piperidin-4-yl]piperidin-4-yl}-2H-benzimidazol-2-one, 1,3-dihydro-1-{1-[trans-4-hydroxymethyl-1-cyclohexyl]piperidin-4-yl}-2H-benzimidazol-2-one, 1,3-dihydro-1-{1-[1-(4-fluorobenzoyl)piperidin-4-yl]piperidin-4-yl}-2H-benzimidazol-2-one, 1,3-dihydro-1-{1-[1-(4-bromobenzoyl)piperidin-4-yl]piperidin-4-yl}-2H-benzimidazol-2-one, 1,3-dihydro-1-{1-[1-(4-iodobenzoyl)piperidin-4-yl]piperidin-4-yl}-2H-benzimidazol-2-one, 1,3-dihydro-1-{1-[1-(3,4-dimethoxybenzoyl)piperidin-4-yl]piperidin-4-yl}-2H-benzimidazol-2-one, 1,3-dihydro-1-{1-[1-(5-nitro-2-pyridinecarbonyl)piperidin-4-yl]piperidin-4-yl}-2H-benzimidazol-2-one, 1,3-dihydro-1-{1-[trans-1-phthalimido-4-cyclohexyl]piperidin-4-yl}-2H-benzimidazol-2-one, 1,3-dihydro-1-{1-[1-(2-methoxy-4-amino-5-chlorobenzoyl)piperidin-4-yl]piperidin-4-yl}-2H-benzimidazol-2-one, 1,3-dihydro-1-{1-[1-(4-dimethylaminobenzoyl)piperidin-4-yl]piperidin-4-yl}-2H-benzimidazol-2-one, 1,3-dihydro-1-{1-[1-(2-nitrobenzoyl)piperidin-4-yl]piperidin-4-yl}-2H-benzimidazol-2-one, 1,3-dihydro-1-{1-[1-(4-cyanobenzoyl)piperidin-4-yl]piperidin-4-yl}-2H-benzimidazol-2-one, 1,3-dihydro-1-{1-[1-(4-methoxycarbonylbenzoyl)piperidin-4-yl]piperidin-4-yl}-2H-benzimidazol-2-one, 1,3-dihydro-1-{1-[1-(3-(3-pyridyl)acrylyl)piperidin-4-yl]piperidin-4-yl}-2H-benzimidazol-2-one, 1,3-dihydro-1-{1-[1-(6-nitro-3-pyridinecarbonyl)piperidin-4-yl]piperidin-4-yl}-2H-benzimidazol-2-one, 1,3-dihydro-1-{1-[1-(3-methyl-2-pyrazolin-1-yl)piperidin-4-yl]piperidin-4-yl}-2H-benzimidazol-2-one, 1,3-dihydro-1-{1-[1-(6-quinolinecarbonyl)piperidin-4-yl]piperidin-4-yl}-2H-benzimidazol-2-one, 1,3-dihydro-1-{1-[1-(4-acetylbenzoyl)piperidin-4-yl]piperidin-4-yl}-2H-benzimidazol-2-one, 1,3-dihydro-1-{1-[1-(4-methoxybenzoyl)piperidin-4-yl]piperidin-4-yl}-2H-benzimidazol-2-one, 1,3-dihydro-1-{1-[1-(2-phenylbenzoyl)piperidin-4-yl]piperidin-4-yl}-2H-benzimidazol-2-one, 1,3-dihydro-1-{1-[1-(2-methyl-3-pyridinecarbonyl)piperidin-4-yl]piperidin-4-yl}-2H-benzimidazol-2-one, 1,3-dihydro-1-{1-[1-(6-amino-3-pyridinecarbonyl)piperidin-4-yl]piperidin-4-yl}-2H-benzimidazol-2-one, 1,3-dihydro-1-{1-[1-(2-quinolinecarbonyl)piperidin-4-yl]piperidin-4-yl}-2H-benzimidazol-2-one, 1,3-dihydro-1-{1-[1-(5-phenyl-3-pyridinecarbonyl)piperidin-4-yl]piperidin-4-yl}-2H-benzimidazol-2-one, 1,3-dihydro-1-{1-[1-(6-methyl-3-pyridinecarbonyl)piperidin-4-yl]piperidin-4-yl}-2H-benzimidazol-2-one, 1,3-dihydro-1-{1-[1-(6-(4-morpholinyl)-3-pyridinecarbonyl)piperidin-4-yl]piperidin-4-yl}-2H-benzimidazol-2-one, 1,3-dihydro-1-{1-[1-(3-pyridylmethyloxycarbonyl)piperidin-4-yl]piperidin-4-yl}-2H-benzimidazol-2-one, 1,3-dihydro-1-{1-[1-(3-pyridylacetyl)piperidin-4-yl]piperidin-4-yl}-2H-benzimidazol-2-one, 1,3-dihydro-1-{1-[1-(4-methyl-3-pyridinecarbonyl)piperidin-4-yl]piperidin-4-yl}-2H-benzimidazol-2-one, 1,3-dihydro-1-{1-[1-(4-pyridylacetyl)piperidin-4-yl]piperidin-4-yl}-2H-benzimidazol-2-one, 1,3-dihydro-1-{1-[1-(5-methyl-3-pyridinecarbonyl)piperidin-4-yl]piperidin-4-yl}-2H-benzimidazol-2-one, 1,3-dihydro-1-{1-[1-(3-pyridylmethylaminocarbonyl)piperidin-4-yl]piperidin-4-yl}-2H-benzimidazol-2-one, 1,3-dihydro-1-{1-[1-(2R-(1,1-dimethylethoxycarbonylamino)-3-(3-pyridyl)propionyl)piperidin-4-yl]piperidin-4-yl}-2H-benzimidazol-2-one, 1,3-dihydro-1-{1-[1-(2S-(1,1-dimethylethoxycarbonylamino)-3-(3-pyridyl)propionyl)piperidin-4-yl]piperidin-4-yl}-2H-benzimidazol-2-one, 1,3-dihydro-1-{1-[1-(4-pyridylthioacetyl)piperidin-4-yl]piperidin-4-yl}-2H-benzimidazol-2-one, (4'''R,5'''S) and (4'''S,5'''R) 1,3-dihydro-1-(1'-(1''-(1'''-methyl-2'''-oxo-5'''-(3''''-pyridyl)-4'''-pyrrolidinecarbonyl)piperidin-4''-yl)piperidin-4'-yl)-2H-benzimidazol-2-one, 1,3-dihydro-1-{1-[1-(5-pyrimidinecarbonyl)piperidin-4-yl]piperidin-4-yl}-2H-benzimidazol-2-one, 1,3-dihydro-1-{1-[1-(2S-amino-3-(3-pyridyl)propionyl)piperidin-4-yl]piperidin-4-yl}-2H-benzimidazol-2-one, 1,3-dihydro-1-{1-[1-(2R-amino-3-(3-pyridyl)propionyl)piperidin-4-yl]piperidin-4-yl}-2H-benzimidazol-2-one, 1,3-dihydro-1-{1-[1-(2-pyrazinecarbonyl)piperidin-4-yl]piperidin-4-yl}-2H-benzimidazol-2-one, 1,3-dihydro-1-{1-[1-(3-pyridyloxyacetyl)piperidin-4-yl]piperidin-4-yl}-2H-benzimidazol-2-one, 1,3-dihydro-1-{1-[1-(3-(3-pyridyl)propionyl)piperidin-4-yl]piperidin-4-yl}-2H-benzimidazol-2-one, 1,3-dihydro-1-{trans-4-[4-(3-pyridinecarbonyl)piperazin-1-yl]-1-cyclohexyl}-2H-benzimidazol-2-one, 1,3-dihydro-1-{1-[1-(5-pyrimidinecarbonyl)piperidin-4-yl]piperidin-4-yl}-1H-3,4-dihydroquinazolin-2-one, 1,3-dihydro-1-{1-[1-(4-pyridylsulfonyl)acetyl)piperidin-4-yl]piperidin-4-yl}-2H-benzimidazol-2-one, 1,3-dihydro-1-{1-[1-(3-amino-2-pyrazinecarbonyl)piperidin-4-yl]piperidin-4-yl}-2H-benzimidazol-2-one, 1,3-dihydro-1-{1-[1-(4-pyrimidinecarbonyl)piperidin-4-yl]piperidin-4-yl}-2H-benzimidazol-2-one, 1,3-dihydro-1-{1-[1-(4-imidazolecarbonyl)piperidin-4-yl]piperidin-4-yl}-2H-benzimidazol-2-one, 1,3-dihydro-1-{trans-4-[4-(4-nitrobenzoyl)piperazin-1-yl]-1-cyclohexyl}-2H-benzimidazol-2-one, 1,3-dihydro-1-{trans-4-[1-(3-pyridinecarbonyl)-4-piperidinylamino]-1-cyclohexyl}-2H-benzimidazol-2-one, 5-methyl-1,3-dihydro-1-{1-[1-(3-pyridinecarbonyl)piperidin-4-yl]piperidin-4-yl}-2H-benzimidazol-2-one, 1,3-dihydro-1-{trans-4-[4-(5-pyrimidinecarbonyl)piperazin-1-yl]-1-cyclohexyl}-2H-benzimidazol-2-one, 1,3-dihydro-1-{1-[1-(4-amino-5-pyrimidinecarbonyl)piperidin-4-yl]piperidin-4-yl}-2H-benzimidazol-2-one, 1,3-dihydro-1-{1-[1-(3-pyridinemethyl)piperidin-4-yl]piperidin-4-yl}-2H-benzimidazol-2-one, 1,3-dihydro-1-{1-[1-(6-methoxy-2-pyrazinecarbonyl)piperidin-4-yl]piperidin-4-yl}-2H-benzimidazol-2-one, 5-methyl-1,3-dihydro-1-{1-[1-(5-pyrimidinecarbonyl)piperidin-4-yl]piperidin-4-yl}-2H-benzimidazol-2-one, 5-fluoro-1,3-dihydro-1-{1-[1-(5-pyrimidinecarbonyl)piperidin-4-yl]piperidin-4-yl]-2H-benzimidazol-2-one 5-chloro-1,3-dihydro-1-{1-[1-(5-pyrimidinecarbonyl)piperidin-4-yl]piperidin-4-yl}-2H-benzimidazol-2-one, 4-fluoro-1,3-dihydro-1-{1-[1-(5-pyrimidinecarbonyl)piperidin-4-yl]piperidin-4-yl}-2H-benzimidazol-2-one, 6-fluoro-1,3-dihydro-1-{1-[1-(5-pyrimidinecarbonyl)piperidin-4-yl]piperidin-4-yl}-2H-benzimidazol-2-one, 7-fluoro-1,3-dihydro-1-{1-[1-(5-pyrimidinecarbonyl)piperidin-4-yl]piperidin-4-yl}-2H-benzimidazol-2-one, 6-methyl-1,3-dihydro-1-{1-[1-(5-pyrimidinecarbonyl)piperidin-4-yl]piperidin-4-yl}-2H-benzimidazol-2-one, 1,3-dihydro-1-{1-[1-(2-amino-5-pyrimidinecarbonyl)piperidin-4-yl]piperidin-4-yl}-2H-benzimidazol-2-one, 1,3-dihydro-1-{1-[1-(5-pyrimidinecarbonyl)piperidin-4-yl]piperidin-4-yl}-2H-benzimidazol-2-one, 1,3-dihydro-1-{1-[1-(6-methylamino-2-pyrazinecarbonyl)piperidin-4-yl]piperidin-4-yl}-2H-benzimidazol-2-one, 1,3-dihydro-1-{1-[1-(6-dimethylamino-2-pyrazinecarbonyl)piperidin-4-yl]piperidin-4-yl}-2H-benzimidazol-2-one, 1,3-dihydro-1-{1-[1-(6-piperidino-2-pyrazinecarbonyl)piperidin-4-yl]piperidin-4-yl}-2H-benzimidazol-2-one, 1,3-dihydro-1-{1-[1-(6-pyrrolidinyl-2-pyrazinecarbonyl)piperidin-4-yl]piperidin-4-yl}-2H-benzimidazol-2-one, 5-methyl-1,3-dihydro-1-{1-[1-(5-pyrimidinemethyl)piperidin-4-yl]piperidin-4-yl}-2H-benzimidazol-2-one, 1,3-dihydro-1-{trans-4-[4-(5-pyridinecarbonylamino)piperidin-1-yl]-1-cyclohexyl}-2H-benzimidazol-2-one, 1,3-dihydro-1-{1-[1-(4-pyridazinecarbonyl)piperidin-4-yl]piperidin-4-yl}-2H-benzimidazol-2-one, 1,3-dihydro-1-{1-[1-(6-benzyloxy-2-pyrazinecarbonyl)piperidin-4-yl]piperidin-4-yl}-2H-benzimidazol-2-one, 1,3-dihydro-1-{1-[1-(6-chloro -2-pyrazinecarbonyl)piperidin-4-yl]piperidin-4-yl}-2H-benzimidazol-2-one, 4-methyl-1,3-dihydro-1-{1-[1-(3-pyridinecarbonyl)piperidin-4-yl]piperidin-4-yl}-2H-benzimidazol-2-one, 5-ethyl-1,3-dihydro-1-{1-[1-(5-pyrimidinecarbonyl)piperidin-4-yl]piperidin-4-yl}-2H-benzimidazol-2-one, 5-methoxy-1,3-dihydro-1-{1-[1-(5-pyrimidinecarbonyl)piperidin-4-yl]piperidin-4-yl}-2H-benzimidazol-2-one, 5-hydroxy-1,3-dihydro-1-{1-[1-(5-pyrimidinecarbonyl)piperidin-4-yl]piperidin-4-yl}-2H-benzimidazol-2-one, 5-ethoxy-1,3-dihydro-1-{1-[1-(5-pyrimidinecarbonyl) piperidin-4-yl]piperidin-4-yl}-2H-benzimidazol-2-one,
5-(2-hydroxyethoxy)-1,3-dihydro-1-{1-[1-(5-pyrimidinecarbonyl)piperidin-4-yl]piperidin-4-yl}-2H-benzimidazol-2-one,
1,3-dihydro-1-{1-[1-(6-amino-2-pyrazinecarbonyl) piperidin-4-yl]piperidin-4-yl}-2H-benzimidazol-2-one,
1,3-dihydro-3-{1-[1-(3-pyridinecarbonyl)piperidin-4-yl] piperidin-4-yl}-2H-2-oxo-imidazo[4,5-b]pyridine,
1,3-dihydro-1-{1-[trans-4-(3-pyridinecarbonylamino) cyclohexyl]piperidin-4-yl}-2H-benzimidazol-2-one,
1,3-dihydro-1-{1-[4-(1,3-dihydro-2-oxo-2H-benzimidazolin-1-yl)cyclohexyl]piperidin-4-yl}-2H-benzimidazol-2-one,
1,3-dihydro-1-{1-[cis-4-(3-pyridinecarbonylamino) cyclohexyl]piperidin-4-yl}-2H-benzimidazol-2-one,
5-propyl-1,3-dihydro-1-{1-[1-(5-pyrimidinecarbonyl) piperidin-4-yl]piperidin-4-yl}-2H-benzimidazol-2-one,
5-butyl-1,3-dihydro-1-{1-[1-(5-pyrimidinecarbonyl) piperidin-4-yl]piperidin-4-yl}-2H-benzimidazol-2-one,
5-(1-methylethyl)-1,3-dihydro-1-{1-[1-(5-pyrimidinecarbonyl)piperidin-4-yl]piperidin-4-yl}-2H-benzimidazol-2-one,
5-(1-hydroxyethyl)-1,3-dihydro-1-{1-[1-(5-pyrimidinecarbonyl)piperidin-4-yl]piperidin-4-yl}-2H-benzimidazol-2-one,
4-methyl-1,3-dihydro-1-{1-[1-(5-pyrimidinecarbonyl) piperidin-4-yl]piperidin-4-yl}-2H-benzimidazol-2-one,
4-ethyl-1,3-dihydro-1-{1-[1-(5-pyrimidinecarbonyl) piperidin-4-yl]piperidin-4-yl}-2H-benzimidazol-2-one,
5,6-dimethyl-1,3-dihydro-1-{1-[1-(5-pyrimidinecarbonyl) piperidin-4-yl]piperidin-4-yl}-2H-benzimidazol-2-one,
4,5-dimethyl-1,3-dihydro-1-{1-[1-(5-pyrimidinecarbonyl) piperidin-4-yl]piperidin-4-yl}-2H-benzimidazol-2-one,
1,3-Dihydro-1-{1-[1-(5-pyrimidinylcarbonyl)piperidin-4-yl]piperidin-4-yl}-1H-3,4-dihydroquinazolin-2-one,
(±)-1,3-Dihydro-1-{1-[1-(1-(5-pyrimidinyl)-ethyl) piperidin-4-yl]piperidin-4-yl}-2H-benzimidazol-2-one,
(1'''S) 1,3-Dihydro-1-{1'-[1''-(1'''-(5''''-pyrimidinyl)-ethyl) piperidin-4''-yl]piperidin-4'-yl}-2H-benzimidazol-2-one,
(1'''R) 1,3-Dihydro-1-{1'-[1''-(1'''-(5''''-pyrimidinyl)-ethyl)piperidin-4''-yl]piperidin-4'-yl}-2H-benzimidazol-2-one,
(1'''S ) 1,3-Dihydro-1-{1'-[1''-(1'''-(5''''-pyrimidinyl)-ethyl) piperidin-4''-yl]piperidin-4'-yl}-5-chloro-2H-benzimidazol-2-one,
(1'''R) 1,3-Dihydro-1-{1'-[1''-(1'''-(5''''-pyrimidinyl)-ethyl) piperidin-4''-yl]piperidin-4'-yl}-5-chloro-2H-benzimidazol-2-one,
(1'''S) 1,3-Dihydro-1-{1'-[1''-(1'''-(5''''-pyrimidinyl)-ethyl) piperidin-4''-yl]piperidin-4'-yl}-5-methyl-2H-benzimidazol-2-one,
(1'''R) 1,3-Dihydro-1-[1'-[1''-(1'''-(5''''-pyrimidinyl)-ethyl) piperidin-4''-yl]piperidin-4'-yl}-5-methyl-2H-benzimidazol-2-one,
1,3-Dihydro-1-{1-[4-oxocyclohex-1-yl]piperidin-4-yl}-2H-benzimidazol-2-one,
cis-1,3-Dihydro-1-{1-[1-(5-pyrimidinylamino)cyclohex-4-yl]piperidin-4-yl}-2H-benzimidazol-2-one,
trans-1,3-Dihydro-1-{1-[1-(5-pyrimidinylamino)cyclohex-4-yl]piperidin-4-yl}-2H-benzimidazol-2-one,
trans-1,3-Dihydro-1-{4-[4-(3-pyridinylmethyl)piperazin-1-yl]-1-cyclohexyl}-2H-benzimidazol-2-one,
1,3-Dihydro-1-{1-[1-(2-pyrazinylmethyl)piperidin-4-yl] piperidin-4-yl}-2H-benzimidazol-2-one,
(±)-cis-1,3-Dihydro-1-(1-{4-[(5-pyrimidinyl) hydroxymethyl]cyclohex-1-yl}piperidin-4-yl)-2H-benzimidazol-2-one,
(±)-trans-1,3-Dihydro-1-(1-{4-[(5-pyrimidinyl) hydroxymethyl]cyclohex-1-yl}piperidin-4-yl)-2H-benzimidazol-2-one,
trans-1,3-Dihydro-1-{1-[4-(5-pyrimidinylcarbonyl) cyclohex-1-yl]piperidin-4-yl}-2H-benzimidazol-2-one,
cis-1,3-Dihydro-1-{1-[1-(3-pyridylamino)cyclohex-4-yl] piperidin-4-yl}-2H-benzimidazol-2-one,
trans-1,3-Dihydro-1-{1-[1-(3-pyridylamino)cyclohex-4-yl] piperidin-4-yl}-2H-benzimidazol-2-one,
(±)-1,3-Dihydro-1-(1-{1-[1-(2-pyrazinyl)-ethyl]piperidin-4-yl}piperidin-4-yl)-2H-benzimidazol-2-one,
(±) 1,3-Dihydro-1-{1'-[1''-(1'''-(5''''-pyridinyl)-ethyl) piperidin-4''-yl]piperidin-4'-yl}-2H-benzimidazol-2-one,
(1'''R) 1,3-Dihydro-1-{1'-[1''-(1'''-(5''''-pyridinyl)-ethyl) piperidin-4''-yl]piperidin-4'-yl}-2H-benzimidazol-2-one,
(1'''R) 1,3-Dihydro-1-{1'-[1''-(1'''-(5''''-pyridinyl)-ethyl) piperidin-4''-yl]piperidin-4'-yl}-5-chloro-2H-benzimidazol-2-one,
(1'''R) 1,3-Dihydro-1-{1'-[1''-(1'''-(5''''-pyridinyl)-ethyl) piperidin-4''-yl]piperidin-4'-yl}-5-methyl-2H-benzimidazol-2-one,
(±)-1,3-Dihydro-1-(1-{1-[1-(2-pyrazinyl)-1-ethyl]piperidin-4-yl}piperidin-4-yl)-5-methyl-2H-benzimidazol-2-one,
(±)-1,3-Dihydro-1-(1-{1-[1-(2-pyrazinyl)-1-ethyl]piperidin-4-yl}piperidin-4-yl)-5-chloro-2H-benzimidazol-2-one,
1,3-dihydro-1-(1-{1-[2-(5-pyrimidinyl)-prop-2-yl] piperidin-4-yl}piperidin-4-yl)-2H-benzimidazol-2-one,
1,3-dihydro-1-(1-{1-[2-(5-pyrimidinyl)-prop-2-yl] piperidin-4-yl}piperidin-4-yl)-5-methyl-2H-benzimidazol-2-one,
1,3-dihydro-1-(1-{1-[2-(5-pyrimidinyl)-prop-2-yl] piperidin-4-yl}piperidin-4-yl)-5-chloro-2H-benzimidazol-2-one,
1,3-dihydro-5-methyl-1-(1-{1-[2-(3-pyridyl)-prop-2-yl] piperidin-4-yl}piperidin-4-yl)-2H-benzimidazol-2-one,
1,3-dihydro-(1-{1-[2-(3-pyridyl)-prop-2-yl]piperidin-4-yl}piperidin-4-yl)-2H-benzimidazol-2-one,
1,3-dihydro-1-{1-[1-(2-phenyl-5-pyrimidinylcarbonyl) piperidin-4-yl]piperidin-4-yl}-2H-benzimidazol-2-one,
1,3-Dihydro-1-{1-[1-(3-pyridinesulfonyl)piperidin-4-yl] piperidin-4-yl}-2H-benzimidazol-2-one,
1,3-dihydro-1-{1-[1-(2-methyl-5-pyrimidinylcarbonyl) piperidin-4-yl]piperidin-4-yl}-2H-benzimidazol-2-one,
1,3-Dihydro-1-{1-[1-(5-pyrimidinylmethyl)piperidin-4-yl] piperidin-4-yl}-2H-benzimidazol-2-one,
1,3-Dihydro-1-{1-[1-(4-imidazolylmethyl)piperidin-4-yl ]piperidin-4-yl}-2H-benzimidazol-2-one,
1,3-dihydro-1-{1-[1-(2-amino-5-pyrimidinylcarbonyl) piperidin-4-yl]piperidin-4-yl}-2H-benzimidazol-2-one,
(1'''R)-1,3-Dihydro-1-{1'-[1''-(1'''-phenylethyl)piperidin-4''-yl]piperidin-4'-yl}-2H-benzimidazol-2-one,
(1'''S)-1,3-Dihydro-1-{1'-[1''-(1'''-phenylethyl)piperidin-4''-yl]piperidin-4'-yl}-2H-benzimidazol-2-one,
(1'''R)-1,3-Dihydro-1-{1'-[1''-(2'''-hydroxy-1'''-phenylethyl) piperidin-4''-yl]piperidin-4'-yl}-2H-benzimidazol-2-one,
(1'''S )-1,3-Dihydro-1-{1'-[1''-(2'''-hydroxy-1'''-phenylethyl) piperidin-4''-yl]piperidin-4'-yl}-2H-benzimidazol-2-one,
trans-1,3-Dihydro-1-{1-[4-hydroxycyclohex-1-yl]piperidin-4-yl}-2H-benzimidazol-2-one, or
cis-1,3-Dihydro-1-{1-[4-hydroxycyclohex-1-yl]piperidin-4-yl}-2H-benzimidazol-2-one.

The most preferred compounds are as follows:

5-methyl-1,3-dihydro-1-{1-[1-(3-pyridinecarbonyl) piperidin-4-yl]piperidin-4-yl}-2H-benzimidazol-2-one
1,3-dihydro-1-{1-[1-(5-pyrimidinecarbonyl)piperidin-4-yl] piperidin-4-yl}-2H-benzimidazol-2-one 1,3-dihydro-1-{1-[1-(2-pyrazinecarbonyl)piperidin-4-yl]
    piperidin-4-yl}-2H-benzimidazol-2-one
1,3-dihydro-1-{1-[1-(3-pyridinemethyl)piperidin-4-yl]
    piperidin-4-yl}-2H-benzimidazol-2-one
5-methoxy-1,3-dihydro-1-{1-[1-(5-pyrimidinecarbonyl)
    piperidin-4-yl]piperidin-4-yl}-2H-benzimidazol-2-one
5-methyl-1,3-dihydro-1-{1-[1-(5-pyrimidinecarbonyl)
    piperidin-4-yl]piperidin-4-yl}-2H-benzimidazol-2-one
5-ethyl-1,3-dihydro-1-{1-[1-(5-pyrimidinecarbonyl)
    piperidin-4-yl]piperidin-4-yl}-2H-benzimidazol-2-one
(1'''R) 1,3-Dihydro-1-{1'-[1"-(1'''-(5""-pyrimidinyl)-ethyl)
    piperidin-4"-yl]piperidin-4'-yl}-2H-benzimidazol-2-one
(1'''R) 1,3-Dihydro-1-{1'-[1"-(1'''-(5""-pyrimidinyl)-ethyl)
    piperidin-4"-yl]piperidin-4'-yl}-5-chloro-2H-
    benzimidazol-2-one
(1'''R) 1,3-Dihydro-1-{1'-[1"-(1'''-(5""-pyrimidinyl)-ethyl)
    piperidin-4"-yl]piperidin-4'-yl}-5-methyl-2H-
    benzimidazol-2-one
1,3-Dihydro-1-{1-[4-oxocyclohex-1-yl]piperidin-4-yl}-2H-
    benzimidazol-2-one
trans-1,3-Dihydro-1-{1-[1-(5-pyrimidinylamino)cyclohex-
    4-yl]piperidin-4-yl}-2H-benzimidazol-2-one
trans-1,3-Dihydro-1-{1-[1-(3-pyridylamino)cyclohex-4-yl]
    piperidin-4-yl}-2H-benzimidazol-2-one
(1'''R) 1,3-Dihydro-1-{1'-[1"-(1'''-(5""-pyridinyl)-ethyl)
    piperidin-4"-yl]piperidin-4'-yl}-2H-benzimidazol-2-one
(1'''R) 1,3-Dihydro-1-{1'-[1"-(1'''-(5""-pyridinyl)-ethyl)
    piperidin-4"-yl]piperidin-4'-yl}-5-chloro-2H-
    benzimidazol-2-one
(1'''R) 1,3-Dihydro-1-{1'-[1"-(1'''-(5""-pyridinyl)-ethyl)
    piperidin-4"-yl]piperidin-4'-yl}-5-methyl-2H-
    benzimidazol-2-one The novel compounds of this invention are prepared by the following non-limiting procedures: Compounds of the formula I, where X=N, Y=CH and m=0, can be prepared by a number of routes, including the following:

Method A

This can be illustrated as follows:

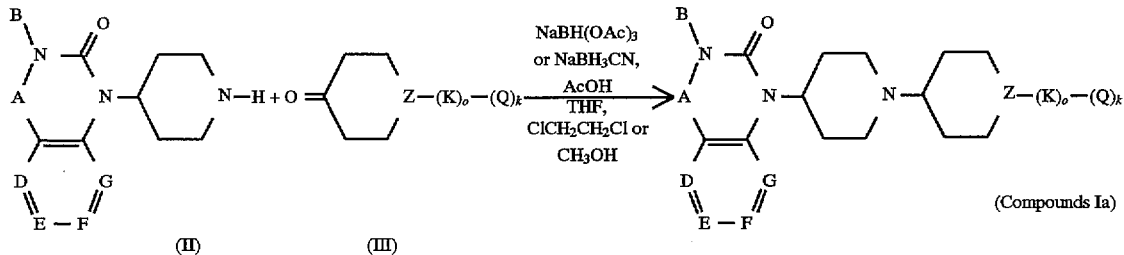

The reaction is preferably carried out at room temperature (20°–30° C.) at a pH in the range of 2–7 (acidic) by the addition of glacial acetic acid or hydrochloric acid. For the preferred examples where Z=N; and o=1, a suitably protected piperidone of formula III such as where o=1, k=0 and K=CO$_2$CH$_2$Ph, CO$_2$C(CH$_3$)$_3$, CO$_2$CH$_3$ or CO$_2$CH$_2$CH$_3$ can be used as an intermediate. Similarly, for the examples where Z=CH, K=NH, o=1 and k=1 a suitably protected 4-aminocyclohexanone of formula III such as where o=1, k=0, K=NHCO$_2$CH$_2$Ph, NHCO$_2$C(CH$_3$)$_3$, NHCO$_2$CH$_3$, NHCO$_2$CH$_2$CH$_3$ or N$_3$ can be used as an intermediate. Deprotection by the usual methods (hydrogenation or acidic hydrolysis followed by basification) provides the free amine compound which can be acylated or alkylated by standard procedures. By this route the most preferred compounds can be obtained after isolation and purification.

The starting materials of the formula (II) and (III) are either commercially available or can be obtained by conventional procedures such as those described in the Examples section.

Compounds of the formula I, where X=CH, Y=N and m=0 can be prepared by a number of routes, including the following:

Method B

This can be illustrated as follows:

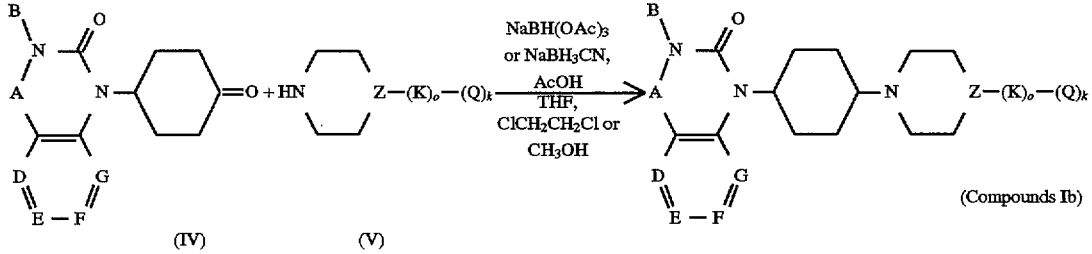

The reaction is preferably carried out at room temperature (20°–30° C.) at a pH in the range of 2–7 (acidic) by the addition of glacial acetic acid or hydrochloric acid. For the preferred examples where Z=N and o=1, a suitably protected piperazine of formula V such as where k=0 and K=CO$_2$CH$_2$Ph, CO$_2$C(CH$_3$)$_3$, CO$_2$CH$_3$ or CO$_2$CH$_2$CH$_3$ can be used as an intermediate. Similarly, for the preferred examples where Z=CH, K=NH, and o=1, a suitably protected 4-aminopiperidine such as formula V where o=1, k=0 and K=NHCO$_2$CH$_2$Ph, NHCO$_2$C(CH$_3$)$_3$, NHCO$_2$CH$_3$, NHCO$_2$CH$_2$CH$_3$ or N$_3$ can be used as an intermediate. Deprotection by the usual methods hydrogenation or acidic hydrolysis followed by basification) provides the free amine compound which can be acylated or alkylated by standard procedures. By this route the preferred compounds can be obtained after isolation and purification. The more preferred trans-isomer is either formed selectively by control of the reaction conditions, or separated by chromatography.

The novel starting materials of the formula (IV) can be obtained by conventional procedures such as those described in the Examples section. The starting materials of the formula (V) are either commercially available or can be obtained by conventional procedures such as those described in the Examples section.

Compounds of the formula I, where X=CH, Y=CH, J=NH and m=1 can be prepared by a number of routes, including the following:

Method C

This can be illustrated as follows:

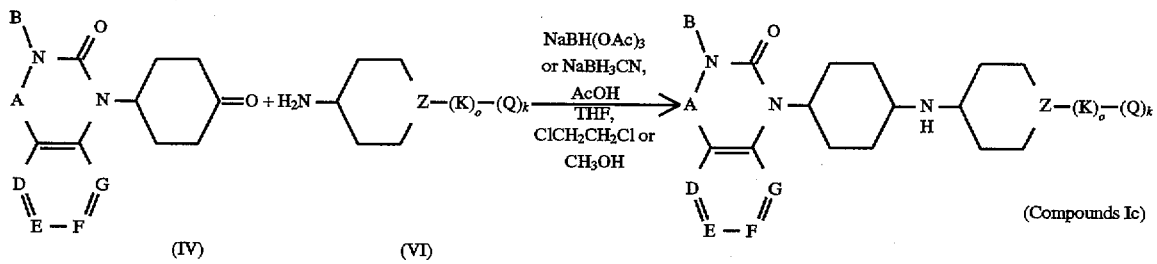

The reaction is preferably carried out at room temperature (20°–30° C.) at a pH in the range of 2–7 (acidic) by the addition of glacial acetic acid or hydrochloric acid. For the

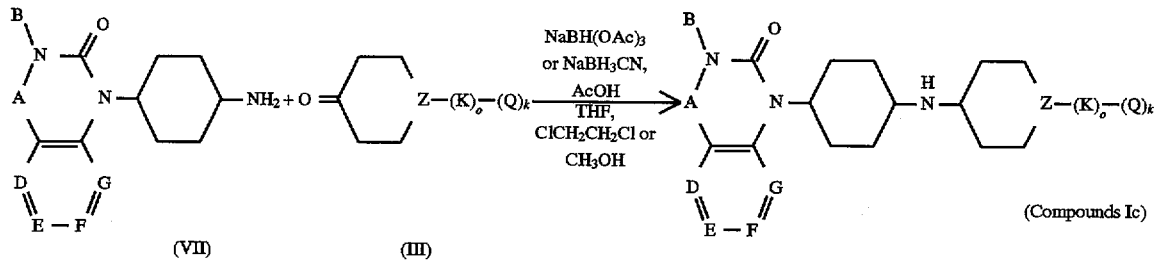

preferred examples where Z=N a suitably protected 4-aminopiperidine of formula VI such as where o=1 and k=0 and K=$CO_2CH_2Ph$, $CO_2C(CH_3)_3$, $CO_2CH_3$ or $CO_2CH_2CH_3$ can be used as an intermediate. Similarly, for the preferred examples where Z=CH and k=1, a suitably mono- protected 1,4-diaminocyclohexane of formula VI such as where o=1, k=0 and K=$NHCO_2CH_2Ph$, $NHCO_2C(CH_3)_3$, $NHCO_2CH_3$, $NHCO_2CH_2CH_3$ or $N_3$ can be used as an intermediate. Deprotection by the usual methods (hydrogenation or acidic hydrolysis followed by basification) provides the free amine compound which can be acylated or alkylated by standard procedures. By this route the preferred compounds can be obtained after isolation and purification. The more preferred trans-isomer is either formed selectively by control of the reaction conditions, or separated by chromatography.

The novel starting materials of the formula (IV) can be obtained by conventional procedures such as those described in the Examples section. The starting materials of the formula (VI) are either commercially available or can be obtained by conventional procedures such as those described in the Examples section.

Compounds of the formula I, where X=CH, Y=CH, J=NH and m=1 can also be prepared by the following:

Method D

This can be illustrated as follows:

The reaction is preferably carded out at room temperature (20°–30° C.) at a pH in the range of 2–7 (acidic) by the addition of glacial acetic acid or hydrochloric acid. For the preferred examples where Z=N, a suitably protected piperidone of formula III such as where o=1, k=0, and K=$CO_2CH_2Ph$, $CO_2C(CH_3)_3$, $CO_2CH_3$ or $CO_2CH_2CH_3$ can be used as an intermediate. Similarly, for the preferred examples where Z=CH, o=1, and J=NH, a suitably mono-protected 4-aminocyclohexanone of formula III such as where o=1 and k=0 and K=$NHCO_2CH_2Ph$, $NHCO_2C(CH_3)_3$, $NHCO_2CH_3$, $NHCO_2CH_2CH_3$ or $N_3$ can be used as intermediate. Deprotection by the usual methods (hydrogenation or acidic hydrolysis followed by basification) provides the free amine compound which can be acylated or alkylated by standard procedures. By this route the preferred compounds can be obtained after isolation and purification. The more preferred trans-isomer is either formed selectively by control of the reaction conditions, or separated by chromatography.

The novel starting materials of the formula (VII) can be obtained by conventional procedures such as those described in the Examples section. The starting materials of the formula (III) are either commercially available or can be obtained by conventional procedures such as those described in the Examples section.
The compounds of the present invention include, but are not limited by the following Tables (1-4).
TABLE 1
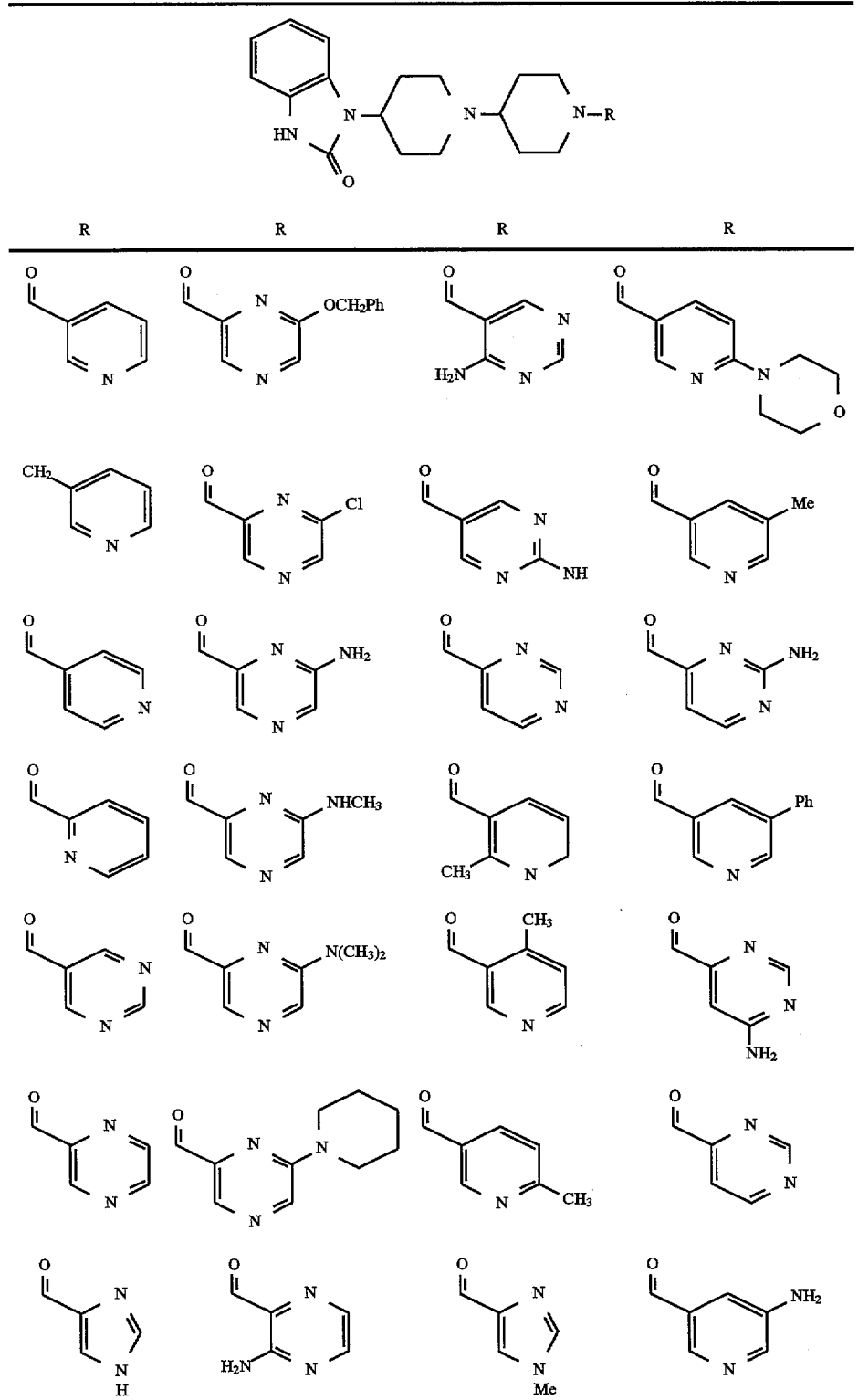

TABLE 1-continued
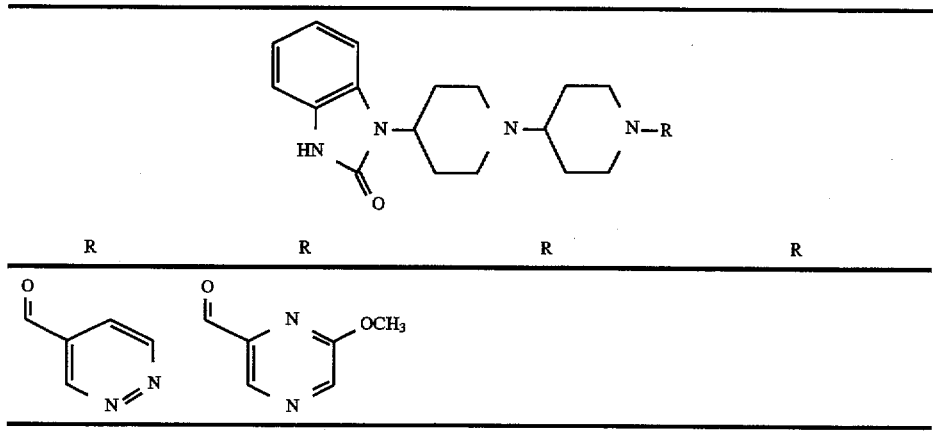
TABLE 2
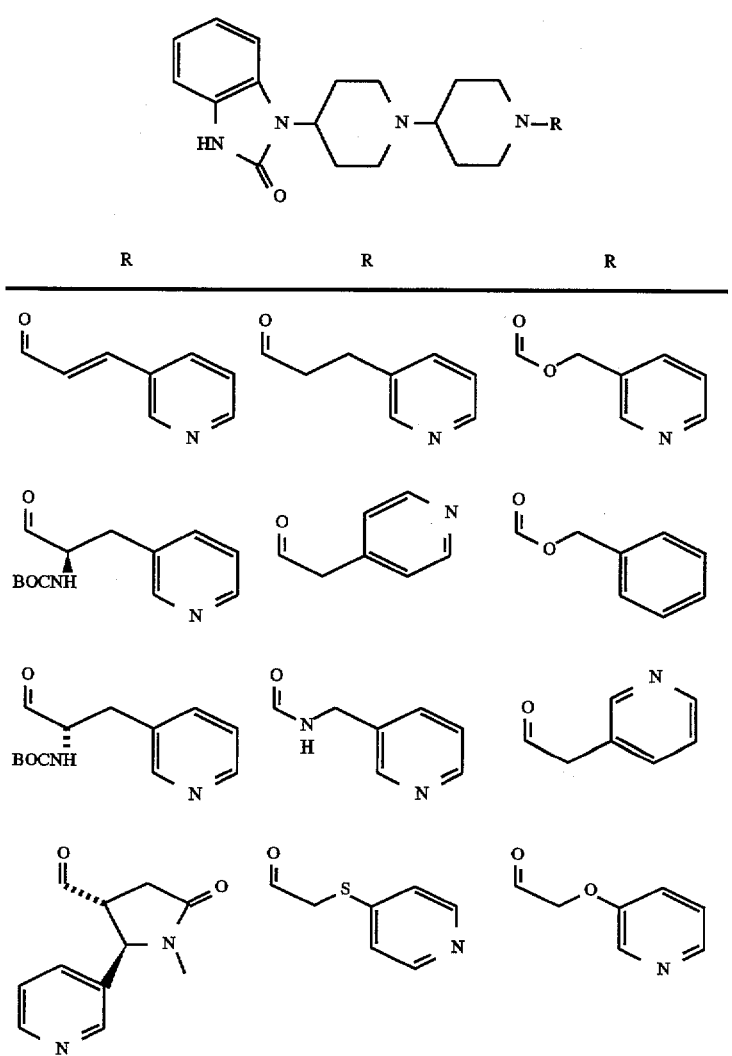

TABLE 2-continued
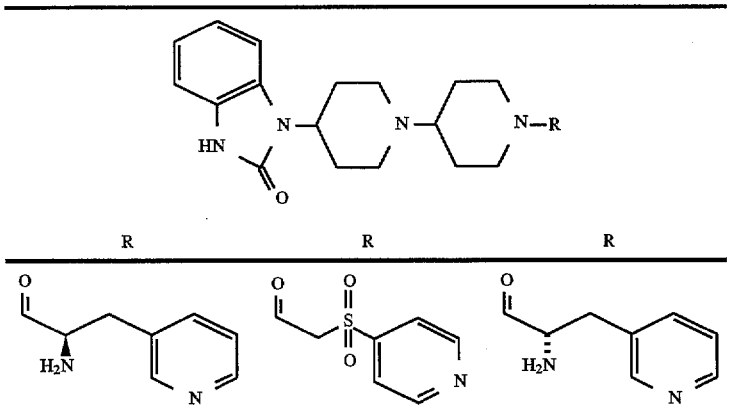
TABLE 3
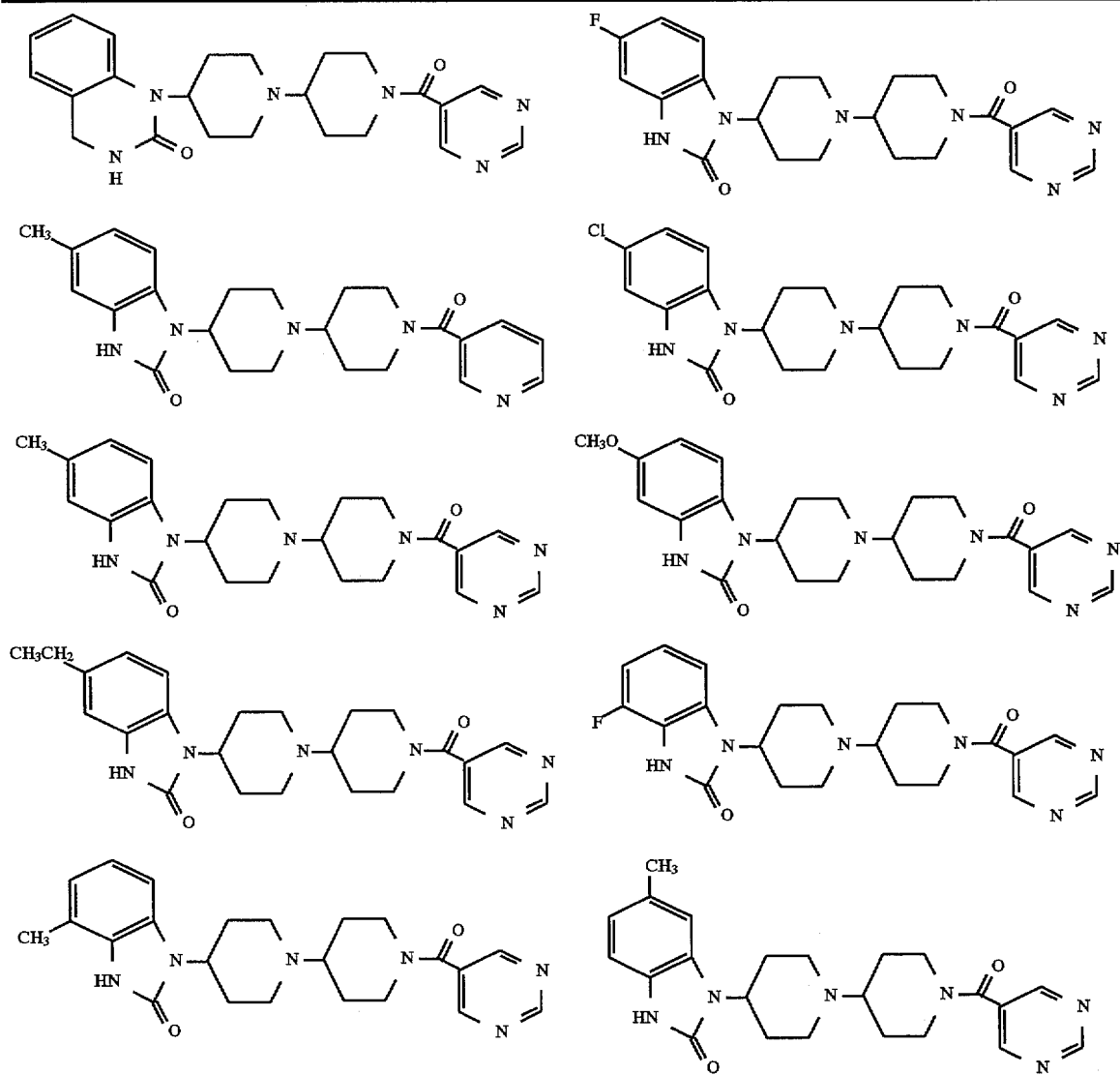

TABLE 3-continued
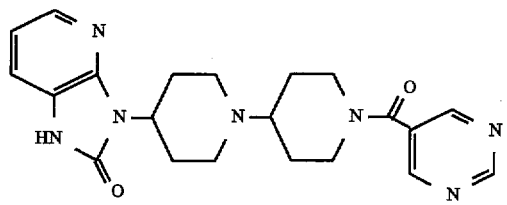 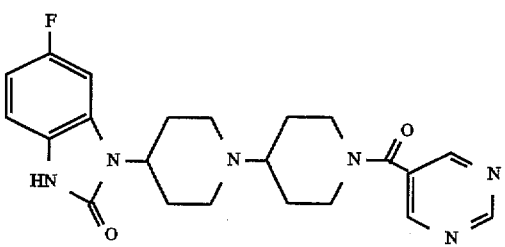
TABLE 4
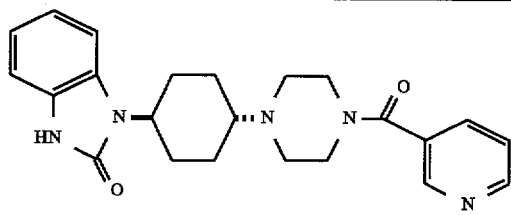 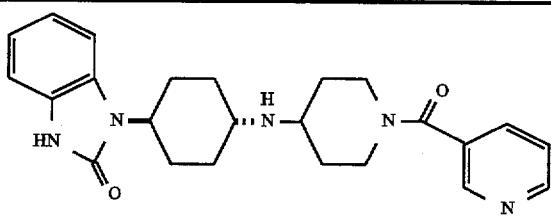
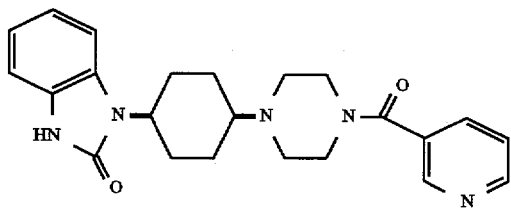 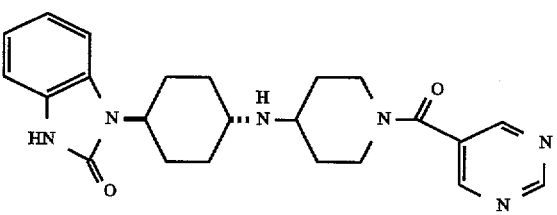
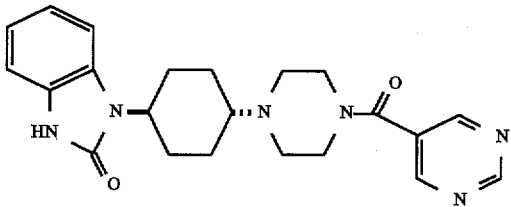 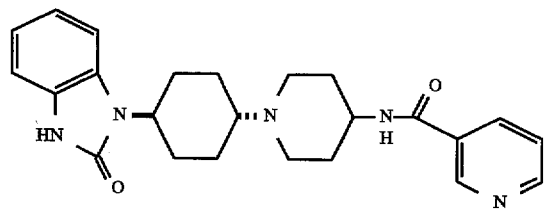
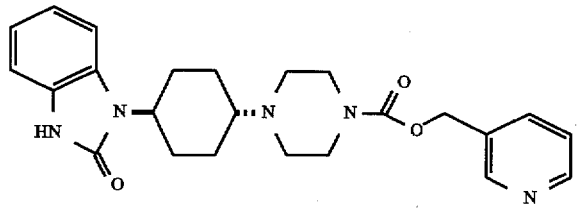 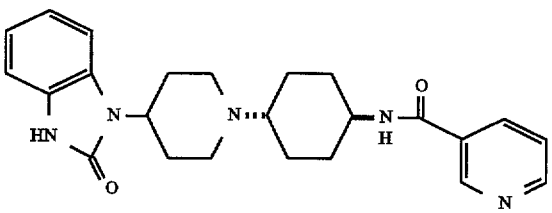
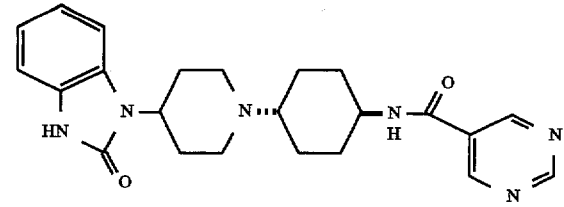 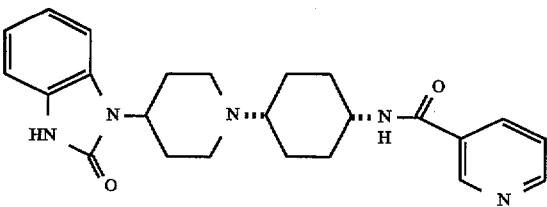

TABLE 5

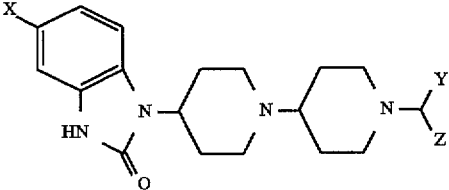

| X | Y | Z | X | Y | Z |
|---|---|---|---|---|---|
| H | $CH_3$ | phenyl | H | $CH_2OH$ | phenyl |
| H | $CH_3$ | 3-pyridinyl | H | $CH_2OH$ | 3-pyridinyl |
| H | $CH_3$ | 5-pyrimidinyl | H | $CH_2OH$ | 5-pyrimidinyl |
| H | $CH_3$ | 2-pyrazinyl | H | $CH_2OH$ | 2-pyrazinyl |
| $CH_3$ | $CH_3$ | phenyl | $CH_3$ | $CH_2OH$ | phenyl |
| $CH_3$ | $CH_3$ | 3-pyridinyl | $CH_3$ | $CH_2OH$ | 3-pyridinyl |
| $CH_3$ | $CH_3$ | 5-pyrimidinyl | $CH_3$ | $CH_2OH$ | 5-pyrimidinyl |
| $CH_3$ | $CH_3$ | 2-pyrazinyl | $CH_3$ | $CH_2OH$ | 2-pyrazinyl |
| Cl | $CH_3$ | phenyl | Cl | $CH_2OH$ | phenyl |
| Cl | $CH_3$ | 3-pyridinyl | Cl | $CH_2OH$ | 3-pyridinyl |
| Cl | $CH_3$ | 5-pyrimidinyl | Cl | $CH_2OH$ | 5-pyrimidinyl |
| Cl | $CH_3$ | 2-pyrazinyl | Cl | $CH_2OH$ | 2-pyrazinyl |

TABLE 6

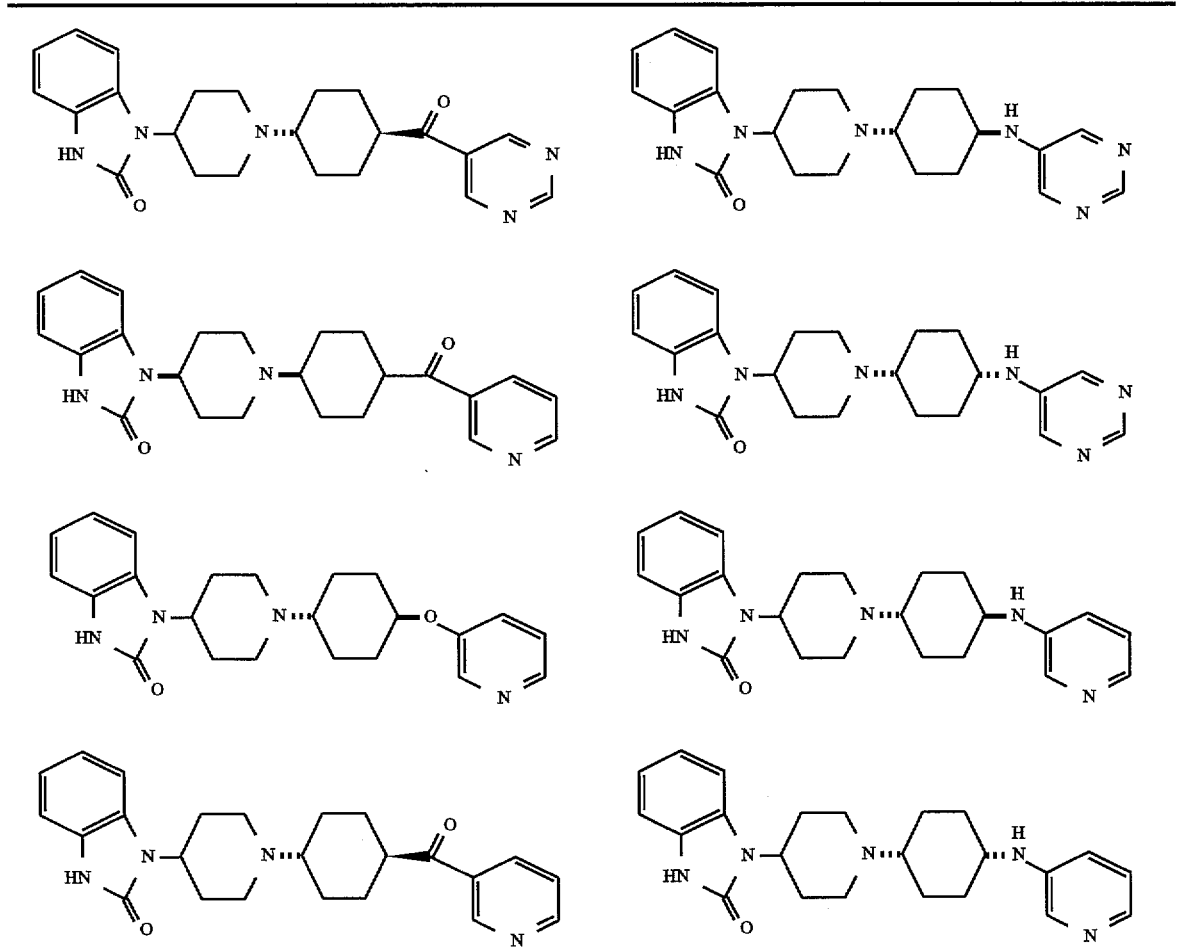

TABLE 6-continued
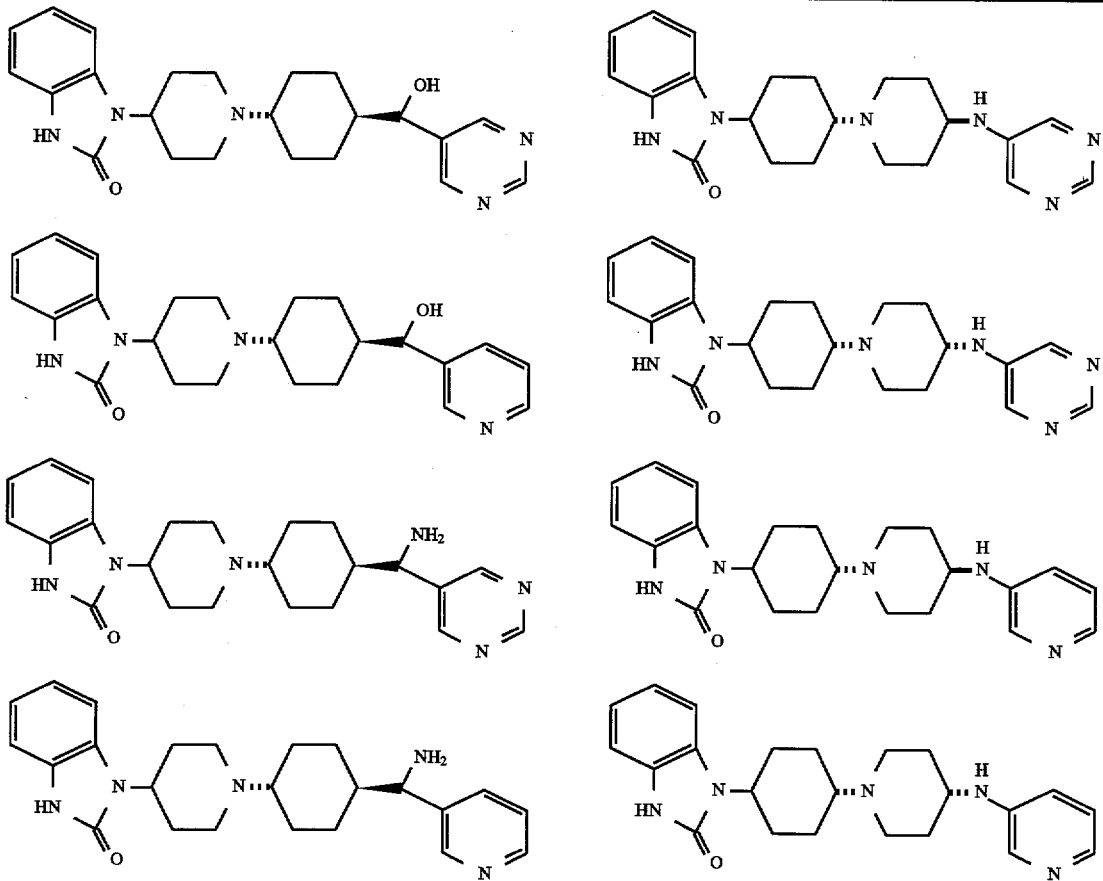
TABLE 7
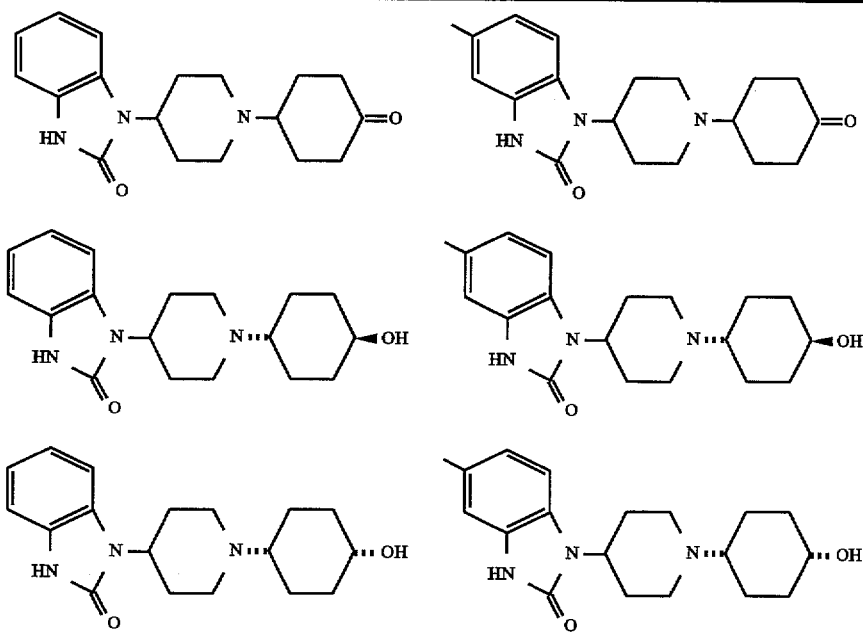

TABLE 7-continued

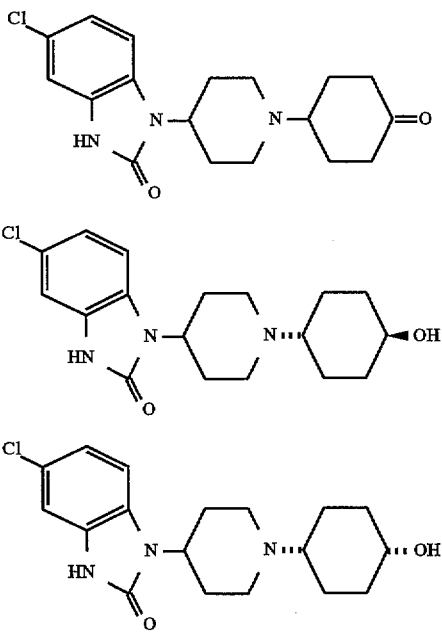

The selectivity of the compounds can be measured by radioligand displacement from m1-m5 receptors expressed in chinese hamster ovary cells (CHO) as described in the Examples section. The functional activity of the compounds can be assessed by measuring the agonist induced contractile response on muscle tissue from rabbit vas deferens (M1), the guinea pig left atria (M2), or the guinea pig ileum (M3) as described in the Examples section. The functional activity at the human muscarinic receptors can be assessed by measuring agonist induced phosphoinositide hydrolysis in CHO cells expressing the human m1 and m3 receptors or agonist inhibition of foskolin-stimulated adenylate cyclase activity in CHO cells expressing the human m2 receptor as described in the Examples section.

The instant compounds of this invention are useful in treating and/or preventing the development of myopia. Therapy to inhibit axial-elongation myopia during maturation can be administered by the use of the agent in eye drops. Indeed, in the vast majority of cases, treatment agents are administered to human eyes by the application of eye drops. Eye drops are typically made up at a concentration of active agent between about 0.1 and 2% in the ophthalmic medium. A 0.5%–2% solution of the instant muscarinic antagonist in water would be a likely concentration for clinical use. A pH of about 4.5 to about 7.5 is expected to be acceptable as an ophthalmic drop and practical in terms of known solubility and stability of piperidines. Phosphate buffering is also common for eye drops and is compatible with the instant muscarinic antagonist. A common regimen for application of eye drops is one to three times a day spaced evenly throughout waking hours. More effective agents may require fewer applications or enable the use of more dilute solutions. Alternatively, ointments and solid inserts are now coming into increased use in clinical practice. These aid the ocular penetration of the drug. It is, of course, also possible to administer the above-described active agents in therapeutically effective amounts and dosages in pills, capsules, or other preparations of systemic administration.

In experiments in animals where axial myopia has been experimentally induced by depriving the retina of formed images, it has been noted by others in primates that amblyopia was also experimentally and coincidentally induced. Amblyopia is evidenced by poor visual acuity in the eye resulting in poor visual performance. Normally, visual acuity improves during maturation. It is known that amblyopia may occur in humans from unknown causes or as pan of strabismus. It is possible that administration of therapeutically effective amounts and dosages of the instant muscarinic antagonist might prevent or inhibit the development of permanent or persistent amblyopia in maturing humans with decreased likelihood of sensitization of the eye. It is also possible that humans who have already developed amblyopia from other or even unknown causes might be aided by similar therapeutic treatment with the aforementioned agents.

The following examples are provided in order that this invention might be more fully understood; they are not to be construed as limitative of the invention. The compounds are characterized analytically using techniques such as nuclear magnetic resonance, mass spectrometry, chromatography and the like.

EXAMPLE 1

1,3-dihydro-1-{1-[1-(5-pyrimidine-carbonyl)piperidin-4-yl]piperidin-4-yl}-2H-benzimidazol-2-one Step 1: A mixture of 100 g 4-piperidone hydrochloride hydrate, 1 L ether, 300 mL of water, 500 mL of saturated aqueous $Na_2CO_3$ solution and 140 g di-t-butyldicarbonate was vigorously stirred for 5 days. The layers were separated and the aqueous layer was extracted with 500 mL of ether. The combined organic extracts were dried over $MgSO_4$ and concentrated under reduced pressure. The product N-t-butyloxycarbonyl-4-piperidone, 127 g, crystallized as a white solid.

Step 2: A mixture of 20.6 g N-t-butyloxycarbonyl-4-piperidone, 15 g of 4-(2-oxo-1-benzimidazolinyl)piperidine, 300 mL of 1,2-dichloroethane, 4.2 mL of glacial acetic acid and 24 g of sodium triacetoxyborohydride was stirred at room temperature for 48 h. The reaction mixture was poured into 500 mL chloroform and 500 mL saturated aqueous $Na_2CO_3$ and the layers separated. The aqueous layer was extracted with 2×250 mL of chloroform and the combined organic layers dried over $MgSO_4$ and concentrated under reduced pressure. Recrystallization of the crude product from 200 mL of ethyl acetate gave in two crops 28.7 g of pure 1,3-dihydro-1-{1-[1-(t-butyloxycarbonyl)piperidin-4-yl]piperidin-4-yl}-2H-benzimidazol-2-one as a white solid.

Step 3: A stirred solution of 4 g of 1,3-dihydro-1-{1-[1-(t-butyloxycarbonyl)piperidin-4-yl]piperidin-4-yl}-2H-benzimidazol-2-one in 150 mL of 1N HCl was heated to reflux for 4 h, cooled and concentrated to dryness. After drying overnight under vacuum, there was obtained 4.0 g of 1,3-dihydro-1-{1-[1-piperidin-4-yl]piperidin-4-yl}-2H-benzimidazol-2-one dihydrochloride salt as a white solid.

Step 4: To a stirred solution of 6 g of 1,3-dihydro-1-{1-[1-piperidin-4-yl]piperidin-4-yl}-2H-benzimidazol-2-one dihydrochloride salt and 20 mL of triethylamine in 500 mL of dichloromethane was added 3 g of pyrimidine-5-carboxylic acid chloride. After 2 h, 50 mL of dilute aqueous ammonia was added and the mixture stirred for an additional 30 min. The organic layer was separated, the aqueous layer extracted with two additional 200 mL portions of chloroform and the combined organic extracts dried over $MgSO_4$ and concentrated under reduced pressure. Recrystallization of the crude product from 200 mL of ethyl acetate gave in two crops 6 g of pure 1,3-dihydro-1-{1-[1-(5-pyrimidinecarbonyl)piperidin-4-yl]piperidin-4-yl}-2H-benzimidazol-2-one as a white solid: $_1$H NMR (400 MHz, $CDCl_3$) 10.4 (s, 1H), 9.28 (s, 1H), 8.82 (s, 2H), 7.4–6.9 (m, 4H), 4.8 (br m, 1H), 4.4 (br m, 1H), 3.8 (br m, 1H), 3.1 (br m, 4H), 2.88 (br m, 1H), 2.74 (br m, 1H), 2.44 (br m, 4H), 2.0 (br m, 1H), 1.88 (br m, 2H), 1.58 (br m, 2H). The dihydrochloride salt was recystallized from ethanol: Analysis calculated for $C_{22}H_{26}N_6O_2.2HCl.1.3\ C_2H_7O$ C: 54.79, H: 6.69, N: 15.58 found C: 54.85, H: 6.67, N: 15.55.

EXAMPLE 2

5-methyl-1,3-dihydro-1-{1-[1-(5-pyrimidine carbonyl)piperidin-4-yl]piperidin-4-yl}-2H-benzimidazol-2-one Step 1: A mixture of 69 g of 4-chloro-3-nitro-toluene, 50 g of ethyl 4-amino-1-piperidinecarboxylate, 24 g of sodium carbonate, 0.1 g of sodium iodide and 120 mL of cyclohexanol was heated to 150° C. for 72 h. After cooling the cyclohexanol was distilled off under reduced pressure and the residue partitioned between 1 L of ethyl acetate and 1 L of water. The organic extract was dried over $MgSO_4$ and concentrated under reduced pressure. Chromatography over silica gel, eluting with 20% ethyl acetate in cyclohexane gave 38.5 g (42.3%) of ethyl 4-(4-methyl-2-nitroanilino)-1-piperidinecarboxylate as an orange crystalline solid. $^1$H NMR (400 MHz, $CDCl_3$) 8.0 (s, 1H), 7.27 (t, J=9 Hz, 1H), 6.8 (d, J=9 Hz, 1H), 4.15 (q, J=7 Hz, 2H), 4.05 (br m, 2H), 3.67 (br m, 1H), 3.10 (br t, J=11 Hz, 2H), 2.27 (s, 3H), 2.06 (br d, J=11 Hz, 2H), 1.6 (m, 2H), 1.27 (t, J=7 Hz, 4H).

Step 2: A mixture of 8.23 g of ethyl 4-(4-methyl-2-nitroanilino)-1-piperidinecarboxylate, 200 mL of tetrahydrofuran, 225 mL of ethanol and 2 g of 5% platinum on carbon was stirred under an atmosphere of hydrogen for 7 h. The catalyst was filtered off and the filtrate concentrated to to a thick oil. To an ice cold, vigorously stirred solution of the resulting crude ethyl 4-(4-methyl-2-aminoanilino)-1-piperidinecarboxylate in 500 mL of ethyl acetate was added 500 mL of saturated sodium carbonate followed by 20 mL of 1.9M phosgene in toluene dropwise over 30 min. After stirring overnight at room temperature, the layers were separated and the organic layer dried over $MgSO_4$ and concentrated to dryness. Trituration of the residue with ether-hexane gave 8 g of ethyl 4-(5-methyl-2-oxo-1-benzimidazolinyl)piperidine-1-carboxylate as a white crystalline solid.

Step 3: A mixture of 5 g of ethyl 4-(5-methyl-2-oxo-1-benzimidazolinyl)piperidine-1-carboxylate and 20 mL of 2N NaOH was heated under reflux for 12 h. The resulting solution is cooled and stirred for for 30 minutes with 5 g of ammonium chloride and extracted with three 200 mL portions of chloroform. The combined organic extracts were dried over $MgSO_4$, concentrated under reduced pressure and triturated with ether. The solid product 4-(5-methyl-2-oxo-1-benzimidazolinyl)piperidine weighed 3.5 g after drying.

Step 4: A mixture of 4.5 g N-t-butyloxycarbonyl-4-piperidone, 4.7 g of 4-(5-methyl-2-oxo-1-benzimidazolinyl) piperidine, 65 mL of 1,2-dichloroethane, 1.3 mL of glacial acetic acid and 6.4 g of sodium triacetoxyborohydride was stirred at room temperature for 48 h. The reaction mixture was poured into 500 mL chloroform and 500 mL saturated aqueous $Na_2CO_3$ and the layers separated. The aqueous layer was extracted with 2×250 mL of chloroform and the combined organic layers dried over $MgSO_4$ and concentrated under reduced pressure. Recrystallization of the crude product from 50 mL of ethyl acetate gave in two crops 6.18 g of pure 5-methyl-1,3-dihydro-1-{1-[1-(t-butyloxycarbonyl)piperidin-4-yl]piperidin-4-yl}-2H-benzimidazol-2-one as a white solid: mp 210°–211° C.

Step 5: A stirred solution of 6.18 g of 5-methyl-1,3-dihydro-1-{1-[1-(t-butyloxycarbonyl)piperidin-4-yl]piperidin-4-yl}-2H-benzimidazol-2-one in 200 mL of 1N HCl was heated to reflux for 4 h, cooled and concentrated to dryness. After drying overnight under vacuum, there was obtained 6 g of 5-methyl-1,3-dihydro-1-{1-[1-piperidin-4-yl]piperidin-4-yl}-2H-benzimidazol-2-one dihydrochloride salt as a white solid.

Step 6: To a stirred solution of 6 g of 5-methyl-1,3-dihydro-1-{1-[1-piperidin-4-yl]piperidin-4-yl}-2H-benzimidazol-2-one dihydrochloride salt and 20 mL of triethylamine in 500 mL of dichloromethane was added 3 g of pyrimidine-5-carboxylic acid chloride. After 2 h, 50 mL of dilute aqueous ammonia was added and the mixture stirred for an additional 30 min. The organic layer was separated, the aqueous layer extracted with two additional 200 mL portions of chloroform and the combined organic extracts dried over $MgSO_4$ and concentrated under reduced pressure. Recrystallization of the crude product from 200 mL of ethyl acetate gave in two crops 6 g of pure 5-methyl-1,3-dihydro-1-{1-[1-(5-pyrimidinecarbonyl)piperidin-4-yl]piperidin-4-yl}-2H-benzimidazol-2-one as a white solid: $^1$H NMR (400 MHz, $CDCl_3$) 9.6 (br s, 1H), 9.28 (s, 1H), 8.82 (s, 2H), 7.14 (d, J=7.4 Hz, 1H), 6.93 (s, 1H), 6.84 (d, J=7.4 Hz, 1H), 4.8 (br m, 1H), 4.3 (br m, 1H), 3.8 (br m, 1H), 3.2 (br m, 1H), 3.1 (br m, 4H), 2.74 (br m, 1H), 2.41 (br m, 4H), 2.36 (s, 3H), 2.0 (br m, 1H), 1.88 (br m, 2H), 1.58 (br m, 2H). The dihydrochloride salt was recystallized from toluene-ethanol: Analysis calculated for $C_{23}H_{28}N_6O_2.2HCl.0.2\ C_7H_8.0.75\ H_2O$ C: 55.78, H: 6.35, N: 16.00 found C: 55.82, H: 6.61, N: 16.04.

EXAMPLE 3

1,3-dihydro-1-{1-[1-(2-pyrazinecarbonyl)piperidin-4-yl]piperidin-4-yl}-2H-benzimidazol-2-one To a stirred, ice cold solution of 25 mg of pyrazine-2-carboxylic acid and 0.11 mL of triethylamine in 5 mL of tetrahydrofuran was added 0.040 mL of diphenylphosphoryl chloride. After stirring for 1 h at 0° C., 100 mg 1,3-dihydro-1-{1-[1-piperidin-4-yl]piperidin-4-yl}-2H-benzimidazol-2-one dihydrochloride salt was added and the reagents were allowed to warm and stir overnight. The reaction mixture was diluted with 100 mL of chloroform and the resulting solution was washed with 10 mL of saturated $Na_2CO_3$, dried over $MgSO_4$ and concentrated under reduced pressure. Preparative thin layer chromatography on silica gel eluting with 90:10:5 $CHCl_3$:$CH_3OH$: conc. $NH_4OH$ gave 90 mg of 1,3-dihydro-1-{1-[1-(2-pyrazinecarbonyl)piperidin-4-yl]piperidin-4-yl}-2H-benzimidazol-2-one as a white solid: $^1H$ NMR (400 MHz, $CDCl_3$) 10.0 (s, 1H), 8.94 (s, 1H), 8.65 (s, 1H), 8.57 (s, 1H), 7.3–6.9 (m, 4H), 4.8 (br d, J=12.5 Hz, 1H), 4.4 (br m, 1H), 4.0 (br d, J=12.5 Hz, 1H), 3.1 (br m, 4H), 2.88 (br m, 1H), 2.71 (br m, 1H), 2.47 (br m, 4H), 2.0 (br d, J=12 Hz, 1H), 1.88 (br m, 2H), 1.68 (br t, J=12 Hz, 2H). The dihydrochloride salt was recystallized from ethanol: Analysis calculated for $C_{22}H_{26}N_6O_2 \cdot 2HCl \cdot 0.5\ C_2H_7O$ C: 59.28, H: 6.49, N: 18.04 found C: 59.18, H: 6.36, N: 17.99.

EXAMPLE 4

1,3-dihydro-1-{1-[1-(3-pyridinecarbonyl)piperidin-4-yl]piperidin-4-yl}-2H-benzimidazol-2-one From 1,3-dihydro-1-{1-[1-piperidin-4-yl]piperidin-4-yl}-2H-benzimidazol-2-one dihydrochloride salt and nicotinoylchloride hydrochloride using the procedure described for Example 1, Step 4 there was obtained 1,3-dihydro-1-{1-[1-(3-pyridinecarbonyl)piperidin-4-yl]piperidin-4-yl}-2H-benzimidazol-2-one as a white solid: $^1H$ NMR (400 MHz, $CDCl_3$) 9.8 (s, 1H), 8.68 (m, 2H), 7.77 (m, 1H), 7.37 (m, 1H), 7.27 (m, 1H), 7.12–7.0 (m, 3H), 4.8 (br m, 1H), 4.38 (br m, 1H), 3.8 (br m, 1H), 3.1 (br m, 4H), 2.88 (br m, 1H), 2.65 (br m, 1H), 2.44 (br m, 4H), 2.0 (br m, 1H), 1.88 (br m, 2H), 1.60 (br m, 2H). The dihydrochloride salt was recystallized from ethanol: Analysis calculated for $C_{23}H_{27}N_5O_2 \cdot 2HCl \cdot 0.5\ C_2H_7O$ C: 57.32, H: 6.43, N: 13.97 found C: 57.32, H: 6.57, N: 13.77.

EXAMPLE 5

5-methyl-1,3-dihydro-1-{1-[1-(3-pyridine carbonyl)piperidin-4-yl]piperidin-4-yl}-2H-benzimidazol-2-one From 5-methyl-1,3-dihydro-1-{1-[1-piperidin-4-yl]piperidin-4-yl}-2H-benzimidazol-2-one dihydrochloride salt and nicotinoylchloride hydrochloride using the procedure described for Example 1, Step 4 there was obtained 5-methyl-1,3-dihydro-1-{1-[1-(3-pyridinecarbonyl)piperidin-4-yl]piperidin-4-yl}-2H-benzimidazol-2-one as a white solid: $^1H$ NMR (400 MHz, $CDCl_3$) 9.45 (s, 1H), 8.68 (m, 2H), 7.77 (m, 1H), 7.37 (m, 1H), 7.14 (d, J=7.4 Hz, 1H), 6.93 (s, 1H), 6.84 (d, J=7.4 Hz, 1H), 4.8 (br m, 1H), 4.38 (br m, 1H), 3.8 (br m, 1H), 3.1 (br m, 4H), 2.88 (br m, 1H), 2.65 (br m, 1H), 2.44 (br m, 4H), 2.38 (s, 3H), 2.0 (br m, 1H), 1.88 (br m, 2H), 1.60 (br m, 2H). Analysis calculated for $C_{24}H_{29}N_5O_2 \cdot 0.5 CH_2Cl_2 \cdot 0.8\ CH_3CO_2CH_2CH_3$ C: 64.91, H: 7.12, N: 13.81 found C: 65.04, H: 7.10, N: 13.52.

EXAMPLE 6 trans-1,3-Dihydro-1-{4-[4-(5-pyrimidinecarbonyl)piperazin-1-yl]-1-cyclohexyl}-2H-benzimidazol-2-one Step 1: A mixture of 10 g of 1,4-cyclohexanedione mono-ethyleneketal, 13.8 g of 1,2-phenylenediamine, 180 mL of 1,2-dichloroethane, 4 mL of glacial acetic acid and 19 g of sodium triacetoxyborohydride was stirred at room temperature for 48 h. The reaction mixture was poured into 200 mL chloroform and 200 mL saturated 1N NaOH and the layers separated. The aqueous layer was extracted with 2×50 mL of chloroform and the combined organic layers dried over $MgSO_4$ and concentrated to dryness under reduced pressure. To an ice cold, vigorously stirred solution of the resulting crude 4-(2-aminoanilino)cyclohexan-1-one ethylene ketal in 200 mL of ethyl acetate was added 200 mL of saturated sodium carbonate followed by 10 mL of 1.9M phosgene in toluene dropwise over 30 min. After stirring overnight at room temperature, the layers were separated and the organic layer dried over $MgSO_4$ and concentrated to dryness. Chromatography over silica gel, eluting with 5% methanol in dichloromethane gave 7 g of the ethylene ketal of 1,3-dihydro-1-(4-oxocyclohexyl)-2H-benzimidazol-2-one as a solid. $^1H$ NMR (400 MHz, $CDCl_3$) 9.58 (s, 1H), 7.28 (m, 1H), 7.07–7.15 (m, 3H), 4.5 (m, 1H), 4.03 (m, 4H), 2.5 (m, 2H), 1.8–1.93 (m, 6H).

Step 2: A mixture of 7 g of the ethylene ketal of 1,3-dihydro-1-(4-oxocyclohexyl)-2H-benzimidazol-2-one, 100 mL of glacial acetic acid, 50 mL of water and 50 mL of conc. HCl was heated under reflux for 12 h. The mixture was concentrated under reduced pressure, diluted with 100 mL of water and extracted into 3×200 mL of $CHCl_3$. The combined organic extracts were washed with 100 mL of water, 100 mL of saturated $Na_2CO_3$, dried over $MgSO_4$ and concentrated under reduced pressure. Drying under vacuum gave 5 g of 1,3-dihydro-1-(4-oxocyclohexyl)-2H-benzimidazol-2-one as a tan solid: $^1H$ NMR (400 MHz, $CDCl_3$) 9.52 (s, 1H), 7.14–7.03 (m, 4H), 4.82 (m, 1H), 2.8–2.6 (m, 4H), 2.2 (m, 2H).

Step 3: A mixture of 1.5 g of 1,3-dihydro-1-(4-oxocyclohexyl)-2H-benzimidazol-2-one, 1.21 g of tert-butyl-1-piperazinecarboxylate, 20 mL of 1,2-dichloroethane, 0.4 mL of acetic acid and 1.8 g of sodium triacetoxyborohydride was stirred at room temperature for 48 h. The reaction mixture was poured into 500 mL chloroform and 500 mL saturated aqueous $Na_2CO_3$ and the layers separated. The aqueous layer was extracted with 2×250 mL of chloroform and the combined organic layers dried over $MgSO_4$ and concentrated under reduced pressure. Chromatography of the crude product on silica gel, eluting with 90:10 $CHCl_3$: MeOH gave 0.631 g of cis-1,3-dihydro-1-{4-[4-(tert-butyloxycarbonyl)piperazin-1-yl]-1-cyclohexyl}-2H-benzimidazol-2-one as white solid: mp=228°–30° C.; $^1H$ NMR (400 MHz, $CDCl_3$) 7.45 (m, 1H), 7.14 (m, 1H), 7.05 (m, 2H), 3.55 (br s, 4H), 2.49 (br s, 6H), 2.27 (s, 1H), 2.15 (br d, J=15.1, 2H), 1.58 (br d, J=10.6, 4H), 1.49 (s, 9H); followed by 0.52 g of trans-1,3-dihydro-1-{4-[4-(tert-butyloxycarbonyl)piperazin-1-yl]-1-cyclohexyl}-2H-benzimidazol-2-one as white solid: mp=195°–6° C.; $^1H$ NMR (400 MHz, $CDCl_3$) 7.14 (m, 2H), 7.12–7.04 (m, 2H), 4.28 (m, 1H), 3.46 (br s, 4H), 2.56 (br s, 5H), 2.49 (m, 1H), 2.29 (q, 2H), 2.06 (d, J=6.4, 2H), 2.0 (d, J=9, 2H), 1.52 (m, 1H), 1.47 (s, 9H).

Step 4: A stirred solution of 0.52 g of trans-1,3-dihydro-1-{4-[4-(tert-butyloxycarbonyl)piperazin-1-yl]-1-cyclohexyl}-2H-benzimidazol-2-one in 15 mL of 1N HCl was heated to reflux for 1 h, cooled, basified to pH 10 with 6N NaOH and extracted 2×50 mL of $CHCl_3$. The combined extracts were dried over $MgSO_4$ and concentrated under reduced pressure. After drying overnight under vacuum, there was obtained 0.28 g of trans-1,3-dihydro-1-{4-(1-piperazinyl)-1-cyclohexyl}-2H-benzimidazol-2-one as a white solid: $^1H$ NMR (400 MHz, $CDCl_3$) 7.14 (m, 1H), 7.11 (m, 1H), 7.07 (m, 2H), 4.28 (m, 1H), 2.61 (s, 4H), 2.45 (t, 1H), 2.26 (q, 2H), 2.10 (d, J=12.2, 2H), 2.0 (d, J=10.8, 2H), 1.53 (q, 2H).

Step 5: To a stirred solution of 0.044 g of trans-1,3-dihydro-1-{4-(1-piperazinyl)-1-cyclohexyl}-2H-benzimidazol-2-one and 20 mL of triethylamine in 3 mL of dichloromethane was added 0.03 g of pyrimidine-5-carboxylic acid chloride. After 2 h, 5 mL of dilute aqueous ammonia was added and the mixture stirred for an additional 30 min. The organic layer was separated, the aqueous layer extracted with two additional 20 mL portions of chloroform and the combined organic extracts dried over $MgSO_4$ and concentrated under reduced pressure. Chromatography over silica gel eluting with 90:10 EtOAc: MeOH gave 0.030 g of trans-1,3-dihydro-1-{4-[4-(5-pyrimidinecarbonyl) piperazin-1-yl]-1-cyclohexyl}-2H-benzimidazol-2-one as a white solid: mp>250° C.; $^1$H NMR (400 MHz, $CDCl_3$) 9.76 (bs 1H), 9.27 (s, 1H), 8.83 (s, 2H), 7.27–7.04 (m, 4H), 4.27 (br t, 1H), 3.84 (br s, 2H), 3.43 (br s, 2H), 2.73 (br s, 1H), 2.61 (br s, 2H), 2.54 (d, 1H), 2.34 (q, 2H), 2.02 (br t, 3H), 1.97 (br s, 1H), 1.52 (q, 2H). The dihydrochloride salt was recystallized from ethanol: Analysis calculated for $C_{22}H_{26}N_6O_2$·2HCl·0.65 $CHCl_3$ C: 48.84, H: 5.18, N: 15.09; found C: 48.85, H: 5.36, N: 14.72.

EXAMPLE 7

1,3-dihydro-1-{trans-4-[4-(5-pyridinecarbonylamino) piperidin-1-yl]-1-cyclohexyl}-2H-benzimidazol-2-one Step 1: To a stirred solution of 2.0 g of ethyl 4-amino-1-piperidinecarboxylate and 2 mL of triethylamine in 50 mL of chloroform was added 2.07 g of nicotinoyl chloride hydrochloride. After 12 h, the mixture was washed with 50 mL of saturated sodium bicarbonate, dried over $MgSO_4$ and concentrated under reduced pressure. Drying under vacuum gave 2.2 g of 4-(3-pyridinecarbonylamino)-1-piperidinecarboxylate as a white solid.

Step 2: A mixture of 1.2 g of the ethylene ketal of 4-(3-pyridinecarbonylamino)-1-piperidinecarboxylate and 20 mL of 6N HCl was heated under reflux for 6 h. The mixture was cooled, extracted with 20 mL of dichloromethane, then basified with 6N NaOH and extracted with 3×50 mL of chloroform. The combined chloroform extracts were dried over $MgSO_4$ and concentrated under reduced pressure. Drying under vacuum gave 0.6 g of 4-(3-pyridinecarbonylamino)piperidine as an oil: $^1$H NMR (400 MHz, $CDCl_3$) 8.96 (d, J=2 Hz, 1H), 8.72 (m, 1H), 8.10 (m, 1H), 7.40 (m, 2H).

Step 3: A mixture of 0.13 g of 1,3-dihydro-1-(4-oxocyclohexyl)-2H-benzimidazol-2-one, 0.12 g of 4-(3-pyridinecarbonylamino)piperidine, 5 mL of 1,2-dichloroethane, 0.04 mL of glacial acetic acid and 0.161 g of sodium triacetoxyborohydride was stirred at room temperature for 48 h. The reaction mixture was poured into 50 mL chloroform and 50 mL saturated aqueous $Na_2CO_3$ and the layers separated. The aqueous layer was extracted with 2×25 mL of chloroform and the combined organic layers dried over $MgSO_4$ and concentrated under reduced pressure. Chromatography of the crude product on silica gel, eluting with 10% methanol in chloroform gave 0.015 g of 1,3-dihydro-1-{trans-4-[4-(5-pyridinecarbonylamino)piperidin-1-yl]-1-cyclohexyl}-2H-benzimidazol-2-one: $^1$H NMR (400 MHz, $CDCl_3$) 9.01 (d, J=2 Hz, 1H), 8.75 (dd, J=2 and 4.5 Hz, 1H), 8.40 (br s, 1H), 8.16 (dd, J=2 and 8 Hz, 1H), 7.43 (m, 2H), 7.08 (m, 3H), 6.16 (br m, 1H), 4.47 (m, 1H), 4.12 (m, 2H), 3.1 (br s, 2H), 2.8 (m, 1H), 2.5 (m, 1H), 2.2 (br m, 4H), 1.60 (br m, 8H). The dihydrochloride salt was precipitated from ether: Analysis calculated for $C_{24}H_{29}N_5O_2$·2HCl·0.75 $CHCl_3$·1.0 $H_2O$ C: 49.54, H: 5.67, N: 11.67 found C: 49.55, H: 5.85, N: 11.88.

EXAMPLE 8

1,3-dihydro-1-{1-[1-(3-pyridinemethyl)piperidin-4-yl] piperidin-4-yl}-2H-benzimidazol-2-one A mixture of 0.10 g of 1,3-dihydro-1-{1-[1-piperidin-4-yl]piperidin-4-yl}-2H-benzimidazol-2-one, 0.037 mL of 3-pyridinecarboxaldehyde, 15 mL of 1,2-dichloroethane, 0.10 mL of glacial acetic acid and 0.106 g of sodium triacetoxyborohydride was stirred at room temperature for 24 h. The reaction mixture was poured into 10 mL dichloromethane and 10 mL saturated aqueous $NaHCO_3$ and the layers separated. The aqueous layer was extracted with 2×10 mL of dichloromethane and the combined organic layers dried over $MgSO_4$ and concentrated under reduced pressure. Preparative thin layer chromatography on silica gel, eluting with 10% methanol in chloroform gave 0.050 g of 1,3-dihydro-1-{1-[1-(3-pyridinemethyl)piperidin-4-yl] piperidin-4-yl}-2H-benzimidazol-2-one as a white solid: $^1$H NMR (400 MHz, $CDCl_3$) 9.9 (s, 1H), 8.55 (m, 2H), 7.65 (m, 1H), 7.35–7.25 (m, 2H), 7.15–7.05 (m, 3H), 4.38 (br m, 1H), 3.5 (s, 2H), 3.1 (br m, 2H), 2.88 (br m, 2H), 2.44 (m, 4H), 2.2 (m, 1H), 2.05 (br t, 2H), 1.83 (br m, 4H), 1.62 (br m, 2H): Analysis calculated for $C_{23}H_{29}N_5O$·0.45 $CHCl_3$ C: 63.25, H: 6.67, N: 15.73 found C: 62.96, H: 6.74, N: 15.54.

EXAMPLE 9

1,3-dihydro-1-{1-[1-(3-pyridylmethylaminocarbonyl) piperidin-4-yl]piperidin-4-yl}-2H-benzimidazol-2-one Step 1: To a stirred solution of 0.108 g of 3-aminomethylpyridine and 0.280 g of di-2-pyridylcarbonate in 5 mL of dichloromethane was added 0.209 mL of triethylamine. After 12 h, the mixture was diluted with 50 mL of dichloromethane and washed with 50 mL of saturated sodium bicarbonate, dried over $MgSO_4$ and concentrated under reduced pressure. The residue was filtered through a short column of silica gel, eluting with ethyl acetate (100 mL) and the eluate concentrated to dryness. Drying under vacuum gave 0.20 g of N-(3-pyridylmethyl)-O-2-pyridylurethane as a white solid.

Step 2: A mixture of 0.108 g of 1,3-dihydro-1-{1-[1-piperidin-4-yl]piperidin-4-yl}-2H-benzimidazol-2-one, 0.070 g of N-(3-pyridylmethyl)-O-2-pyridylurethane and 0.062 mL of triethylamine in 5 mL of dichloromethane was added 2.07 g of nicotinoyl chloride hydrochloride. After 12 h, the mixture was washed with 10 mL of saturated sodium bicarbonate, dried over $MgSO_4$ and concentrated under reduced pressure. Preparative thin layer chromatography on silica gel, eluting with 5% methanol in chloroform containing 2% conc. $NH_4OH$ gave 0.113 g of 1,3-dihydro-1-{1-[1-(3-pyridylmethylaminocarbonyl)piperidin-4-yl]piperidin-4-yl}-2H-benzimidazol-2-one: $^1$H NMR (400 MHz, $CDCl_3$) 9.85 (s, 1H), 2H-benzimidazol-1H), 8.55 (dd, 1H), 7.7 (m, 1H), 7.27 (m, 1H), 7.15–7.05 (m, 3H), 4.98 (m, 1H), 4.45 (m, 2H), 4.38 (m, 1H), 4.05 (br d, 2H), 3.15 (d, 2H), 2.85 (t, 2H), 2.55 (br m, 1H), 2.42 (br m, 4H), 2.22 (m, 4H), 1.55 (m, 2H): Analysis calculated for $C_{24}H_{30}N_6O_2$·0.65 $CHCl_3$ C: 57.81, H: 6.03, N: 16.41 found C: 57.56, H: 6.08, N: 16.75.

EXAMPLE 10

1,3-dihydro-1-{1-[1-(3-pyridylmethyloxycarbonyl) piperidin-4-yl]piperidin-4-yl}-2H-benzimidazol-2-one A mixture of 2.0 g of 1,3-dihydro-1-{1-[1-piperidin-4-yl] piperidin-4-yl}-2H-benzimidazol-2-one dihydrochloride, 1.48 g of 3-pyridylmethyl 4-nitrophenyl carbonate and 4.45 mL of triethylamine in 20 mL of tetrahydrofuran was stirred for 12 h. The mixture was diluted with 100 mL of chloroform, washed with 20 mL of 1N NaOH, dried over MgSO$_4$ and concentrated under reduced pressure. Drying under vacuum gave 0.20 g of 1,3-dihydro-1-{1-[1-(3-pyridylmethyloxycarbonyl)piperidin-4-yl]piperidin-4-yl}-2H-benzimidazol-2-one as a white solid: $^1$H NMR (400 MHz, CDCl$_3$) 9.12 (s, 1H), 8.64 (m, 1H), 8.58 (m, 1H), 7.7 (m, 1H), 7.27 (m, 1H), 7.15–7.05 (m, 3H), 5.2 (s, 1H), 4.3 (m, 3H), 3.06 (m, 2H), 2.80 (br s, 2H), 2.5 (m, 1H), 2.45 (m, 4H), 1.84 (m, 4H), 1.5 (m, 2H). The dihydrochloride salt was crystallized from isopropanol: Analysis calculated for C$_{24}$H$_{30}$N$_6$O$_2$.2HCl.1.5 H$_2$O.0.6(CH$_3$)$_2$CHOH C: 57.81, H: 6.03, N: 16.41 found C: 57.56, H: 6.08, N: 16.75.

EXAMPLE 11

1,3-dihydro-1-{trans-4-[4-(5-pyrimidinecarbonylypiperazin-1-yl]-1-cyclohexyl}-2H-benzimidazol-2-one Step 1: A mixture of 1.5 g of 1,3-dihydro-1-(4-oxocyclohexyl)-2H-benzimidazol-2-one, 1.21 g of tert-butyl 1-piperazinecarboxylate, 20 mL of 1,2-dichloroethane, 0.40 mL of glacial acetic acid and 1.79 g of sodium triacetoxyborohydride was stirred at room temperature for 48 h. The reaction mixture was poured into 50 mL chloroform and 50 mL saturated aqueous Na$_2$CO$_3$ and the layers separated. The aqueous layer was extracted with 2×25 mL of chloroform and the combined organic layers dried over MgSO$_4$ and concentrated under reduced pressure. Chromatography of the crude product on silica gel, eluting with 10% methanol in chloroform gave, firstly, 0.63 g of 1,3-dihydro-1-{cis-4-[4-(tert-butylcarbonyl)piperazin-1-yl]-1-cyclohexyl}-2H-benzimidazol-2-one: $^1$H NMR (400 MHz, CDCl$_3$) 7.47 (m, 1H), 7.25 (m, 1H), 7.05 (m, 2H), 4.55 (m, 1H), 3.54 (m, 4H), 2.49 (m, 6H), 2.27 (s, 0.8H), 2.15 (d, 2H), 1.97 (m, 0.2H), 1.57 (m, 4H), 1.49 (s, 9H). Later fractions gave 1,3-dihydro-1-{trans-4-[4-(tert-butylcarbonyl)piperazin-1-yl]-1-cyclohexyl}-2H-benzimidazol-2-one: $^1$H NMR (400 MHz, CDCl$_3$) 7.15 (m, 2H), 7.06 (m, 2H), 4.28 (m, 1H), 3.46 (m, 4H), 2.56 (m, 4H), 2.5 (m, 1H), 2.26 (m, 2H), 2.03 (m, 6H), 1.47 (s, 9H).

Step 2: A stirred solution of 0.52 g of 1,3-dihydro-1-{trans-4-[4-(tert-butylcarbonyl)piperazin-1-yl]-1-cyclohexyl}-2H-benzimidazol-2-one in 15 mL of 1N HCl was heated to reflux for 1 h, cooled and basified with 6N NaOH. The basic mixture was extracted with 2×50 mL portions of chloroform. The combined organic extracts were dried over MgSO$_4$ and concentrated under reduced pressure. After drying overnight under vacuum, there was obtained 0.28 g of 1,3-dihydro-1-{trans-4-[1-piperazinyl]-1-cyclohexyl}-2H-benzimidazol-2-one as a white solid: $^1$H NMR (400 MHz, CDCl$_3$) 7.16–7.03 (m, 4H), 4.27 (m, 1H), 2.94 (m, 4H), 2.61 (m, 4H), 2.25 (m, 2H), 2.1 (d, 2H), 1.97 (d, 2H), 1.54 (m, 2H).

Step 3: To a stirred solution of 0.044 g of 1,3-dihydro-1-{trans-4-[1-piperazinyl]-1-cyclohexyl}-2H-benzimidazol-2-one and 0.2 mL of triethylamine in 3 mL of dichloromethane was added 0.030 g of pyrimidine-5-carboxylic acid chloride. After 2 h, 5 mL of dilute aqueous ammonia was added and the mixture stirred for an additional 30 min. The organic layer was separated, the aqueous layer extracted with two additional 20 mL portions of chloroform and the combined organic extracts dried over MgSO$_4$ and concentrated under reduced pressure. Chromatography over silica gel eluting with 10% methanol in ethyl acetate gave 0.030 g of 1,3-dihydro-1-{trans-4-[4-(5-pyrimidinecarbonyl)piperazin-1-yl]-1-cyclohexyl}-2H-benzimidazol-2-one as a white solid: $^1$H NMR (400 MHz, CDCl$_3$) 9.76 (s, 1H), 9.29 (s, 1H), 8.83 (s, 2H), 7.16–7.04 (m, 4H), 4.27 (m, 1H), 3.84 (s, 2H), 3.48 (s, 2H), 2.72 (s, 2H), 2.61 (s, 2H), 2.56 (m, 1H), 2.30 (q, 2H), 2.05 (m, 4H), 1.86 (br s, 1H), 1.5 (q, 2H). The dihydrochloride salt was precipitated from chloroform/ethyl acetate: Analysis calculated for C$_{22}$H$_{26}$N$_6$O$_2$.2HCl.0.65 CHCl$_3$ C: 48.84, H: 5.18, N: 15.09 found C: 48.85, H: 5.36, N: 14.72.

EXAMPLE 12

1,3-dihydro-1-{trans-4-[4-(3-pyridinecarbonyl)piperazin-1-yl]-1-cyclohexyl}-2H-benzimidazol-2-one From 1,3-dihydro-1-{trans-4-[1-piperazinyl]-1-cyclohexyl}-2H-benzimidazol-2-one and nicotinoylchloride hydrochloride using the procedure described for Example 11, Step 3 there was obtained 1,3-dihydro-1-{trans-4-[4-(3-pyridinecarbonyl)piperazin-1-yl]-1-cyclohexyl}-2H-benzimidazol-2-one as a white solid: $^1$H NMR (400 MHz, CDCl$_3$) 9.51 (s, 1H), 8.68 (s, 2H), 7.77 (m, 1H), 7.38 (m, 1H), 7.12–7.04 (m, 4H), 4.26 (m, 1H), 3.83 (s, 2H), 3.47 (s, 2H), 2.71 (s, 2H), 2.58 (s, 2H), 2.53 (m, 2H), 2.30 (q, 2H), 2.0 (q, 4H), 1.53 (m, 2H), 1.26 (m, 2H). The hydrochloride salt was precipitated from chloroform/toluene: Analysis calculated for C$_{23}$H$_{27}$N$_5$O$_2$.HCl.0.20 CHCl$_3$.0.45 CH$_3$C$_6$H$_5$ C: 57.99, H: 6.43, N: 12.83 found C: 58.04, H: 6.36, N: 12.75.

EXAMPLE 13

1,3-dihydro-1-{trans-4-[1-(3-pyridinecarbonyl)-4-piperidinylamino]-1-cyclohexyl}-2H-benzimidazol-2-one Step 1: A mixture of 1.5 g of 1,3-dihydro-1-(4-oxocyclohexyl)-2H-benzimidazol-2-one, 1.12 g of ethyl 4-amino-1-piperidinecarboxylate, 20 mL of 1,2-dichloroethane, 0.40 mL of glacial acetic acid and 1.79 g of sodium triacetoxyborohydride was stirred at room temperature for 48 h. The reaction mixture was poured into 50 mL chloroform and 50 mL saturated aqueous Na$_2$CO$_3$ and the layers separated. The aqueous layer was extracted with 2×25 mL of chloroform and the combined organic layers dried over MgSO$_4$ and concentrated under reduced pressure. Chromatography of the crude product on silica gel, eluting with 10% methanol in ethyl acetate gave 1.3 g of 1,3-dihydro-1-{trans-4-[1-ethoxycarbonyl-4-piperidinylamino]-1-cyclohexyl}-2H-benzimidazol-2-one as a white solid: $^1$H NMR (400 MHz, CDCl$_3$) 9.8–9.9 (br m, 1H), 7.30 (m, 1H), 7.11–7.02 (m, 4H), 4.37 (m, 1H), 4.17–4.06 (m, 4H), 3.15 (m, 1H), 2.88 (t, 2H), 2.7 (m, 1H), 2.55 (m, 2H), 1.97 (d, 2H), 1.86 (d, 2H), 1.65 (q, 4H), 1.25 (m, 5H). Analysis calculated for C$_{21}$H$_{30}$N$_4$O$_3$ C: 65.26, H: 7.82, N: 14.46 found C: 65.20, H: 7.57, N: 14.15.

Step 2: A stirred solution of 1.2 g of 1,3-dihydro-1-{trans-4-[1-ethoxycarbonyl-4-piperidinylamino]-1-cyclohexyl}-2H-benzimidazol-2-one in 20 mL of 6N HCl was heated to reflux for 12 h, cooled and basified with 6N NaOH. The basic mixture was extracted with 2×50 mL portions of chloroform. The combined organic extracts were dried over MgSO$_4$ and concentrated under reduced pressure. After drying overnight under vacuum, there was obtained 0.51 g of 1,3-dihydro-1-{trans-4-[4-piperidinylamino]-1-cyclohexyl}-2H-benzimidazol-2-one as a white solid: $^1$H NMR (400 MHz, CDCl$_3$) 7.33 (m, 1H), 7.11 (m, 1H), 7.04 (m, 2H), 4.37 (m, 1H), 3.16 (m, 3H), 2.61–2.52 (m, 5H), 2.0 (d, 2H), 1.86 (d, 2H), 1.64 (m, 4H), 1.3 (m, 2H).

Step 3: To a stirred solution of 0.050 g of 1,3-dihydro-1-{trans-4-[4-piperidinylamino]-1-cyclohexyl}-2H-benzimidazol-2-one and 0.023 mL of triethylamine in 1.5mL of dichloromethane was added 0.024 g of nicotinoyl chloride hydrochloride. After 12 h, 20 mL of saturated sodium carbonate was added, the organic layer was separated, and the aqueous layer extracted with two additional 20 mL portions of chloroform. The combined organic extracts dried over $MgSO_4$ and concentrated under reduced pressure. Chromatography over silica gel eluting with 10% methanol/ 10% conc. $NH_4OH$ in chloroform gave 0.024 g of 1,3-dihydro-1-{trans-4-[1-(3-pyridinecarbonyl)-4-piperidinylamino]-1-cyclohexyl}-2H-benzimidazol-2-one as a white solid: $^1H$ NMR (400 MHz, $CDCl_3$) 9.04 (s, 1H), 8.68 (dd, 2H), 7.77 (m, 1H), 7.38 (m, 1H), 7.26 (m, 1H), 7.06 (m, 3H), 4.67 (br s, 1H), 3.75 (br s, 1H), 3.18 (br s, 2H), 2.99 (br s, 1H), 2.87 (br s, 1H), 2.55 (q, 2H), 2.13–1.9 (m, 4 H), 1.72–1.3 (m, 7H). The dihydrochloride salt was precipitated from chloroform/ethyl acetate: Analysis calculated for $C_{24}H_{29}N_5O_2.2HCl.0.90$ $CHCl_3.0.25$ $CH_3CO_2CH_2CH_3$ C: 50.02, H: 5.95, N: 11.26 found C: 51.28, H: 5.49, N: 11.53.

EXAMPLE 14

1,3-Dihydro-1-{1-[trans-4-(3-pyridinecarbonylamino) cyclohexyl]piperidin-4-yl}-2H-benzimidazol-2-one and 1,3-Dihydro-1-{1-[cis-4-(3-pyridinecarbonylamino) cyclohexyl]piperidin-4-yl}-2H-benzimidazol-2-one Step 1: A mixture of trans-4-aminocyclohexanol hydrochloride (3.0 g), saturated aqueous $Na_2CO_3$ (24 mL) and water (40 mL) was adjusted to pH 11.5 with 1N aqueous NaOH, and di-tert-butyldicarbonate (4.75 g) in tetrahydrofuran (30 mL) was added dropwise. The resulting mixture was stirred at room temperature for 3 h, then extracted with ethyl acetate (2×90 mL). The combined organic extracts were dried over $MgSO_4$ and concentrated under reduced pressure. Drying under vacuum gave the desired product, N-tert-butyloxycarbonyl-trans-4-aminocyclohexanol (4.2 g) as a colorless solid.

Step 2: To a stirred solution of oxalyl chloride (0.83 g) in dry dichloromethane (15 mL) at −60° C. was added dimethylsulfoxide (1.0 mL) in dichloromethane (3 mL) dropwise. The reaction mixture was stirred at −60° C. for 10 min, then N-tert-butyloxycarbonyl-trans-4-aminocyclohexanol (1.28 g) in dichloromethane (70 mL) was added over 15 min. The resulting mixture was stirred at −60° C. for a further 15 min, then triethylamine (4.2 mL) was added and the solution was allowed to warm to room temperature. The mixture was washed with water (20 mL) and this aqueous layer was extracted once with dichloromethane (20 mL). The combined organic extracts were dried over $MgSO_4$ and concentrated under reduced pressure. Drying under vacuum gave N-tert-butyloxycarbonyl-4-aminocyclohexanone (1.25 g) as a colorless solid.

Step 3: A mixture of N-tert-butyloxycarbonyl-4-aminocyclohexanone (1.32 g), 4-(2-keto-1-benzimidazolinyl)piperidine (1.48 g), sodium triacetoxyborohydride (1.97 g), acetic acid (0.35 mL), 1,2-dichloroethane (50 mL) and tetrahydrofuran (60 mL) was stirred at room temperature for 3 days. Saturated aqueous $Na_2CO_3$ (30 mL) and $H_2O$ (30 mL) were added and the mixture was extracted with dichloromethane (2×100 mL). The combined organic extracts were concentrated to dryness under reduced pressure. Column chromatography on silica gel, eluting with dichloromethane-10% methanol-1% $NH_4OH$ gave a mixture of the expected product isomers: 1,3-dihydro-1-{1-[trans-4-(tert-butyloxycarbonylamino) cyclohexyl]piperidin-4-yl}-2H-benzimidazol-2-one and 1,3-dihydro-1-{1-[cis-4-(tert-butyloxycarbonylamino) cyclohexyl]piperidin-4-yl}-2H-benzimidazol-2-one as a colorless solid (1.9 g).

Step 4: The mixture of cis and trans isomers isolated in Step 3 (0.85 g) was stirred in ethyl acetate (100 mL) at 0° C. and gaseous HCl was bubbled in until the mixture was saturated with the acid. Stirring was continued for 20 min, then the reaction mixture was concentrated in vacuo. The residue was dissolved in chloroform, washed with saturated aqueous $Na_2CO_3$, and the organic layer was dried over $MgSO_4$ and evaporated under reduced pressure. The residue was a crude sample of the two isomers: 1,3-dihydro-1-{1-[trans-4-aminocyclohexyl]piperidin-4-yl}-2H-benzimidazol-2-one and 1,3-dihydro-1-{1-[cis-4-aminocyclohexyl]piperidin-4-yl}-2H-benzimidazol-2-one (ratio≈4:1 from $^1H$ NMR spectrum) (0.40 g).

Step 5: To the mixture of cis and trans isomers isolated in Step 4 (90 mg) was added tetrahydrofuran (3 mL), dimethylformamide (2 mL), triethylamine (0.12 mL) and nicotinoyl chloride hydrochloride (76 mg). The reaction mixture was stirred at room temperature for 18 h then concentrated to dryness under reduced pressure. Preparative thin layer chromatography on silica gel, eluting with dichloromethane-10% methanol-1% $NH_4OH$ gave the desired product, 1,3-dihydro-1-{1-[trans-4-(3-pyridinecarbonylamino) cyclohexyl]piperidin-4-yl}-2H-benzimidazol-2-one (72 mg): $^1H$ NMR (400 MHz, $CDCl_3/CD_3OD$) 8.99 (m, 1H), 8.65 (d, J=5 Hz, 1H), 8.23 (d, J=8 Hz, 1H), 7.47 (dd, J=8,5 Hz, 1H), 7.42 (m, 1H), 7.07 (m, 3H), 4.35 (br m, 1H), 3.92 (tt, J=11,4 Hz, 1H), 3.13 (d, J=7 Hz, 2H), 2.51 (m, 5H), 2.16 (d, J=12 Hz, 2H), 2.05 (d, J=12 Hz, 2H), 1.85 (br m, 2H), 1.49 (m, 4H). HPLC purity (214 nm)=99%. The dihydrochloride salt was recrystallized from ethanol/chloroform; analysis calculated for $C_{24}H_{29}N_5O_2.2HCl.0.35$ $C_2H_6O.0.20$ $CHCl_3$: C:56.17, H:6.30, N: 13.15, found: C:56.36, H:6.18, N:13.14.

Also obtained was the cis isomer, 1,3-dihydro-1-{1-[cis-4-(3-pyridinecarbonylamino)cyclohexyl]piperidin-4-yl}-2H-benzimidazol-2-one (13 mg): $^1H$ NMR (400 MHz, $CDCl_3/CD_3OD$) 8.99 (m, 1H), 8.67 (d, J=5 Hz, 1H), 8.22 (d, J=8 Hz, 1H), 7.47 (dd, J=8,5 Hz, 1H), 7.36 (br m, 1H), 7.08 (m, 3H), 4.34 (tt, J=12,4 Hz, 1H), 4.25 (br m, 1H), 3.30 (d, J=11 Hz, 2H), 2.60–2.35 (br m, 5H), 2.03 (br m, 2H), 1.88 (br m, 4H), 1.73 (br m, 4H). HPLC purity (214 nm)=98%. FABMS 420 ($MH^+$).

EXAMPLE 15

1,3-dihydro-1-{1-[1-(6-chloro-2-pyrazinecarbonyl) piperidin-4-yl]piperidin-4-yl}-2H-benzimidazol-2-one From 1,3-dihydro-1-{1-[1-piperidin-4-yl]piperidin-4-yl}-2H-benzimidazol-2-one dihydrochloride salt and 6-chloro-2-pyrazinoic acid using the procedure described for Example 3, there was obtained 1,3-dihydro-1-{1-[1-(6-chloro-2-pyrazinecarbonyl)piperidin-4-yl]piperidin-4-yl}-2H-benzimidazol-2-one as a white solid: $^1H$ NMR (400 MHz, $CDCl_3$) 9.58 (s, 1H), 8.82 (m, 2H), 8.66 (s, 1H), 7.31 (m, 1H), 7.08 (m, 3H), 4.79 (s, 1H), 4.01 (d, 1H), 3.1 (m, 4H), 2.88 (t, 1H), 2.74 (s, 1H), 2.5 (m, 4H), 2.1–1.87 (m, 4H), 1.7 (m, 2H). The dihydrochloride salt was precipitated from ethanol/chloroform: Analysis calculated for $C_{22}H_{25}ClN_6O_2.0.55$ $CHCl_3.0.85$ $CH_3CH_2OH$: C: 47.08, H: 5.32, N: 13.58 found C: 47.05, H: 5.35, N: 13.57.

EXAMPLE 16

1,3-dihydro-1-{1-[1-(6-methoxy-2-pyrazinecarbonyl) piperidin-4-yl]piperidin-4-yl}-2H-benzimidazol-2-one From 1,3-dihydro-1-{1-[1-piperidin-4-yl]piperidin-4-yl}-2H-benzimidazol-2-one dihydrochloride salt and 6-methoxy-2-pyrazinoic acid using the procedure described for Example 3, there was obtained 1,3-dihydro-1-{1-[1-(6-methoxy-2-pyrazinecarbonyl)piperidin-4-yl]piperidin-4-yl}-2H-benzimidazol-2-one as a white solid: $^1$H NMR (400 MHz, CDCl$_3$) 8.84 (s, 1H), 8.43 (s, 1H), 8.29 (s, 1H), 7.27–7.07 (m, 4H), 4.84 (br s, 1H), 4.4 (br s, 1H), 4.0 (s, 3H), 3.1 (br s, 2H), 2.82 (m, 1H), 2.47 (m, 1H), 2.1–1.9 (br m, 4H), 1.7 (m, 2H). The dihydrochloride salt was precipitated from ethanol/ether: Analysis calculated for C$_{23}$H$_{28}$N$_6$O$_3$.0.30 CH$_3$CH$_2$OH: C: 54.17, H: 6.13, N: 16.06 found C: 54.21, H: 6.29, N: 16.05.

EXAMPLE 17

1,3-dihydro-1-{1-[1-(6-benzyloxy-2-pyrazinecarbonyl)piperidin-4-yl]piperidin-4-yl}-2H-benzimidazol-2-one Step 1: To 1 mL of benzyl alcohol cooled in an ice bath was added 0.1 g of 60% sodium hydride oil dispersion. After 15 min., 0.1 g of 6-chloro-2-pyrazinoic acid was added. The mixture was stirred at room temperature for 1 h, then acidified with 2 mL of 1N HCl. The mixture was cooled in an ice bath and the white precipitate collected by filtration. Drying under vacuum gave 0.132 g of 6-benzyloxy-2-pyrazinoic acid: mp 160°–162° C.; $^1$H NMR (400 MHz, CDCl$_3$) 9.00 (s, 1H), 8.56 (s, 1H), 7.49–7.36 (m, 5H), 5.46 (s, 2H).

Step 2: From 1,3-dihydro-1-{1-[1-piperidin-4-yl]piperidin-4-yl}-2H-benzimidazol-2-one dihydrochloride salt and 6-benzyloxy-2-pyrazinoic acid using the procedure described for Example 3, there was obtained 1,3-dihydro-1-{1-[1-(6-benzyloxy-2-pyrazinecarbonyl)piperidin-4-yl]piperidin-4-yl}-2H-benzimidazol-2-one as a white solid: $^1$H NMR (400 MHz, CDCl$_3$) 9.98 (s, 1H), 8.46 (m, 1H), 8.36 (m, 1H), 7.47–7.05 (m, 9H), 5.43 (m, 2H), 4.81 (br s, 1H), 4.39 (br s, 1H), 3.9 (br s, 1H), 2.85 (m, 1H), 2.65 (m, 1H), 2.46 (m, 4H), 2.02 (br s, 1H), 1.89 (br s, 2H), 1.76–1.2 (m, 4H). The dihydrochloride salt was precipitated from ethanol: Analysis calculated for C$_{29}$H$_{32}$N$_6$O$_3$.0.75 CH$_3$CH$_2$OH.0.45 H$_2$O: C: 61.91, H: 6.54, N: 14.20 found C: 61.92, H: 6.20, N: 14.18.

EXAMPLE 18

1,3-dihydro-1-{1-[1-(6-amino-2-pyrazinecarbonyl)piperidin-4-yl]piperidin-4-yl}-2H-benzimidazol-2-one Step 1: A mixture of 0.15 g of 1,3-dihydro-1-{1-[1-(6-chloro-2-pyrazinecarbonyl)piperidin-4-yl]piperidin-4-yl}-2H-benzimidazol-2-one, 0.26 g of sodium azide and 5 mL of anhydrous N,N-dimethylformamide was stirred for 24 h, then concentrated to dryness under reduced pressure. The residue was partitioned between 50 mL of chloroform and 5 mL of saturated sodium carbonate and the organic extracts dried over MgSO$_4$. Removal of solvents under reduced pressure and drying under vacuum gave 0.16 g of crude 1,3-dihydro-1-{1-[1-(6-azido-2-pyrazinecarbonyl)piperidin-4-yl]piperidin-4-yl}-2H-benzimidazol-2-one.

Step 2: The crude 1,3-dihydro-1-{1-[1-(6-azido-2-pyrazinecarbonyl)piperidin-4-yl]piperidin-4-yl}-2H-benzimidazol-2-one was hydrogenated under 1 atm. of hydrogen in 20 mL of ethanol over 0.05 g of 5% palladium on carbon. The catalyst was removed by filtration and the filtrate concentrated to dryness under reduced pressure. Preparative thin layer chromatography using 20% methanol/10% conc. NH$_4$OH/70% chloroform gave 35 mg of 1,3-dihydro-1-{1-[1-(6-amino-2-pyrazinecarbonyl)piperidin-4-yl]piperidin-4-yl}-2H-benzimidazol-2-one as a solid: $^1$H NMR (400 MHz, CDCl$_3$) 8.12 (s, 1H), 8.02 (s, 1H), 7.85 (br s, 1H), 7.19–7.04 (m, 4H), 4.95 (br s, 1H), 4.62 (br s, 1H), 4.2 (br s, 1H), 3.65 (br s, 1H), 3.6–3.2 (m, 4H), 3.15 (m, 2H), 3.03 (m, 1H), 2.82 (m, 1H), 2.45–2.25 (m, 2H), 2.1–1.8 (m, 4H). The dihydrochloride salt was precipitated from chloroform/methanol: Analysis calculated for C$_{21}$H$_{27}$N$_7$O$_2$.0.45 CHCl$_3$.0.65 NH$_4$Cl: C: 46.25, H: 5.54, N: 18.38 found C: 46.28, H: 5.92, N: 18.48.

EXAMPLE 19

1,3-dihydro-1-{1-[1-(3-amino-2-pyrazinecarbonyl)piperidin-4-yl]piperidin-4-yl}-2H-benzimidazol-2-one From 1,3-dihydro-1-{1-[1-piperidin-4-yl]piperidin-4-yl}-2H-benzimidazol-2-one dihydrochloride salt and 3-amino-2-pyrazinoic acid using the procedure described for Example 3, there was obtained 1,3-dihydro-1-{1-[1-(3-amino-2-pyrazinecarbonyl)piperidin-4-yl]piperidin-4-yl}-2H-benzimidazol-2-one as a white solid: $^1$H NMR (400 MHz, CDCl$_3$) 10.1 (s, 1H), 8.05 (s, 1H), 7.88 (s, 1H), 7.27 (s, 1H), 7.15–7.05 (m, 3H), 5.75 (s, 2H), 4.77 (d, 1H), 4.36 (s, 1H), 4.27 (d, 1H), 2.87 (m, 1H), 2.67 (m, 2H), 2.48 (m, 3H), 2.01 (m, 1H), 1.85 (s, 3H), 1.64 (m, 2H). The dihydrochloride salt was precipitated from ethanol: Analysis calculated for C$_{22}$H$_{27}$N$_7$O$_2$.0.35 CH$_3$CH$_2$OH.1.45 H$_2$O: C: 50.80, H: 6.39, N: 18.27 found C: 50.78, H: 6.25, N: 18.27.

EXAMPLE 20

1,3-dihydro-1-{1-[1-(3-pyridyloxyacetyl)piperidin-4-yl]piperidin-4-yl}-2H-benzimidazol-2-one From 1,3-dihydro-1-{1-[1-piperidin-4-yl]piperidin-4-yl}-2H-benzimidazol-2-one dihydrochloride salt and 3-pyridyloxyacetic acid acid using the procedure described for Example 3, there was obtained 1,3-dihydro-1-{1-[1-(3-pyridyloxyacetyl)piperidin-4-yl]piperidin-4-yl}-2H-benzimidazol-2-one as a white solid: $^1$H NMR (400 MHz, CDCl$_3$) 8.97 (s, 1H), 8.53 (d, 1H), 8.37 (d, 1H), 8.28 (d, 1H), 8.2 (d, 1H), 7.4 (m, 1H), 7.23 (m, 1H), 7.07 (m, 3H), 5.6–4.7 (m, 3H), 4.37 (m, 1H), 3.9 (m, 1H), 3.5–3.0 (m, 4H), 2.75 (br s, 1H), 2.45 (m, 4H), 2.2–1.5 (br m, 4H). The dihydrochloride salt was precipitated from chloroform/toluene: Analysis calculated for C$_{24}$H$_{29}$N$_5$O$_3$.0.75 CHCl$_3$.0.35 CH$_3$C$_6$H$_5$: C: 51.67, H: 5.83, N: 11.08 found C: 51.49, H: 5.93, N: 10.81.

EXAMPLE 21

1,3-dihydro-1-{1-[1-(4-pyrimidinecarbonyl)piperidin-4-yl]piperidin-4-yl}-2H-benzimidazol-2-one From 1,3-dihydro-1-{1-[1-piperidin-4-yl]piperidin-4-yl}-2H-benzimidazol-2-one dihydrochloride salt and 4-pyrimidinecarboxylic acid using the procedure described for Example 3, there was obtained 1,3-dihydro-1-{1-[1-(4-pyrimidinecarbonyl)piperidin-4-yl]piperidin-4-yl}-2H-benzimidazol-2-one as a white solid: $^1$H NMR (400 MHz, CDCl$_3$) 9.25 (s, 1H), 8.90 (s, 2H), 7.98 (s, 1H), 7.61 (s, 1H), 7.3 (m, 1H), 7.1–7.05 (m, 3H), 4.8 (m, 1H), 4.4 (m, 1H), 4.1 (m, 1H), 3.1 (m, 2H), 2.9 (m, 2H), 2.77–2.35 (m, 4H), 2.0–1.5 (m, 7H). The dihydrochloride salt was precipitated from ethanol/toluene: Analysis calculated for C$_{22}$H$_2$ON$_6$O$_2$.0.4 CH$_3$CH$_2$OH.0.5 CH$_3$C$_6$H$_5$: C: 58.08, H: 6.38, N: 15.45 found C: 58.07, H: 6.51, N: 15.49.

EXAMPLE 22

1,3-dihydro-1-{1-[1-(4-pyridazinecarbonyl)piperidin-4-yl]piperidin-4-yl}-2H-benzimidazol-2-one From 1,3-dihydro-1-{1-[1-piperidin-4-yl]piperidin-4-yl}-2H-benzimidazol-2-one dihydrochloride salt and 4-pyridazinecarboxylic acid using the procedure described for Example 3, there was obtained 1,3-dihydro -1-{1-[1-(4- pyridazinecarbonyl)piperidin-4-yl]piperidin-4-yl}-2H-benzimidazol-2-one as a white solid: $^1$H NMR (400 MHz, CDCl$_3$) 9.52 (s, 1H), 9.33 (s, 1H), 9.22 (m, 1H), 7.5 (m, 1H), 7.27 (m, 1H), 7.12–7.04 (m, 3H), 4.77 (m, 1H), 4.35 (br s, 1H), 3.6 (m, 1H), 3.1 (m, 2H), 2.9 (m, 1H), 2.65 (m, 1H), 2.44 (m, 4H), 2.1 (br s, 1H), 1.87 (m, 4H), 1.6 (m, 2H). The dihydrochloride salt was precipitated from ethanol/ether: Analysis calculated for $C_{22}H_{26}N_6O_2 \cdot 0.62$ $CH_3CH_2OH \cdot 0.35$ $(CH_3CH_2)_2O$: C: 55.44, H: 6.64, N: 15.77; found C: 55.46, H: 6.92, N: 15.77.

EXAMPLE 23

1,3-dihydro-1-{1-[1-(4-imidazolecarbonyl)piperidin-4-yl]piperidin-4-yl}-2H-benzimidazol-2-one From 1,3-dihydro-1-{1-[1-piperidin-4-yl]piperidin-4-yl}-2H-benzimidazol-2-one dihydrochloride salt and 4-imidazolecarboxylic acid using the procedure described for Example 3, there was obtained 1,3-dihydro-1-{1-[1-(4-imidazolecarbonyl)piperidin-4-yl]piperidin-4-yl}-2H-benzimidazol-2-one as a white solid: $^1$H NMR (400 MHz, CDCl$_3$) 10.85 (br s, 0.5H), 9.9 (br s, 0.5H), 8.78 (s, 1H), 7.73 (s, 0.5H), 7.63 (d, 1H), 7.4 (s, 0.5H), 7.27 (m, 1H), 7.06 (m, 3H), 4.6 (br s, 1H), 4.33 (br s, 1H), 3.08 (m, 4H), 2.67 (m, 1H), 2.44 (m, 4H), 2.0–1.8 (m, 4H), 1.6 (br m, 3 nH). The dihydrochloride salt was precipitated from ethanol/ether: Analysis calculated for $C_{21}H_{26}N_6O_2 \cdot 1.0$ $CH_3CH_2OH \cdot 0.5$ $H_2O$: C: 52.87, H: 6.75, N: 16.09; found C: 53.03, H: 6.53, N: 15.73.

EXAMPLE 24

1,3-dihydro-1-{1-[1-(4-amino-5-pyrimidinecarbonyl)piperidin-4-yl]piperidin-4-yl}-2H-benzimidazol-2-one From 1,3-dihydro-1-{1-[1-piperidin-4-yl]piperidin-4-yl}-2H-benzimidazol-2-one dihydrochloride salt and 4-amino-5-pyrimidinecarboxylic acid using the procedure described for Example 3, there was obtained 1,3-dihydro-1-{1-[1-(4-amino-5-pyrimidinecarbonyl)piperidin-4-yl]piperidin-4-yl}-2H-benzimidazol-2-one as a white solid: $^1$H NMR (400 MHz, CDCl$_3$) 10.0 (br s, 1H), 8.57 (s, 1H), 8.23 (s, 1H), 7.27 (s, 1H), 7.13–7.03 (m, 3H), 6.98 (br s, 2H), 4.34 (br s, 2H), 3.4–1.5 (complex m, 17H). The dihydrochloride salt was precipitated from ethanol/ether: Analysis calculated for $C_{22}H_{27}N_7O_2 \cdot 1.25$ $CH_3CH_2OH$: C: 53.31, H: 6.66, N: 17.76; found C: 53.37, H: 6.49, N: 17.73.

EXAMPLE 25

5-ethyl-1,3-dihydro-1-{1-[1-(5-pyrimidinecarbonyl)piperidin-4-yl]piperidin-4-yl}-2H-benzimidazol-2-one From 4-bromo-3-nitro-ethylbenzene using the procedures described for Example 2, there was obtained 5-ethyl-1,3-dihydro-1-{1-[1-(5-pyrimidinecarbonyl)piperidin-4-yl]piperidin-4-yl}-2H-benzimidazol-2-one as a white solid: $^1$H NMR (400 MHz, CDCl$_3$) 9.81 (s, 1H), 9.29 (s, 1H), 8.84 (s, 2H), 7.19 (d, 1H), 6.98 (s, 1H), 6.89 (d, 1H), 4.8 (br s, 1H), 4.3 (br s, 1H), 3.8 (br s, 1H), 3.1 (br m, 4H), 2.84 (br m, 1H), 2.65 (q, 2H), 2.4 (br m, 4H), 2.3–1.4 (br m, 6H), 1.22 (t, 3H). The dihydrochloride salt was precipitated from ethanol/toluene: Analysis calculated for $C_{24}H_{30}N_6O_2 \cdot 1.6$ $H_2O \cdot 0.4$ $CH_3C_6H_5$: C: 56.16, H: 6.77, N: 14.66; found C: 56.18, H: 6.37, N: 14.69.

EXAMPLE 26

5-methoxy-1,3-dihydro-1-{1-[1-(5-pyrimidinecarbonyl)piperidin-4-yl]piperidin-4-yl}-2H-benzimidazol-2-one From 4-chloro-3-nitro-anisole using the procedures described for Example 2, there was obtained 5-methoxy-1,3-dihydro-1-{1-[1-(5-pyrimidinecarbonyl)piperidin-4-yl]piperidin-4-yl}-2H-benzimidazol-2-one as a white solid: $^1$H NMR (400 MHz, CDCl$_3$) 9.79 (s, 1H), 9.29 (s, 1H), 8.84 (s, 2H), 7.18 (br m, 1H), 6.73 (s, 1H), 6.63 (d, 1H), 4.8 (br s, 1H), 4.3 (br s, 1H), 3.8 (s, 4H), 3.1 (br m, 4H), 2.84 (br m, 1H), 2.65 (br m, 2H), 2.4 (br m, 4H), 2.1–1.8 (br m, 4H), 1.6 (br m, 1H). The dihydrochloride salt was precipitated from ethanol/toluene: Analysis calculated for $C_{23}H_{28}N_6O_3 \cdot 0.3$ $CH_3C_6H_5$: C: 56.13, H: 6.08, N: 15.65; found C: 56.13, H: 6.39, N: 15.57.

EXAMPLE 27

5-chloro-1,3-dihydro-1-{1-[1-(5-pyrimidinecarbonyl)piperidin-4-yl]piperidin-4-yl}-2H-benzimidazol-2-one From 2,5-dichloronitrobenzene using the procedures described for Example 2, there was obtained 5-chloro-1,3-dihydro-1-{1-[1-(5-pyrimidinecarbonyl)piperidin-4-yl]piperidin-4-yl}-2H-benzimidazol-2-one as a white solid: $^1$H NMR (400 MHz, CDCl$_3$+d6-DMSO) 9.3 (s, 1H), 8.83 (s, 2H), 8.2 (s, 1H), 7.20–7.05 (m, 3H), 4.5 (br m, 2H), 3.4–2.3 (br m, 12H), 2.0–1.4 (br m, 6H). The dihydrochloride salt was precipitated from ethanol/chloroform: Analysis calculated for $C_{22}H_{25}ClN_6O_2 \cdot 0.3$ $CHCl_3 \cdot 0.95$ $H_2O$: C: 46.87, H: 5.15, N: 14.67; found C: 46.84, H: 5.54, N: 14.62.

EXAMPLE 28

5-fluoro-1,3-dihydro-1-{1-[1-(5-pyrimidinecarbonyl)piperidin-4-yl]piperidin-4-yl}-2H-benzimidazol-2-one From 2-chloro-5-fluoronitrobenzene using the procedures described for Example 2, there was obtained 5-fluoro-1,3-dihydro-1-{1-[1-(5-pyrimidinecarbonyl)piperidin-4-yl]piperidin-4-yl}-2H-benzimidazol-2-one as a white solid: $^1$H NMR (400 MHz, CDCl$_3$) 9.43 (s, 1H), 9.30 (s, 1H), 8.83 (s, 2H), 7.2 (m, 1H), 6.86–6.77 (m, 2H), 4.8 (br s, 1H), 4.4 (br m, 1H), 3.8 (br m, 1H), 3.1 (br m, 4H), 2.88 (br m, 1H), 2.74 (br m, 1H), 2.44 (br m, 4H), 2.0 (br m, 1H), 1.88 (br m, 2H), 1.58 (br m, 2H). The dihydrochloride salt was precipitated from ethanol/toluene: Analysis calculated for $C_{23}H_{28}N_6O_3 \cdot 0.3$ $CH_3C_6H_5$: C: 56.13, H: 6.08, N: 15.65; found C: 56.13, H: 6.39, N: 15.57.

EXAMPLE 29

1,3-Dihydro-1-{1-[1-(5-pyrimidinylcarbonyl)piperidin-4-yl]piperidin-4-yl}-1H-3,4-dihydroquinazolin-2-one Step 1: A mixture of 45 g of 2-aminomethylaniline, 60 g of di-tert-butyldicarbonate, 1000 mL of dichloromethane was stirred for 18 h and washed with 500 mL of 2N NaOH. The organic extract was dried over MgSO$_4$ and concentrated under reduced pressure. Drying under vacuum gave 47 g of 2-(tert-butoxycarbonylaminomethyl)aniline as a white crystalline solid. $^1$H NMR (400 MHz, CDCl$_3$) 7.1 (t, 1H), 7.05 (d, 1H), 6.65 (dd, 2H), 4.8 (br s, 1H), 4.2 (br m, 4H), 1.44 (s, 9H).

Step 2: A mixture of 15.5 g of 2-(tert-butoxycarbonylaminomethyl)aniline, 15 g of N-t-butyloxycarbonyl-4-piperidone, 250 mL of 1,2-dichloroethane, 4.2 mL of glacial acetic acid and 25 g of sodium triacetoxyborohydride was stirred at room temperature for 48 h. The reaction mixture was poured into 500 mL chloroform and 500 mL saturated aqueous Na$_2$CO$_3$ and the layers separated. The aqueous layer was extracted with 2×250 mL of chloroform and the combined organic layers dried over MgSO$_4$ and concentrated under reduced pressure. Drying overnight under vacuum gave 30.1 g of tert-butyl (2-(tert-butoxycarbonylaminomethyl)anilino)piperidine carboxylate as a solid: $^1$H NMR (400 MHz, CDCl$_3$) 7.19 (t, 1H), 7.0 (d, 1H), 6.6 (dd, 2H), 4.94 (br s, 1H), 4.75 (br s, 1H), 4.23 (br m, 2H), 4.0 (br m, 2H), 3.45 (br m, 1H), 3.0 (br m, 2H), 2.0 (br m, 2H), 1.82 (br m, 1H), 1.46 (s, 9H), 1.44 (s, 9H).

Step 3: To a stirred solution of 27.1 g of tert-butyl 4-(2-tert-butoxycarbonylaminomethylanilino)-1-piperidinecarboxylate and 30 mL of triethylamine in 400 mL of dichloromethane was added dropwise 60 mL of a 1.93M solution of phosgene in toluene. After stirring for 12 h, 200 mL of 1N NaOH was added. The mixture was shaken, and the organic layer separated, dried over MgSO$_4$ and concentrated under reduced pressure. Chromatography on silica gel, eluting with 25% ethyl acetate in hexane gave, after drying overnight under vacuum, 25 g of 1,3-dihydro-1-[1-tert-butoxycarbonylpiperidin-4-yl]-3-tert-butoxycarbonyl-1H-3,4-dihydroquinazolin-2-one carboxylate as a clear glass:$^1$H NMR (400 MHz, CDCl$_3$) 7.52 (d, 1H), 7.45 (t, 1H), 7.36 (m, 1H), 7.10 (d, 1H), 4.2–4.0 (br m, 5H), 3.65–3.25 (br m, 2H), 2.75 (br m, 2H), 2.28 (br d, 1H), 1.8 (br d, 1H), 1.5 (s, 9H), 1.49 (s, 9H).

Step 4: A stirred solution of 25 g of 1,3-dihydro-1-[1-tert-butoxycarbonylpiperidin-4-yl]-3-tert-butoxycarbonyl-1H-3,4-dihydroquinazolin-2-one carboxylate in 1 L of ethyl acetate cooled to −50° C. was saturated with hydrogen chloride gas for 15 min. The resulting mixture was allowed to warm to room temperature and stir for 4 h. The white solid precipitate was collected by filtration. Drying under vacuum gave 13.1 of 1,3-dihydro-1-[piperidin-4-yl]-3-tert-butoxycarbonyl-1H-3,4-dihydroquinazolin-2-one hydrochloride salt as a white solid. The salt (0.8 g) was converted to the free base by partitioning between chloroform and saturated sodium carbonate. Drying under vacuum gave 0.68 g of 1,3-dihydro-1-[piperidin-4-yl]-1H-3,4-dihydroquinazolin-2-one as a white solid: $^1$H NMR (400 MHz, CDCl$_3$) 7.25 (dd, 1H), 7.12 (d, 1H), 7.06 (d, 1H), 6.98 (t, 1H), 5.2 (br s, 1H), 4.28 (s, 2H), 4.10 (m, 1H), 3.22 (d, 2H), 2.73 (m, 2H), 2.59 (m, 2H), 2.05 (br s, 1H), 1.82 (br d, 2H).

Step 5: A mixture of 0.52 g of 1,3-dihydro-1-[piperidin-4-yl]-1H-3,4-dihydroquinazolin-2-one, 0.65 g of N-t-butyloxycarbonyl-4-piperidone, 10 mL of 1,2-dichloroethane, 0.3 mL of glacial acetic acid and 1 g of sodium triacetoxyborohydride was stirred at room temperature for 48 h. The reaction mixture was poured into 50 mL chloroform and 50 mL saturated aqueous Na$_2$CO$_3$ and the layers separated. The aqueous layer was extracted with 2×25 mL of chloroform and the combined organic layers dried over MgSO$_4$ and concentrated under reduced pressure. Chromatography over silica gel using 15% methanol in ethyl acetate gave 0.9 g of 1,3-dihydro-1-{1-[1-(tert-butyloxycarbonyl)piperidin-4-yl]piperidin-4-yl}-1H-3,4-dihydroquinazolin-2-one as a solid: $^1$H NMR (400 MHz, CDCl$_3$) 7.22 (t, 1H), 7.14 (d, 1H), 7.05 (d, 1H), 6.97 (t, 1H), 5.57 (br s, 1H), 4.27 (s, 2H), 4.1 (br m, 4H), 3.07 (d, 2H), 2.68 (br m, 4H), 2.5 (br t, 1H), 2.36 (br t, 2H), 1.8 (br d, 4H), 1.82 (br m, 1H), 1.46 (s, 9H).

Step 6: A stirred solution of 0.9 g of 1,3-dihydro-1-{1-[1-(tert-butyloxycarbonyl)piperidin-4-yl]piperidin-4-yl}-1H-3,4-dihydroquinazolin-2-one in 40 mL of 1N HCl was heated to reflux for 6 h, cooled and concentrated to dryness. After drying overnight under vacuum, there was obtained 0.58 g of 1,3-dihydro-1-{1-[piperidin-4-yl]piperidin-4-yl}-1H-3,4-dihydroquinazolin-2-one dihydrochloride salt as a white solid.

Step 7: To a stirred solution of 0.58 g of 1,3-dihydro-1-{1-[piperidin-4-yl]piperidin-4-yl}-1H-3,4-dihydroquinazolin-2-one dihydrochloride salt and 1 mL of triethylamine in 50 mL of dichloromethane was added 0.3 g of pyrimidine-5-carboxylic acid chloride. After 2 h, 50 mL of dilute aqueous ammonia was added and the mixture stirred for an additional 30 min. The organic layer was separated, the aqueous layer extracted with two additional 50 mL portions of chloroform and the combined organic extracts dried over MgSO$_4$ and concentrated under reduced pressure. Chromatography over silica gel using 15% methanol in ethyl acetate gave 0.45 g of 1,3-dihydro- 1-{1-[1-(5-pyrimidinylcarbonyl)piperidin-4-yl]piperidin-4-yl]-1H-3,4-dihydroquinazolin-2-one as a white solid: $^1$H NMR (400 MHz, CDCl$_3$) 9.26 (s, 1H), 8.82 (s, 2H), 7.22 (m, 1H), 7.11 (m, 1H), 7.05 (m, 1H), 6.95, (m, 1H), 6.16 (br s, 1H), 4.72 (br s, 1H), 4.27 (s, 2H), 4.04 (br m, 1H), 3.74 (br s, 1H), 3.06 (br m, 2H), 2.87 (br m, 1H), 2.7 (br m, 4H), 2.36 (m, 2H), 2.05 (br m, 1H), 1.99 (br m, 1H), 1.81(br m, 2H), 1.58 (br m, 2H). The dihydrochloride salt was ethanol/ethyl acetate: Analysis calculated for C$_{23}$H$_{28}$N$_6$O$_2$.1.95HCl C: 56.19, H: 6.14, N: 17.10 found C: 56.57, H: 6.54, N: 16.70.

EXAMPLE 30

(±)-1,3-Dihydro-1-{1-[1-(1-(5-pyrimidinyl)-ethyl)piperidin-4-yl]piperidin-4-yl}-2H-benzimidazol-2-one Step 1: To a stirred mixture of 1.1 g of 5-(1-aminoethyl)pyrimidine (O. Cervinska and P. Malon, *Coll. Czechoslov. Chem. Commun.* 1977, 42, 3464–72.), 17 mL of ethanol and 1.36 g of K$_2$CO$_3$ heated to reflux was added dropwise over 30 min, a solution of 4 g of 1,1-dimethyl-4-oxopiperidinium iodide in 70 mL of water. When the addition was complete, the mixture was heated under reflux for an additional 2 h, cooled, basified to pH 9 with K$_2$CO$_3$ and extracted with 5 times with 50 mL portions of methylene chloride. The combined organic extracts were dried over MgSO$_4$ and concentrated under reduced pressure. Chromatography over silica gel, eluting with 90:10 CH$_3$CN:MeOH gave 0.48 g of 1-(1-(5-pyrimidinyl)-ethyl)-4-oxopiperidine as an oil: $^1$H NMR (400 MHz, CDCl$_3$) 9.14 (s, 1H), 8.78 (s, 2H), 3.8 (q, J=7 Hz, 1H), 2.7–2.9 (m, 4H), 2.45 (m, 4H), 1.5 (d, J=7 Hz, 3H).

Step 2: A mixture of 0.24 g of 1-(1-(5-pyrimidinyl)-ethyl)-4-oxopiperidine, 0.24 g of 1-(4-piperidinyl) benzimidazol-2H-one, 4 mL of 1,2-dichloroethane, 0.12 mL of glacial acetic acid and 0.45 g of sodium triacetoxyborohydride was stirred at room temperature for 48 h. The reaction mixture was poured into 100 mL dichloromethane and 25 mL saturated aqueous Na$_2$CO$_3$ and the layers separated. The aqueous layer was extracted with 2×25 mL of dichloromethane and the combined organic layers dried over MgSO$_4$ and concentrated under reduced pressure. Trituration of the residue with 10 mL of ethyl acetate gave 90 mg of (±)-1,3-dihydro-1-{1-[1-(1-(5-pyrimidinyl)-1-ethyl)piperidin-4-yl]piperidin-4-yl}-2H-benzimidazol-2-one as a white solid. Purification of the filtrate by chromatography on silica gel eluting with 220:60:20 CHCl$_3$: MeOH:conc. NH$_4$OH gave an additional 220 mg of product: $^1$H NMR (400 MHz, CDCl$_3$) 9.7 (s, 1H), 9.12 (s, 1H), 8.71 (s, 2H), 7.26 (br m, 1H), 7.0–7.1 (br m, 3H), 4.35 (br m, 1H), 3.55 (q, J=7 Hz, 1H), 3.0–3.1 (m, 3H), 2.85 (m, 1H), 2.3–2.5 (m, 5H), 2.05 (br t, 2H), 1.86 (br m, 4H), 1.6 (br m, 2H), 1.4 (d, J=7 Hz, 3H). Analysis calculated for C$_{23}$H$_{30}$N$_6$O.0.5 H$_2$O.0.15 CH$_3$CO$_2$CH$_2$CH$_3$: C: 66.11, H: 7.57, N: 19.60 found C: 66.22, H: 7.29, N: 19.23.

EXAMPLE 31

(1'''S) 1,3-Dihydro-1-{1'-[1''-(1'''-(5''''-pyrimidinyl)ethyl)piperidin-4''-yl]piperidin-4'-yl}-2H-benzimidazol-2-one From (S)-(−)-5-(1-aminoethyl)pyrimidine (O. Cervinska and P. Malon, *Coll. Czechoslov. Chem. Commun.* 1977, 42, 3464–72.) using the procedures described in Example 30 there was obtained (1′″S) 1,3-dihydro-1-{1'-[1"-(1'"-(5""-pyrimidinyl)-ethyl)piperidin-4"-yl]piperidin-4'-yl}-2H-benzimidazol-2-one as a white solid: mp 126°–7° C.; $^1$H NMR (400 MHz, CDCl$_3$) 9.7 (s, 1H), 9.12 (s, 1H), 8.71 (s, 2H), 7.26 (br m, 1H), 7.0–7.1 (br m, 3H), 4.35 (br m, 1H), 3.55 (q, J=7 Hz, 1H), 3.0–3.1 (m, 3H), 2.85 (m, 1H), 2.3–2.5 (m, 5H), 2.05 (br t, 2H), 1.86 (br m, 4H), 1.6 (br m, 2H), 1.4 (d, J=7 Hz, 3H). The bis-maleate salt: Analysis calculated for C$_{23}$H$_{30}$N$_6$O.2 C$_4$H$_4$O$_4$: C:58.29, H: 6.00, N: 13.16 found C: 58.29, H: 6.00, N: 13.25.

EXAMPLE 32

(1′″R) 1,3-Dihydro-1-{1'-[1"-(1'"-(5""-pyrimidinyl)-ethyl)piperidin-4"-yl]piperidin-4'-yl}-2H-benzimidazol-2-one From (R)-(+)-5-(1-aminoethyl)pyrimidine (from D-tartaric acid using procedure of O. Cervinska and P. Malon, *Coll. Czechoslov. Chem. Commun.* 1977, 42, 3464–72.) using the procedures described in Example 30 there was obtained (1′″R) 1,3-dihydro-1-{1'-[1"-(1'"-(5""-pyrimidinyl)-ethyl)piperidin-4"-yl]piperidin-4'-yl}-2H-benzimidazol-2-one as a white solid: mp 126°–7° C.; $^1$H NMR (400 MHz, CDCl$_3$) 9.7 (s, 1H), 9.12 (s, 1H), 8.71 (s, 2H), 7.26 (br m, 1H), 7.0–7.1 (br m, 3H), 4.35 (br m, 1H), 3.55 (q, J=7 Hz, 1H), 3.0–3.1 (m, 3H), 2.85 (m, 1H), 2.3–2.5 (m, 5H), 2.05 (br t, 2H), 1.86 (br m, 4H), 1.6 (br m, 2H), 1.4 (d, J=7 Hz, 3H). The bis-maleate salt: Analysis calculated for C$_{23}$H$_{30}$N$_6$O.2 C$_4$H$_4$O$_4$.0.5 H$_2$O: C:57.88, H: 6.03, N: 13.07; found C: 57.78, H: 5.91, N: 13.01.

EXAMPLE 33

(1′″S) 1,3-Dihydro-1-{1'-[1"-(1'"-(5""-pyrimidinyl)ethyl)piperidin-4"-yl]piperidin-4'-yl}-5-chloro-2H-benzimidazol-2-one From (S)-(−)-5-(1-aminoethyl)pyrimidine (O. Cervinska and P. Malon, *Coll. Czechoslov. Chem. Commun.* 1977, 42, 3464–72.) using the procedures described in Example 30, but substituting 5-chloro-1-(4-piperidinyl) benzimidazol-2H-one for 1-(4-piperidinyl) benzimidazol-2H-one, there was obtained (1′″S) 1,3-dihydro-1-{1'-[1"-(1'"-(5""-pyrimidinyl)-ethyl)piperidin-4"-yl]piperidin-4'-yl}-5-chloro-2H-benzimidazol-2-one as a white solid: mp 203°–5° C.; $^1$H NMR (400 MHz, CDCl$_3$) 9.12 (s, 1H), 8.95 (br s, 1H), 8.71 (s, 2H), 7.18 (d, 1H), 7.07 (d, 1H), 7.01 (dd, 1H), 4.3 (br m, 1H), 3.55 (q, J=7 Hz, 1H), 3.0–3.1 (m, 3H), 2.85 (m, 1H), 2.3–2.5 (m, 5H), 2.05 (br t, 2H), 1.85 (br m, 4H), 1.6 (br m, 2H), 1.4 (d, J=7 Hz, 3H). The bis-maleate salt: Analysis calculated for C$_{23}$H$_{29}$ClN$_6$O.2 C$_4$H$_4$O$_4$: C:55.31, H: 5.54, N: 12.49; found C: 55.41, H: 5.54, N: 12.60.

EXAMPLE 34

(1′″R) 1,3-Dihydro-1-{1'-[1"-(1'"-(5""-pyrimidinyl)ethyl)piperidin-4"-yl]piperidin-4'-yl}-5-chloro-2H-benzimidazol-2-one From (R)-(+)-5-(1-aminoethyl)pyrimidine (from D-tartaric acid using procedure of O. Cervinska and P. Malon, *Coll. Czechoslov. Chem. Commun.* 1977, 42, 3464–72.) using the procedures described in Example 30, but substituting 5-chloro-1-(4-piperidinyl) benzimidazol-2H-one for 1-(4-piperidinyl) benzimidazol-2H-one, there was obtained (1′″R) 1,3-dihydro-1-{1'-[1"-(1'"-(5""-pyrimidinyl)-ethyl)piperidin-4"-yl]piperidin-4'-yl}-5-chloro-2H-benzimidazol-2-one as a white solid: mp 202°–4° C.; $^1$H NMR (400 MHz, CDCl$_3$) 9.12 (s, 1H), 8.95 (br s, 1H), 8.71 (s, 2H), 7.18 (d, 1H), 7.07 (d, 1H), 7.01 (dd, 1H), 4.3 (br m, 1H), 3.55 (q, J=7 Hz, 1H), 3.0–3.1 (m, 3H), 2.85 (m, 1H), 2.3–2.5 (m, 5H 2.05 (br t, 2H), 1.85 (br m, 4H), 1.6 (br m, 2H), 1.4 (d, J=7 Hz, 3H). The bis-maleate salt: Analysis calculated for C$_{23}$H$_{29}$ClN$_6$O.2 C$_4$H$_4$O$_4$.0.25 CH$_3$CH$_2$OH.1.0 H$_2$O: C:53.68, H: 5.90, N: 11.81; found C: 53.68, H: 5.51, N: 11.59.

EXAMPLE 35

(1′″S) 1,3-Dihydro-1-{1'-[1"-(1'"-(5""-pyrimidinyl)ethyl)piperidin-4"-yl]piperidin-4'-yl}-5-methyl-2H-benzimidazol-2-one From (S)-(−)-5-(1-aminoethyl)pyrimidine (O. Cervinska and P. Malon, *Coll. Czechoslov. Chem. Commun.* 1977, 42, 3464–72.) using the procedures described in Example 30, but substituting 5-methyl-1-(4-piperidinyl) benzimidazol-2H-one for 1-(4-piperidinyl) benzimidazol-2H-one, there was obtained (1′″S) 1,3-dihydro-1-{1'-[1"-(1'"-(5""-pyrimidinyl)-ethyl)piperidin-4"-yl]piperidin-4'-yl}-5-methyl-2H-benzimidazol-2-one as a white solid: mp 179°–180° C.; $^1$H NMR (400 MHz, CDCl$_3$) 9.12 (s, 1H), 8.70 (s, 2H), 8.16 (br s, 1H), 7.17 (d, 1H), 6.87 (br s, 1H), 6.85 (d, 1H), 4.3 (br m, 1H), 3.55 (q, J=7 Hz, 1H), 3.0–3.1 (m, 3H), 2.85 (m, 1H), 2.3–2.5 (m, 5H), 2.36 (s, 3H), 2.05 (br t, 2H), 1.85 (br m, 4H), 1.6 (br m, 2H), 1.4 (d, J=7 Hz, 3H). The bis-maleate salt: Analysis calculated for C$_{24}$H$_{32}$N$_6$O.2 C$_4$H$_4$O$_4$.0.5 H$_2$O: C:58.08, H: 6.25, N: 12.70; found C: 58.28, H: 6.13, N: 12.47.

EXAMPLE 36

(1′″R) 1,3-Dihydro-1-{1'-[1"-(1'"-(5""-pyrimidinyl)ethyl)piperidin-4"-yl]piperidin-4'-yl}-5-methyl-2H-benzimidazol-2-one From (R)-(+)-5-(1-aminoethyl)pyrimidine (from D-tartaric acid using procedure of O. Cervinska and P. Malon, *Coll. Czechoslov. Chem. Commun.* 1977, 42, 3464–72.) using the procedures described in Example 30, but substituting 5-methyl-1-(4-piperidinyl) benzimidazol-2H-one for 1-(4-piperidinyl) benzimidazol-2H-one, there was obtained (1′″R) 1,3-dihydro-1-{1'-[1"-(1'"-(5""-pyrimidinyl)-ethyl)piperidin-4"-yl]piperidin-4'-yl}-5-methyl-2H-benzimidazol-2-one as a white solid: mp 170°–172° C.; $^1$H NMR (400 MHz, CDCl$_3$) 9.12 (s, 1H), 8.70 (s, 2H), 8.16 (br s, 1H), 7.17 (d, 1H), 6.87 (br s, 1H), 6.85 (d, 1H), 4.3 (br m, 1H), 3.55 (q, J=7 Hz, 1H), 3.0–3.1 (m, 3H), 2.85 (m, 1H), 2.3–2.5 (m, 5H), 2.36 (s, 3H), 2.05 (br t, 2H), 1.85 (br m, 4H), 1.6 (br m, 2H), 1.4 (d, J=7 Hz, 3H). The bis-maleate salt: Analysis calculated for C$_{24}$H$_{32}$N$_6$O.2C$_4$H$_4$O$_4$.0.5 H$_2$O: C:58.08, H: 6.25, N: 12.70; found C: 58.28, H: 6.13, N: 12.47.

EXAMPLE 37

1,3-Dihydro-1-{1-[4-oxocyclohex-1-yl]piperidin-4-yl}-2H-benzimidazol-2-one

Step 1: A mixture of 5 g of 1,4-cyclohexanedione mono-ethyleneketal, 4.3 g of 1,3-dihydro-1-(4-piperidinyl)-benzimidazol-2H-one, 75 mL of 1,2-dichloroethane, 1.2 mL of acetic acid and 5.45 g of sodium triacetoxyborohydride was stirred at room temperature for 48 h. The reaction mixture was poured into 500 mL chloroform and 500 mL saturated aqueous Na$_2$CO$_3$ and the layers separated. The aqueous layer was extracted with 2×250 mL of chloroform and the combined organic layers dried over MgSO$_4$ and concentrated under reduced pressure. Trituration of the crude product with 200 mL of ethyl ether gave 7.0 g of the ethylene ketal of 1,3-dihydro-1-{1-[4-oxocyclohex-1-yl]piperidin-4-yl}-2H-benzimidazol-2-one as a white solid: mp=208°–210° C.; ¹H NMR (400 MHz, CDCl₃) 9.14 (br s, 1H), 7.3 (m, 1H), 7.1 (m, 1H), 7.05 (m, 2H), 4.35 (br s, 1H), 3.96 (s, 4H), 3.05 (br d, J=6.6, 2H), 2.45 (m, 4H), 1.84 (br d, J=2.8, 5H), 1.72–1.55 (m, 6H).

Step 2: A mixture of 7.0 g of the ethylene ketal of 1,3-dihydro-1-{1-[4-oxocyclohex-1-yl]piperidin-4-yl}-2H-benzimidazol-2-one, 80 mL of glacial acetic acid, 80 mL of water and 20 mL of conc. HCl was heated under reflux for 2 h, then allowed to cool overnight. The mixture was concentrated under reduced pressure, diluted with 100 mL of saturated Na₂CO₃ and extracted into 3×200 mL of CHCl₃. The combined organic extracts were dried over MgSO₄ and concentrated under reduced pressure. Trituration with ether-ethyl acetate and drying under vacuum gave 5 g of 1,3-dihydro-1-{1-[4-oxocyclohex-1-yl]piperidin-4-yl}-2H-benzimidazol-2-one as a white solid: mp=221°–223° C.; ¹H NMR (400 MHz, CDCl₃) 8.68 (br s, 1H), 7.28 (m, 2H), 7.07 (m, 2H), 4.35 (br s, 1H), 3.12 (br d, J=8.7, 2H), 2.82 (br t, J=9.74, 2H), 2.50 (br t, J=13.76, 2H), 2.44–2.32 (m, 6H), 2.06 (br s, 2H), 1.87 (br d, J=10.9, 4H). Analysis calculated for $C_{18}H_{23}N_3O_2 \cdot 0.4 H_2O$: C: 67.44, H: 7.48, N: 13.11. found C: 67.44, H: 7.41, N: 12.86.

EXAMPLE 38 cis-1,3-Dihydro-1-{1-[1-(5-pyrimidinylamino)cyclohex-4-yl]piperidin-4-yl}-2H-benzimidazol-2-one and trans-1,3-Dihydro-1-{1-[1-(5-pyrimidinylamino)cyclohex-4-yl]piperidin-4-yl}-2H-benzimidazol-2-one A mixture of 0.25 g of 1,3-dihydro-1-{1-[4-oxocyclohex-1-yl]piperidin-4-yl}-2H-benzimidazol-2-one, 0.25 g of 5-aminopyrimidine (H. Bredereck, F. Effenberger and E. H. Schweizer, *Chem. Ber.* 1962 95, 803–9), 2 mL of 1,2-dichloroethane, 0.5 mL of acetic acid and 0.35 g of sodium triacetoxyborohydride was stirred at room temperature for 48 h. The reaction mixture was poured into 200 mL chloroform and 20 mL saturated aqueous Na₂CO₃ and the layers separated. The aqueous layer was extracted with 2×25 mL of CHCl₃ and the combined organic layers dried over MgSO₄ and concentrated under reduced pressure. Preparative TLC on silica gel, eluting with 85:15:5 Et₂O:MeOH:conc. NH₄OH gave 85 mg of trans-1,3-dihydro-1-{1-[1-(5-pyrimidinylamino)cyclohex-4-yl]piperidin-4-yl}-2H-benzimidazol-2-one: ¹H NMR (400 MHz, CDCl₃+5% CD₃OD) 8.44 (s, 1H), 8.12 (m, 2H), 7.36 (m, 1H), 7.09 (m, 3H), 4.3 (br m, 1H), 3.65 (br m, 2H), 3.2 (br m, 2H), 2.45 (m, 5H), 2.0 (m, 2H), 1.85 (br m, 4H), 1.65 (m, 4H): Analysis calculated for $C_{22}H_{28}N_6O \cdot 1.05 H_2O \cdot 0.25 CHCl_3$: C: 60.56, H: 7.17, N: 18.68; found C: 60.81, H: 7.17, N: 18.68, and 75 mg of cis-1,3-dihydro-1-{1-[1-(5-pyrimidinylamino)cyclohex-4-yl]piperidin-4-yl}-2H-benzimidazol-2-one: ¹H NMR (400 MHz, CDCl₃+5% CD₃OD) 8.43 (s, 1H), 8.08 (m, 2H), 7.65 (m, 1H), 7.1 (m, 3H), 4.6 (br m, 1H), 3.6 (br m, 2H), 3.25 (br m, 2H), 3.0 (br m, 5H), 2.3 (m, 4H), 2.0 (m, 2H), 1.75 (br m, 2H), 1.35 (m, 2H): Analysis calculated for $C_{22}H_{28}N_6O \cdot 0.25 H_2O \cdot 0.75 CHCl_3$: C: 55.90, H: 5.97, N: 17.16; found C: 56.19, H: 5.96, N: 17.14.

EXAMPLE 39 trans-1,3-Dihydro-1-{4-[4-(3-pyridinylmethyl)piperazin-1-yl]-1-cyclohexyl}-2H-benzimidazol-2-one Step 1: A mixture of 0.10 g of trans-1,3-dihydro-1-{4-(1-piperazinyl)-1-cyclohexyl}-2H-benzimidazol-2-one, 0.037 mL of 3-pyridinecarboxaldehyde, 15 mL of 1,2-dichloroethane, 0.10 mL of glacial acetic acid and 0.11 g of sodium triacetoxyborohydride was stirred at room temperature for 24 h. The reaction mixture was poured into 10 mL dichloromethane and 10 mL saturated aqueous NaHCO₃ and the layers separated. The aqueous layer was extracted with 2×10 mL of dichloromethane and the combined organic layers dried over MgSO₄ and concentrated under reduced pressure. Preparative thin layer chromatography on silica gel, eluting with 90:10:2 chloroform: methanol: conc. NH₄OH gave 0.050 g of trans-1,3-dihydro-1-{4-[4-(3-pyridinylmethyl)piperazin-1-yl]-1-cyclohexyl}-2H-benzimidazol-2-one as a white solid: mp=250° C.; ¹H NMR (400 MHz, CDCl₃) 9.71 (br s, 1H), 8.54 (dd, 2H), 7.68 (d, J=7.9, 1H), 7.26 (t, 1H), 7.15–7.02 (m, 4H), 4.26 (m, 1H), 3.54 (s, 2H), 2.66 (br dd, 4H), 2.27 (q, 2H), 2.10 (d, 2H), 1.97 (d, 2H), 1.92 (q, 2H): Analysis calculated for $C_{23}H_{29}N_5O \cdot 0.45 CHCl_3$ C: 63.25, H: 6.67, N: 15.73 found C: 62.96, H: 6.74, N: 15.54.

EXAMPLE 40

1,3-Dihydro-1-{1-[1-(2-pyrazinylmethyl)piperidin-4-yl]piperidin-4-yl}-2H-benzimidazol-2-one From the procedure in Example 8, substituting pyrazine-2-carboxaldehyde for 3-pyridinecarboxaldehyde them was obtained 1,3-dihydro-1-{1-[1-(2-pyrazinylmethyl)piperidin-4-yl]piperidin-4-yl}-2H-benzimidazol-2-one as white solid: ¹H NMR (400 MHz, CDCl₃) 10.40 (br s, 1H), 8.69 (d, 1H), 8.54 (dd, 1H), 8.47 (d, 1H), 7.31 (m, 1H), 7.10 (m, 1H), 7.06–7.00 (m, 2H), 4.37 (m, 1H), 3.70 (s, 2H), 3.12 (d, 2H), 2.99 (d, 2H), 2.54–2.40 (m, 5H), 2.15 (t, 2H), 1.85 (d, 4H), 1.70 (qd, 2H).

EXAMPLE 41

(±)-cis-1,3-Dihydro-1-(1-{4-[(5-pyrimidinyl)hydroxymethyl]cyclohex-1-yl}piperidin-4-yl)-2H-benzimidazol-2-one and (±)-trans-1,3-Dihydro-1-(1-{4-[(5-pyrimidinyl)hydroxymethyl]cyclohex-1-yl}piperidin-4-yl) -2H -benzimidazol-2-one Step 1: A mixture of ethyl 4-oxocyclohexanecarboxylate (1.86 g), 4-(2-oxo-1-benzimidazolinyl)piperidine (1.98 g), 1,2-dichloroethane (40 mL), glacial acetic acid (0.52 mL) and sodium triacetoxyborohydride (3.47 g) was stirred at room temperature for 72 h. The reaction mixture was poured into dichloromethane (50 mL) and saturated Na₂CO₃ (50 mL) and the layers separated. The aqueous layer was extracted with 2×50 mL of dichloromethane and the combined organic layers dried over MgSO₄ and concentrated to dryness under reduced pressure. The crude product was purified by flash column chromatography on silica, eluting with a gradient of ethyl acetate; 0–8% methanol to yield the cis and trans isomers of ethyl 1-[4-(2-keto-1-benzimidazolinyl)piperidin- 1-yl]cyclohexane4-carboxylate as a colorless solid (2.23 g).

Step 2: To a stirred solution of the cis and trans isomers of ethyl 1-[4-(2-keto-1-benzimidazolinyl)piperidin-1-yl] cyclohexane-4-carboxylate (2.16 g) in dry toluene (150 mL) at −90° C. under argon, was added diisobutylaluminum hydride (11.6 mL of a 1.5M solution in toluene). The reaction mixture was stirred at −90° C. for 1 h, then quenched with methanol (1 mL) followed by saturated sodium potassium tartrate (50 mL). The layers were separated, the aqueous layer was extracted with 2×100 mL of ethyl acetate, and the combined organic layers were dried over MgSO₄ and concentrated to dryness under reduced pressure to give the cis and trans isomers of 1-[4-(2-keto- 1-benzimidazolinyl)piperidin-1-yl]cyclohexane-4-carboxaldehyde as a colorless foam (1.82 g).

Step 3: To a stirred solution of 5-bromopyrimidine (3.98 g) in 1:1 diethyl ether; tetrahydrofuran (120 mL) at −110° C. under argon, was added n-butyllithium (10.4 mL of a 1.6M solution in hexanes) at such a rate that the temperature was maintained at −110° C. After stirring for an additional 10 min at this temperature, a solution of the cis and trans isomers of 1-[4-(2-keto-1-benzimidazolinyl)piperidin-1-yl] cyclohexane-4-carboxaldehyde (0.91 g) in tetrahydrofuran (50 mL) was slowly added. The reaction mixture was allowed to warm gradually to room temperature, quenched with 1N NaHCO$_3$ (100 mL), and extracted with 3×150 mL ethyl acetate. The combined extracts were dried over MgSO$_4$ and concentrated under reduced pressure. The residue was taken up in chloroform (200 mL) and extracted with H$_2$O (100 mL) at pH 6. The aqueous layer was then adjusted to pH 11 and extracted with 4×100 mL chloroform and these extracts were dried over Na$_2$SO$_4$ and concentrated under reduced pressure. Silica chromatography, eluting with acetonitrile; 5% NH$_4$OH, yielded 1.0 g of the desired cis and trans isomers. A 100 mg sample of the isomers was purified by normal phase HPLC, eluting with butyl chloride; 19% ethanol; 0.1% triethylamine, gave: 54 mg of (±)-cis-1,3-dihydro-1-(1-{4-[(5-pyrimidinyl)hydroxymethyl]cyclohex-1-yl}piperidin-4-yl)-2H -benzimidazol- 2-one as a colorless solid: $^1$H NMR (400 MHz, CDCl$_3$) 9.71 (br s, 1H), 9.14 (s, 1H), 8.75 (s, 2H), 7.25 (m, 1H), 7.11–7.02 (m, 3H), 4.71 (d, 1H), 4.32 (tt, 1H), 3.20 (m, 2H), 3.15 (br s, 1H), 2.44 (m, 2H), 2.34 (m, 1H), 2.17 (t, 2H), 1.98–1.75 (m, 6H), 1.64–1.49 (m, 3H), 1.42 (m, 1H), 1.30 (m, 1H). The hydrochloride salt was precipitated from ethanol/toluene: analysis calculated for C$_{23}$H$_{29}$N$_5$O$_2$.HCl.1.65 H$_2$O.0.20 C$_6$H$_5$CH$_3$ C: 59.55, H: 7.15, N: 14.23; found C: 59.53, H: 6.85, N: 14.32; and 29 mg of (±)-trans-1,3-dihydro-1-(1-{4-[(5-pyrimidinyl)hydroxymethyl-]cyclohex-1-yl}piperidin-4-yl) -2H-benzimidazol-2-one as a colorless solid: $^1$H NMR (400 MHz, CDCl$_3$) 9.28 (br s, 1H), 9.14 (s, 1H), 8.70 (s, 2H), 7.34 (m, 1H), 7.10–7.01 (m, 3H), 4.54 (d, 1H), 4.33 (tt, 1H), 3.05 (m, 2H), 2.68 (br s, 1H), 2.53–2.35 (m, 5H), 2.07–1.93 (m, 3H), 1.88–1.82 (m, 2H), 1.68–1.58 (m, 2H), 1.37–1.25 (m, 2H), 1.13 (m, 2H). The hydrochloride salt was precipitated from ethanol/toluene: analysis calculated for C$_{23}$H$_{29}$N$_5$O$_2$.1.8 HCl C: 58.39, H: 6.56, N: 14.80; found C: 58.27, H: 6.63, N: 14.98.

EXAMPLE 42 trans-1,3-Dihydro-1-{1-[4-(5-pyrimidinylcarbonyl) cyclohex-1-yl]piperidin-4-yl}-2H-benzimidazol-2-one Step 1: To a stirred solution of oxalyl chloride (68 mg) in dry dichloromethane (4 mL) at −60° C., under argon, was added dry dimethyl sulfoxide (0.107 mL) dropwise. The resulting mixture was stirred for 5 min, then added to a solution of (±)-cis-1,3-dihydro-1-(1-{4-[(5-pyrimidinyl) hydroxymethyl]cyclohex-1-yl}piperidin-4-yl)-2H -benzimidazol-2-one (112 mg) in dichloromethane (5 mL) at −60° C. The reaction mixture was stirred for 20 min at −60° C., then triethylamine (0.54 mL) was added and the solution was allowed to warm to room temperature. Water was added and the mixture stirred for a further 10 min, after which saturated sodium carbonate was added and the mixture was extracted with dichloromethane (3×20 mL). The combined extracts were dried (MgSO$_4$) and concentrated in vacuo. Purification by preparative TLC on silica eluting with chloroform; 7% methanol; 1% NH$_4$OH, followed by a second purification eluting with dichloromethane; 10% methanol; 1% NH$_4$OH yielded trans-1,3-dihydro-1-{1-[4-(5-pyrimidinylcarbonyl)cyclohex-1-yl]piperidin-4-yl}-2H-benzimidazol-2-one: $^1$H NMR (400 MHz, CDCl$_3$; CD$_3$OD) 9.34 (s, 1H), 9.30 (s, 2H), 7.43 (m, 1H), 7.11–7.04 (m, 3H), 4.40 (tt, 1H), 3.36 (m, 1H), 3.28 (d, 2H), 2.73–2.57 (m, 5H), 2.24–2.10 (m, 4H), 1.90 (m, 2H), 1.633 (m, 4H). m/z (FAB): 406 (MH$^+$). The hydrochloride salt was precipitated from ethanol/chloroform: analysis calculated for C$_{23}$H$_{27}$N$_5$O$_2$.2 HCl.0.75 H$_2$O.0.35 C$_2$H$_5$OH C: 56.03, H: 6.47, N: 13.78; found C: 56.03, H: 6.14, N: 13.76.

EXAMPLE 43 cis-1,3-Dihydro-1-{1-[1-(3-pyridylamino)cyclohex-4-yl] piperidin-4-yl}-2H-benzimidazol-2-one and trans-1,3-Dihydro-1-{1-[1-(3-pyridylamino)cyclohex-4-yl]piperidin-4-yl}-2H -benzimidazol-2-one Step 1: A mixture of 1,3-dihydro-1-{1-[4-oxocyclohex-1-yl]piperidin-4-yl}-2H-benzimidazol-2-one (200 mg), 3-aminopyridine (29 mg), 1,2-dichloroethane (1.5 mL), acetic acid (0.087 mL) and sodium triacetoxyborohydride (180 mg) was stirred at room temperature for 20 h. The reaction mixture was poured into saturated aqueous Na$_2$CO$_3$ (10 mL) and extracted with dichloromethane (3×30 mL). The combined organic extracts were dried over MgSO$_4$ and concentrated under reduced pressure. Column chromatography on silica gel, eluting with a gradient of dichloromethane; 0.5% NH$_4$OH; 3–10% methanol gave 83 mg of the desired cis and trans isomers, which were separated by normal phase HPLC (eluting with butyl chloride; 7% methanol; 0.2% triethylamine): cis-1,3-dihydro-1-{1-[1-(3-pyridylamino) cyclohex-4-yl]piperidin-4-yl}-2H-benzimidazol-2-one (34 mg): $^1$H NMR (400 MHz, CDCl$_3$) 10.03 (br s, 1H), 8.05 (d, 1H), 7.94 (d, 1H), 7.29 (dd, 1H), 7.14–7.01 (m, 4H), 6.88 (dd, 1H), 4.37 (tt, 1H), 3.86 (d, 1H), 3.61 (m, 1H), 3.17 (d, 2H), 2.53–2.30 (m, 5H), 2.01–1.84 (m, 4H), 1.78–1.59 (m, 6H). The hydrochloride salt was precipitated from ethanol/ toluene and triturated with diethyl ether: analysis calculated for C$_{23}$H$_{29}$N$_5$O.3 HCl.0.30 (C$_2$H$_5$)$_2$O C: 55.56, H: 6.74, N: 13.39; found C: 55.59, H: 6.73, N: 13.41; trans-1,3-dihydro-1-{1-[1-(3-pyridylamino)cyclohex-4-yl]piperidin-4-yl}-2H-benzimidazol-2-one (10 mg): $^1$H NMR (400 MHz, CDCl$_3$) 9.28 (br s, 1H), 8.01 (d, 1H), 7.93 (d, 1H), 7.32 (m, 1H), 7.09–7.03 (m, 4H), 6.86 (ddd, 1H), 4.36 (tt, 1H), 3.22 (tt, 1H), 3.09 (d, 2H), 2.50–2.39 (m, 5H), 2.23 (d, 2H), 2.00 (d, 2H), 1.86 (m, 2H), 1.47 (q, 2H), 1.21 (q, 2H). The hydrochloride salt was precipitated from methanol/diethyl ether: analysis calculated for C$_{23}$H$_{29}$N$_5$O.3 HCl.0.65 CH$_3$OH C: 54.45, H: 6.68, N: 13.42; found C: 54.44, H: 6.60, N: 13.29.

EXAMPLE 44

(±)-1,3-Dihydro-1-(1-{1-[1-(2-pyrazinyl)-ethyl]piperidin-4-yl}piperidin-4-yl)-2H-benzimidazol-2-one Step 1: Sodium borohydride (0.69 g) was added in portions to a stirred solution of acetylpyrazine (1.49 g) in ethanol (300 mL) at 0° C. The mixture was allowed to warm to room temperature and stirred for 20 min, then water (100 mL) was added and the mixture adjusted to pH 7 with 1N hydrochloric acid. The neutralized solution was concentrated in vacuo to a volume of 200 mL, saturated with sodium chloride, and extracted with ethyl acetate (3×500 mL). The organic extracts were dried (Na$_2$SO$_4$) and concentrated to give a solid which was washed with dichloromethane (4×100 mL). The dichloromethane washings were concentrated to give 2-(1-hydroxyethyl)pyrazine (1.38 g) as a colorless oil.

Step 2: To a stirred solution of 2-(1-hydroxyethyl) pyrazine (0.859 g) and diphenylphosphoryl azide (2.48 g) in dry toluene (12 mL) at 0° C., under argon, was added 1,8-diazabicyclo[5.4.0]undec-7-ene (1.35 mL) dropwise. The resulting mixture was allowed to warm slowly to room temperature and stirred for 22 h then quenched with water (8 mL). The organic layer was removed and the aqueous phase extracted with 10 mL ethyl acetate. The combined extracts were concentrated, and the crude product was purified by flash column chromatography, eluting with hexane; 25% ethyl acetate to give 2-(1-azidoethyl)pyrazine (0.88 g) as a colorless oil.

Step 3: 2-(1-Azidoethyl)pyrazine (0.77 g) and 10% palladium on carbon (0.075 g) were stirred in ethanol (40 mL) under an atmosphere of hydrogen at room temperature for 2 h. The mixture was filtered through a pad of celite and the filtrate concentrated under reduced pressure to yield 2-(1-aminoethyl)pyrazine (0.56 g) as a pale oil Step 4: To a stirred mixture of 2-(1-aminoethyl)pyrazine (225 mg), ethanol (10 mL) and $K_2CO_3$ (72 mg) heated to reflux was added dropwise over 30 min, a solution of 4 g of 1,1-dimethyl-4-oxopiperidinium iodide (2.1 g) in water (36 mL). When the addition was complete, the mixture was heated under reflux for an additional 2 h, cooled, basified to pH 10 with $Na_2CO_3$ and extracted with ethyl acetate (3×100 mL). The combined organic extracts were dried over $MgSO_4$ and concentrated under reduced pressure. Column chromatography over silica gel, eluting with a gradient of ethyl acetate; 0–5% methanol gave 300 mg of 1-(1-(2-pyrazinyl)-ethyl)-4-oxopiperidine as an oil: $^1$H NMR (400 MHz, $CDCl_3$) 8.74 (d, 1H), 8.54 (dd, 1H), 8.48 (d, 1H), 3.94 (q, 1H), 2.89–2.75 (m, 4H), 2.46 (t, 4H), 1.50 (d, 3H).

Step 5: A mixture of 1-(1-(2-pyrazinyl)-ethyl)-4-oxopiperidine (37 mg), 4-(2-oxo-1-benzimidazolinyl)piperidine (41 mg), 1,2-dichloroethane (0.75 mL), glacial acetic acid (0.011 mL) and sodium triacetoxyborohydride (60 mg) was stirred at room temperature for 48 h. The reaction mixture was poured into dichloromethane (5 mL) and saturated aqueous $Na_2CO_3$ (3 mL) and the layers separated. The aqueous layer was extracted with dichloromethane (2×5 mL) and the combined organic layers dried over $Na_2SO_4$ and concentrated under reduced pressure. Purification by preparative TLC, eluting with chloroform; 10% methanol; 1% $NH_4OH$, followed by trituration with diethyl ether gave 35 mg of (±)-1,3-dihydro-1-(1-{1-[1-(2-pyrazinyl)-1-ethyl]piperidin-4-yl}piperidin-4-yl)-2H-benzimidazol-2-one as a colorless solid: $^1$H NMR (400 MHz, $CDCl_3$) 9.77 (br s, 1H), 8.69 (d, 1H), 8.54 (dd, 1H), 8.46 (d, 1H), 7.35 (m, 1H), 7.11–7.03 (m, 3H), 4.39 (m, 1H), 3.73 (q, 1H), 3.11 (m, 3H), 2.90 (m, 1H), 2.35–2.55 (m, 5H), 2.11 (m, 2H), 1.92–1.61 (m, 6H), 1.44 (d, 3H). Analysis calculated for $C_{23}H_{30}N_6O.0.1\ H_2O.0.3\ CHCl_3$: C: 63.01, H: 6.92, N: 18.92 found C: 63.07, H: 6.96, N: 18.76.

EXAMPLE 45

(±) 1,3-Dihydro-1-{1'-[1"-(1'"-(5""-pyridinyl)ethyl)piperidin-4"-yl]piperidin-4'-yl}-2H-benzimidazol-2-one From 3-(1-aminoethyl)pyridine using the procedures described in Example 30 there was obtained 1,3-dihydro-1-{1'-[1"-(1'"-(5""-pyridinyl)-)piperidin-4"-yl]piperidin-4'-yl}-2H-benzimidazol-2-one as a white solid: $^1$H NMR (400 MHz, $CDCl_3$) 8.7 (d, 1H), 8.5 (dd, 1H), 8.2 (br s, 1H), 7.65 (dt, 1H), 7.25–7.32 (br m, 3H), 7.02–7.08 (m, 3H), 4.35 (br m, 1H), 3.55 (q, J=7 Hz, 1H), 3.0–3.1 (m, 3H), 2.85 (m, 1H), 2.3–2.5 (m, 5H), 2.05 (br t, 2H), 1.86 (br m, 4H), 1.6 (br m, 2H), 1.4 (d, J=7 Hz, 3H). The trihydrochloride salt: Analysis calculated for $C_{24}H_{31}N_5O.3\ HCl.2\ H_2O.0.25\ CH_3CH_2OH$: C:52.31, H: 7.20, N: 12.20; found C: 52.61, H: 6.87, N: 11.93.

EXAMPLE 46

(1'"R) 1,3-Dihydro-1-{1'-[1"-(1'"-(5""-pyridinyl)ethyl)piperidin-4"-yl]piperidin-4'-yl}-2H-benzimidazol-2-one Step 1: Sodium borohydride (1.75 g) was added in portions to a stirred solution of acetylpyridine (12.1 g) in ethanol (100 mL) at 0° C. The mixture was allowed to warm to room temperature and stirred for 20 min, then concentrated under reduced pressure to remove ethanol. The thick residue was diluted with 300 mL of dichloromethane, 25 mL of water and 5 mL of 20% NaOH. The aqueous layer was saturated with sodium chloride, and extracted with ethyl acetate (4×150 mL). The combined organic extracts were dried ($MgSO_4$) and concentrated. Evaporative distillation of the crude oily product (14.0 g) at 1 mm, oven temperature 85°–95° C. gave 11.4 g of 3-(1-hydroxyethyl)pyridine as a colorless oil.

Step 2: A mixture of 5 g of 3-(1-hydroxyethyl)pyridine, 80 mL of t-butylmethylether, 0.85 g of lipase from *Pseudomonas fluorescens* on Celite® (30 wt %, prepared as described by D. Bianchi, P. Cesti and E. Battistel, *J. Org. Chem.* 1988, 53, 5531–34) and 2.0 mL of acetic anhydride was allowed to stir in a stoppered flask for 24 h. The mixture was filtered and concentrated under reduced pressure. Low pressure chromatography on silica gel eluting with a gradient of 100% ethyl as acetate to 95:5 ethyl acetate: methanol gave 3.5 g of the acetate of 3-(1'R-hydroxyethyl)pyridine followed by 2.4 g of 3-(1'S-hydroxyethyl)pyridine. The enantiomeric purity assessed by HPLC on Chiracel OD (250×4.6 mm, 0.3% diethylamine in n-butyl chloride, isochratic) was 99%.

Step 3: To a stirred solution of 1.7 g of 3-(1'S-hydroxyethyl)pyridine and 4.7 g of diphenylphosphoryl azide 20 mL of dry tetrahydrofuran cooled to 0° C., was added 3.4 g of 1,8-diazabicyclo[5.4.0]undec-7-ene. The resulting mixture was allowed to warm to room temperature for 48 h., then loaded on a 10×15 cm column of silica gel. Elution with ether give 1.7 g of 3-(1'R-azidoethyl)pyridine as a colorless oil: $[\alpha]_D^{25}$ =+78.6° (c=5.75, MeOH); $^1$H NMR (400 MHz, $CDCl_3$) 8.59 (d, 1H), 8.58 (dd, 1H), 7.68 (dt, 1H), 7.33 (dd, 1H), 4.65 (q, 1H), 1.6 (d, 3H).

Step 4: A mixture of 1.7 g of 3-(1'R-azidoethyl)pyridine, 0.25 g of 5% palladium on carbon and 150 mL of ethanol was stirred under an atmosphere of hydrogen at room temperature for 4 h. The mixture was filtered through a pad of celite and the filtrate concentrated under reduced pressure to yield 1.5 g of 3-(1'R-aminoethyl)pyridine as a pale oil.

Step 5: To a stirred mixture of 1.5 g of 3-(1'R-aminoethyl)pyridine, 50 mL of ethanol and 1.54 g of $K_2CO_3$ heated to reflux was added dropwise over 40 min a solution of 4.5 g of 1-ethyl-1-methyl-4-oxopiperidinium iodide in water (80 mL). When the addition was complete, the mixture was heated under reflux for an additional 30 min, cooled and extracted with 3×100 mL portions of chloroform. The combined organic extracts were dried over $MgSO_4$ and concentrated under reduced pressure. Column chromatography over silica gel, eluting with 50:50 ethyl acetate:tetrahydrofuran gave 1.9 g of 1-(1'R-(3"-pyridinyl)-ethyl)-4-oxopiperidine as an oil: $^1$H NMR (400 MHz, $CDCl_3$) 8.61 (d, 1H), 8.52 (dd, 1H), 7.7 (dt, 1H), 7.28 (dd, 1H), 3.7 (q, 1H), 2.89–2.75 (m, 4H), 2.44 (t, 4H), 1.44 (d, 3H).

Step 6: A mixture of 1-(1'R-(3"-pyridinyl)-ethyl)-4-oxopiperidine (250 mg), 4-(2-oxo-1-benzimidazolinyl)piperidine (530 mg), 1,2-dichloroethane (7 mL), glacial acetic acid (0.2 mL) and sodium triacetoxyborohydride (450 mg) was stirred at room temperature for 48 h. The reaction mixture was partitioned between chloroform (3×50 mL) and saturated aqueous Na₂CO₃ (5 mL) and the combined organic layers dried over MgSO₄ and concentrated under reduced pressure. Chromatography over silica gel, eluting with 95% tetrahydrofuran; 5% conc. NH₄OH, followed by trituration with ethyl acetate gave 280 mg of (1'''R) 1,3-dihydro-1-{1'-[1''-(1'''-(5''''-pyridinyl)-ethyl)piperidin-4''-yl]piperidin-4'-yl}-2H-benzimidazol-2-one as a white solid: $^1$H NMR (400 MHz, CDCl₃) 8.54 (d, 1H), 8.49 (dd, 1H), 8.2 (br s, 1H), 7.65 (dt, 1H), 7.25–7.32 (br m, 3H), 7.02–7.08 (m, 3H), 4.35 (br m, 1H), 3.5 (q, J=7 Hz, 1H), 3.0–3.1 (m, 3H), 2.85 (m, 1H), 2.3–2.5 (m, 5H), 2.05 (br t, 2H), 1.86 (br m, 4H), 1.6 (br m, 2H), 1.39 (d, 3H). The citrate salt: Analysis calculated for $C_{24}H_{31}N_5O.1.5\ C_6H_8O_7$: C: 57.13, H: 6.25, N: 10.10 found C: 57.48, H: 6.39, N: 10.35.

EXAMPLE 47

(1'''R) 1,3-Dihydro-1-{1'-[1''-(1'''-(5''''-pyridinyl)ethyl)piperidin-4''-yl]piperidin-4'-yl}-5-chloro-2H-benzimidazol-2-one From 1-(1'R-(3''-pyridinyl)-ethyl)-4-oxopiperidine using the procedure described in Example 46, but substituting 5-chloro-1-(4-piperidinyl) benzimidazol-2H-one for 1-(4-piperidinyl) benzimidazol-2H-one, there was obtained (1'''R) 1,3-dihydro-1-{1'-[1''-(1'''-(5''''-pyridinyl)ethyl)piperidin-4''-yl]piperidin-4'-yl}-5-chloro-2H-benzimidazol-2-one as a white solid: mp 162°–3° C.; $^1$H NMR (400 MHz, CDCl₃) 9.2 (br s, 1H), 8.56 (d, 1H), 8.51 (dd, 1H), 7.67 (dt, 1H), 7.28 (dd, 1H), 7.21 (d, 1H), 7.09 (d, 1H), 7.02 (dd, 1H), 4.35 (br m, 1H), 3.5 (q, J=7 Hz, 1H), 3.0–3.1 (m, 3H), 2.85 (m, 1H), 2.3–2.5 (m, 5H), 2.05 (br t, 2H), 1.86 (br m, 4H), 1.6 (br m, 2H), 1.4 (d, 3H). The citrate salt: Analysis calculated for $C_{25}H_{33}N_5O.1.0\ C_6H_8O_7.1.0\ CH_3CO_2CH_2CH_3.0.5\ H_2O$: C: 56.00, H: 6.50, N: 9.60 found C: 55.97, H: 6.42, N: 9.61.

EXAMPLE 48

(1'''R) 1,3-Dihydro-1-{1'-[1''-(1'''-(5''''-pyridinyl)ethyl)piperidin-4''-yl]piperidin-4'-yl}-5-methyl-2H-benzimidazol-2-one From 1-(1'R-(3''-pyridinyl)-ethyl)-4-oxopiperidine using the procedure described in Example 46, but substituting 5-methyl-1-(4-piperidinyl) benzimidazol-2H-one for 1-(4-piperidinyl) benzimidazol-2H-one, there was obtained (1'''R) 1,3-dihydro -1-{1'-[1''-(1'''-(5''''-pyridinyl)ethyl)piperidin- 4''-yl]piperidin-4'-yl}-5-methyl-2H-benzimidazol-2-one as a white solid: mp 176°–8° C.; 1H NMR (400 MHz, CDCl₃) 8.54 (d, 1H), 8.49 (dd, 1H), 8.5 (br s, 1H), 7.65 (dt, 1H), 7.25 (dd, 1H), 7.17 (d, 1H), 6.88 (s, 1H), 6.84 (d, 1H), 4.35 (br m, 1H), 3.5 (q, J=7 Hz, 1H), 3.0–3.1 (m, 3H), 2.85 (m, 1H), 2.5–2.3 (m, 5H), 2.36 (s, 3H), 2.05 (br t, 2H), 1.86 (br m, 4H), 1.6 (br m, 2H), 1.4 (d, 3H). The citrate salt: Analysis calculated for $C_{25}H_{33}N_5O.1.0\ C_6H_8O_7.1.0\ H_2O$: C: 59.12, H: 6.88, N: 11.12 found C: 59.47, H: 6.78, N: 10.78.

EXAMPLE 49

(±)-1,3-Dihydro-1-(1-{1-[1-(2-pyrazinyl)-1-ethyl]piperidin-4-yl}piperidin-4-yl)-5-methyl-2H-benzimidazol-2-one From 1-(1-(2-pyrazinyl)-ethyl)-4-oxopiperidine using the procedure described in Example 44, but substituting 5-methyl-1-(4-piperidinyl) benzimidazol-2H-one for 1-(4-piperidinyl) benzimidazol-2H-one, there was obtained (1'''R) 1,3-dihydro-1-{1'-[1''-(1'''-(5''''-pyridinyl)ethyl)piperidin-4''-yl]piperidin-4'-yl}-5-methyl-2H-benzimidazol-2-one as a white solid: $^1$H NMR (400 MHz, CDCl₃) 8.68 (m, 1H), 8.53 (m, 1H), 8.46 (m, 1H), 7.80 (br s, 1H), 7.17 (d, 1H), 6.86 (m, 2H), 4.31 (m, 1H), 3.73 (q, 1H), 3.12–3.03 (m, 3H), 2.87 (d, 1H), 2.43–2.26 (m, 5H), 2.36 (s, 3H), 2.08 (q, 2H), 1.86–1.75 (m, 4H), 1.70–1.52 (m, 2H), 1.43 (d, 3H).

EXAMPLE 50

(±)-1,3-Dihydro-1-(1-{1-[1-(2-pyrazinyl)-1-ethyl]piperidin-4-yl}piperidin-4-yl)-5-chloro-2H-benzimidazol-2-one From 1-(1-(2-pyrazinyl)-ethyl)-4-oxopiperidine using the procedure described in Example 44, but substituting 5-chloro-1-(4-piperidinyl) benzimidazol-2H-one for 1-(4-piperidinyl) benzimidazol-2H-one, there was obtained (1'''R) 1,3-dihydro-1-{1'-[1''-(1'''-(5''''-pyridinyl)ethyl)piperidin- 4''-yl]piperidin-4'-yl}-5-chloro-2H-benzimidazol-2-one as a white solid: $^1$H NMR (400 MHz, CDCl₃) 10.60 (br s, 1H), 8.69 (d, 1H), 8.54 (dd, 1H), 8.46 (d, 1H), 7.21 (d, 1H), 7.12 (d, 1H), 7.00 (dd, 1H), 4.34 (m, 1H), 3.72 (q, 1H), 3.14–3.05 (m, 3H), 2.89 (d, 1H), 2.47–2.33 (m, 5H), 2.10 (m, 2H), 1.90–1.77 (m, 4H), 1.74–1.57 (m, 2H), 1.44 (d, 3H).

EXAMPLE 51

1,3-dihydro-1-(1-{1-[2-(5-pyrimidinyl)-prop-2-yl]piperidin-4-yl}piperidin-4-yl)-2H-benzimidazol-2-one Step 1: To a stirred solution of 4.06 g of 5-pyrimidineacetic acid (F. Zymalkowski and E. Reimann, *Arch. Pharm.* 1966 299 362–7) and triethylamine (6.55 g) in methylene chloride (150 mL) at 0° C. was added ethyl chloroformate (6.38 g) followed by 4-dimethylaminopyridine (0.72 g). The mixture was stirred at 0° C. for 1 h, then the solution was diluted with methylene chloride (200 mL) and saturated ammonium chloride (150 mL) was added. After removal of the organic phase, the aqueous layer was extracted with methylene chloride (2×200 mL) and the combined organic extracts were dried over MgSO₄ and concentrated to give 7.33 g of a crude oil. Purification by column chromatography, eluting with hexane; 50% ethyl acetate gave ethyl 5-pyrimidinylacetate (3.98 g) as a colorless oil.

Step 2: A solution of ethyl 5-pyrimidinylacetate (3.98 g) and iodomethane (17.0 g) in dry THF (200 mL) was added to a solution of lithium bis(trimethylsilyl)amide (60 retool) in dry THF (200 mL) at −70° C. at such a rate that the temperature did not rise above −65° C. The reaction mixture was stirred under argon at −70° C. for 2 h, then allowed to warm to room temperature overnight and quenched with sulfuric acid (2.94 g) in water (100 mL). Saturated ammonium chloride (100 mL) was added, the THF layer was removed, and the aqueous phase was extracted with ethyl acetate (200 mL). The combined organic extracts were dried over MgSO₄ and concentrated to give 4.64 g of ethyl 2-methyl-2-(5-pyrimidinyl)propionate as a colorless oil.

Step 3: A mixture of ethyl 2-methyl-2-(5-pyrimidinyl) propionate (4.64 g), 1.0N lithium hydroxide (26 mL) and THF (100 mL) was heated to reflux under argon for 26 h. The mixture was allowed to cool, adjusted to pH 7 with acetic acid, and concentrated to dryness to give 4.11 g of lithium 2-methyl-2-(5-pyrimidinyl)propionate as a pale solid.

Step 4: A mixture of lithium 2-methyl-2-(5-pyrimidinyl) propionate (4.11 g), diphenylphosphoryl azide (13.2 g), triethylamine (4.86 g) and anhydrous tert-butyl alcohol (100 mL) was heated to reflux for 6 h, then allowed to cool and concentrated in vacuo. The residue was partitioned between chloroform (250 mL) and water (100 mL), and the chloroform was extracted, dried (MgSO$_4$) and evaporated under reduced pressure. Chromatography on silica gel, eluting with chloroform; 5% methanol gave a partially purified sample of 2-(5-pyrimidinyl)-2-propylisocyanate as a colorless oil.

Step 5: The crude 2-(5-pyrimidinyl)-2-propylisocyanate was treated with a mixture of 1.0N sodium hydroxide (26 mL), water (20 mL) and THF (100 mL) at 0° C. for 30 min, then the mixture was poured into ethyl acetate (200 mL) and water (100 mL). The aqueous layer was acidified to pH 5 with 10% citric acid, extracted twice with ethyl acetate, and then adjusted to pH 11, saturated with sodium chloride, and extracted with methylene chloride (3×250 mL). The combined methylene chloride extracts were dried (Na$_2$SO$_4$) and concentrated in vacuo to give 2-(5-pyrimidinyl)-2-propylamine (950 mg) as a colorless oil.

Step 6: To a stirred mixture of 2-(5-pyrimidinyl)-2-propylamine (660 mg), ethanol (9 mL) and K$_2$CO$_3$ (665 mg) heated to reflux was added dropwise over 30 min, a solution of 1,1-dimethyl-4-oxopiperidinium iodide (1.9 g) in water (36 mL). When the addition was complete, the mixture was heated under reflux for an additional 2 h, cooled, basified to pH 10 with Na$_2$CO$_3$ and extracted with ethyl acetate (3 ¥100 mL). The combined organic extracts were dried over MgSO$_4$ and concentrated under reduced pressure. Column chromatography over silica gel, eluting with a methylene chloride; 5% methanol gave 360 mg of 1-(2-(5-pyrimidinyl)-prop-2-yl)-4-oxopiperidine as an oil: $^1$H NMR (400 MHz, CDCl$_3$) 9.13 (s, 1H), 8.95 (s, 2H), 2.79 (t, 4H), 2.44 (t, 4H), 1.47 (s, 6H).

Step 7: A mixture of 1-(2-(5-pyrimidinyl)-prop-2-yl)-4-oxopiperidine (117 mg), 4-(2-oxo-1-benzimidazolinyl) piperidine (128 mg), 1,2-dichloroethane (2.5 mL), glacial acetic acid (0.031 mL) and sodium triacetoxyborohydride (170 mg) was stirred at room temperature for 48 h. The reaction mixture was poured into dichloromethane (15 mL) and saturated aqueous Na$_2$CO$_3$ (8 mL) and the layers separated. The aqueous layer was extracted with dichloromethane (2×15 mL) and the combined organic layers dried over Na$_2$SO$_4$ and concentrated under reduced pressure. Purification by column chromatography, eluting with a gradient of methylene chloride; 0–6% methanol; 1% NH$_4$OH, followed by trituration with diethyl ether gave 104 mg of 1,3-dihydro-1-(1-{1-[2-(5-pyrimidinyl)-prop-2-yl]piperidin-4-yl}piperidin-4-yl)-2H-benzimidazol-2-one as a colorless solid: $^1$H NMR (400 MHz, CDCl$_3$) 10.37 (br s, 1H), 9.10 (s, 1H), 8.88 (s, 2H), 7.30 (m, 1H), 7.12–7.01 (m, 3H), 4.37 (m, 1H), 3.11 (d, 2H), 2.86 (d, 2H), 2.53–2.30 (m, 5H), 2.18 (t, 2H), 1.85 (m, 4H), 1.57 (m, 2H), 1.40 (s, 6H). Treatment with citric acid in ethanol yielded the citrate salt, analysis calculated for C$_{24}$H$_{32}$N$_6$O.0.1 H$_2$O.1.5 C$_6$H$_8$O$_7$: C: 55.78, H: 6.27, N: 11.83 found C: 55.82, H: 6.56, N: 11.68.

EXAMPLE 52

1,3-dihydro-1-(1-{1-[2-(5-pyrimidinyl)-prop-2-yl]piperidin-4-yl}piperidin-4-yl)-5-methyl-2H-benzimidazol-2-one From 1-(1-(2-pyrazinyl)-ethyl)-4-oxopiperidine using the procedure described in Example 51, Step 7, but substituting 5-methyl-1-(4-piperidinyl) benzimidazol-2H-one for 1-(4-piperidinyl) benzimidazol-2H-one, there was obtained 1,3-dihydro-1-(1-{1-[2-(5-pyrimidinyl)prop-2-yl]piperidin-4-yl}piperidin-4-yl)-5-methyl-2H-benzimidazol-2-one as a colorless solid: $^1$H NMR (400 MHz, CDCl$_3$) 10.64 (br s, 1H), 9.10 (s, 1H), 8.89 (s, 2H), 7.17 (d, 1H), 6.95 (s, 1H), 6.82 (d, 1H), 4.35 (m, 1H), 3.11 (d, 2H), 2.85 (d, 2H), 2.51–2.30 (m, 5H), 2.35 (s, 3H), 2.18 (t, 2H), 1.84 (m, 4H), 1.57 (m, 2H), 1.39 (s, 6H).

EXAMPLE 53

1,3-dihydro-1-(1-{1-[2-(5-pyrimidinyl)-prop-2-yl] piperidin-4-yl}piperidin-4-yl)-5-chloro-2H-benzimidazol-2-one From 1-(1-(2-pyrazinyl)-ethyl)-4-oxopiperidine using the procedure described in Example 51, Step 7, but substituting 5-chloro-1-(4-piperidinyl) benzimidazol-2H-one for 1-(4-piperidinyl) benzimidazol-2H-one, there was obtained 1,3-dihydro-1-(1-{1-[2-(5-pyrimidinyl)prop-2-yl]piperidin-4-yl}piperidin-4-yl)-5-chloro-2H-benzimidazol-2-one as a colorless solid: $^1$H NMR (400 MHz, CDCl$_3$) 10.70 (br s, 1H), 9.10 (s, 1H), 8.89 (s, 2H), 7.20 (d, 1H), 7.12 (d, 1H), 6.99 (dd, 1H), 4.33 (m, 1H), 3.11 (m, 2H), 2.86 (d, 2H), 2.46–2.31 (m, 5H), 2.35 (s, 3H), 2.18 (t, 2H), 1.84 (m, 4H), 1.56 (m, 2H), 1.40 (s, 6H).

EXAMPLE 54

1,3-dihydro-5-methyl-1-(1-{1-[2-(3-pyridyl)-prop-2-yl] piperidin-4-yl}piperidin-4-yl)-2H-benzimidazol-2-one Using the procedures described in Example 51, but substituting 3-pyridineacetic acid for 5-pyrimidineacetic acid and 5-methyl-1-(4-piperidinyl) benzimidazol-2H-one for 1-(4-piperidinyl) benzimidazol-2H-one, there was obtained 1,3-dihydro-1-(1-{1-[2-(3-pyridinyl)-prop-2-yl]piperidin-4-yl}piperidin-4-yl)-5-methyl-2H-benzimidazol-2-one as a colorless solid: $^1$H NMR (400 MHz, CDCl$_3$) 10.11 (br s, 1H), 8.76 (d, 1H), 8.46 (dd, 1H), 7.86 (dr, 1H), 7.25–7.17 (m, 2H), 6.93 (s, 1H), 6.84 (d, 1H), 4.35 (m, 1H), 3.12 (d, 2H), 2.87 (d, 2H), 2.51–2.32 (m, 5H), 2.35 (s, 3H), 2.14 (t, 2H), 1.83 (m, 4H), 1.56 (m, 2H), 1.37 (s, 6H).

EXAMPLE 55

1,3-dihydro-(1-{1-[2-(3-pyridyl)-prop-2-yl]piperidin-4-yl}piperidin-4-yl)-2H-benzimidazol-2-one Using the procedures described in Example 51, but substituting 3-pyridineacetic acid for 5-pyrimidineacetic acid there was obtained 1,3-dihydro-1-(1-{1-[2-(3-pyridinyl)-prop-2-yl]piperidin-4-yl}piperidin-4-yl)-2H-benzimidazol-2-one as a colorless solid: $^1$H NMR (400 MHz, CDCl$_3$) 10.35 (br s, 1H), 8.76 (d, 1H), 8.46 (dd, 1H), 7.86 (dt, 1H), 7.32 (m, 1H), 7.23 (dd, 1H), 7.10 (m, 1H), 7.02 (m, 2H), 4.38 (m, 1H), 3.13 (d, 2H), 2.87 (d, 2H), 2.54–2.32 (m, 5H), 2.14 (t, 2H), 1.84 (m, 4H), 1.56 (m, 2H), 1.37 (s, 6H).

EXAMPLE 56

1,3-dihydro-1-{1-[1-(2-phenyl-5-pyrimidinylcarbonyl) piperidin-4-yl]piperidin-4-yl}-2H -benzimidazol-2-one From 1,3-dihydro-1-{1-[1-piperidin-4-yl]piperidin-4-yl}-2H-benzimidazol-2-one dihydrochloride salt and 2-phenyl-5-pyrimidinecarboxylic acid (P. Schenone, L. Sansebastiano and L. Mosti, *J. Heterocyclic Chem.*, 1990, 27, 295–305) using the procedure described for Example 3, there was obtained 1,3-dihydro-1-{1-[1-(2-phenyl-5-pyrimidinylcarbonyl)piperidin-4-yl]piperidin-4-yl}-2H-benzimidazol-2-one as a solid: $^1$H NMR (400 MHz, CDCl$_3$) 8.88 (s, 2H), 8.49 (m, 2H), 8.05 (s, 1H), 7.52 (m, 2H), 7.27 (m, 3H), 7.06 (m, 2H), 4.79 (br s, 1H), 4.34 (m, 1H), 3.90 (s, 1H), 3.09 (d, 4H), 2.66 (t, 1H), 2.43 (m, 1H), 1.87 (m, 5H). The dihydrochloride salt: Analysis calculated for C$_{28}$H$_{30}$N$_6$O$_2$.2 HCl.0.20 CHCl$_3$.0.65 CH$_3$CH$_2$OH: C: 61.85, H: 6.18, N: 14.67 found C: 61.90, H: 6.32, N: 14.68.

EXAMPLE 57

1,3-Dihydro-1-{1-[1-(3-pyridinesulfonyl)piperidin-4-yl]piperidin-4-yl}-2H-benzimidazol-2-one From 1,3-dihydro-1-{1-[1-piperidin-4-yl]piperidin-4-yl}-2H-benzimidazol-2-one dihydrochloride salt and pyridine-3-sulfonylchloride (B. I. Alo, O. B. Familoni, F. Marsais and G. Queguiner, *J. Heterocycl. Chem.* 1992 29 61–4.) using the procedure described for Example 1, Step 4 there was obtained 1,3-dihydro-1-{1-[1-(3-pyridinesulfonyl)piperidin-4-yl]piperidin-4-yl}-2H-benzimidazol-2-one as a white solid: $^1$H NMR (400 MHz, CDCl$_3$) 9.01 (s, 1H), 8.84 (m, 1H), 8.18 (s, 1H), 8.07 (m, 1H), 7.50 (m, 1H), 7.25 (m, 2H), 7.06 (m, 2H), 4.26 (m, 1H), 3.92 (m, 2H), 3.00 (m, 3H), 2.39 (m, 5H), 1.79 (m, 4H), 1.30 (m, 2H), 0.88 (m, 1H). The dihydrochloride salt: Analysis calculated for C$_{22}$H$_{29}$Cl$_2$N$_5$O$_3$S.2 HCl.0.8 C$_7$H$_8$.2.0 H$_2$O C: 53.10, H: 6.36, N: 11.22 found C: 53.02, H: 6.40, N: 11.15.

EXAMPLE 58

1,3-dihydro-1-{1-[1-(2-methyl-5-pyrimidinecarbonyl)piperidin-4-yl]piperidin-4-yl}-2H-benzimidazol-2-one From 1,3-dihydro-1-{1-[1-piperidin-4-yl]piperidin-4-yl}-2H-benzimidazol-2-one dihydrochloride salt and 2-methyl-5-pyrimidinecarboxylic acid (P. Schenone, L. Sansebastiano and L. Mosti, *J. Heterocyclic Chem.*, 1990, 27 , 295–305) using the procedure described for Example 3, them was obtained 1,3-dihydro-1-{1-[1-(2-methyl-5-pyrimidinecarbonyl)piperidin-4-yl]piperidin-4-yl}-2H-benzimidazol-2-one dihydrochloride salt as a solid: $^1$H NMR (400 MHz, d$_6$-DMSO) 8.80 (m, 2H), 7.79 (d, 1H), 7.25 (m, 2H), 7.16 (m, 2H), 4.68 (m, 1H), 4.47 (m, 1H), 4.16 (m, 1H), 2.93 (m, 4H), 2.68 (m, 1H), 2.31 (m, 5H), 1.88 (m, 5H), 1.21 (s, 3H). Analysis calculated for C$_{23}$H$_{28}$N$_6$O$_2$.2 HCl.1.55 CH$_3$CO$_2$CH$_2$CH$_3$.2.5 CH$_3$CH$_2$OH: C: 57.96, H: 8.02, N: 11.86; found C: 57.56, H: 8.11, N: 12.24.

EXAMPLE 59

1,3-Dihydro-1-{1-[1-(5-pyrimidinylmethyl)piperidin-4-yl]piperidin-4-yl}-2H-benzimidazol-2-one From the procedure in Example 8, substituting pyrimidine-5-carboxaldehyde for 3-pyridinecarboxaldehyde (H. Bredereck, G. Simchen, H. Wagner and S. Santos, *Liebigs Ann. Chem.* 1971 766 73–88.) there was obtained 1,3-dihydro-1-{1-[1-(5-pyrimidinylmethyl)piperidin-4-yl]piperidin-4-yl}-2H-benzimidazol-2-one as a white solid: $^1$H NMR (400 MHz, CDCl$_3$) 9.06 (s, 1H), 8.62 (s, 2H), 8.44 (s, 1H), 7.27 (s, 2H), 7.06 (s, 2H), 6.36 (s, 2H), 3.05 (m, 3H), 2.24 (m, 3H), 2.04 (m, 2H), 1.92 (m, 2H), 1.67 (m, 3H), 1.26 (m, 2H), 0.94 (m, 3H). The dihydrochloride salt: Analysis calculated for C$_{22}$H$_{28}$N$_6$O.2HCl.1.3 C$_7$H$_8$.2.0 H$_2$O: C: 60.03, H: 7.35, N: 13.51; found C: 60.07, H: 7.46, N: 13.46.

EXAMPLE 60

1,3-Dihydro-1-{1-[1-(4-imidazolylmethyl)piperidin-4-yl]piperidin-4-yl}-2H-benzimidazol-2-one From the procedure in Example 8, substituting imidazole-4-carboxaldehyde for 3-pyridinecarboxaldehyde there was obtained 1,3-dihydro-1-{1-[1-(4-imidazolylmethyl)piperidin-4-yl]piperidin-4-yl}-2H-benzimidazol-2-one as a white solid: $^1$H NMR (400 MHz, CDCl$_3$) 8.98 (s, 1H), 7.63 (s, 1H), 7.28 (s, 2H), 7.05 (s, 2H), 6.97 (s, 1H), 3.08 (m, 3H), 2.40 (m, 5H), 2.17 (t, 2H), 2.05 (s, 2H), 1.85 (m, 2H), 1.70 (m, 2H), 1.27 (m, 2H), 0.89 (m, 1H). The trihydrochloride salt: Analysis calculated for C$_{21}$H$_{28}$N$_6$O.3HCl.1.7 C$_7$H$_8$.0.1 H$_2$O: C: 49.11, H: 6.88, N: 15.84; found: C: 48.93, H: 6.48, N: 15.48.

EXAMPLE 61

1,3-dihydro-1-{1-[1-(2-amino-5-pyrimidinylcarbonyl)piperidin-4-yl]piperidin-4-yl}-2H-benzimidazol-2-one Step 1: A mixture of 0.65 g of ethyl 2-amino-5-pyrimidinecarboxylate (P. Schenone, L. Sansebastiano and L. Mosti, *J. Heterocyclic Chem.*, 1990, 27, 295–305), 1.7 g of di-tert-butyldicarbonate and 50 mL of dichloromethane was allowed to stir overnight then concentrated under reduced pressure. After drying under vacuum, there was obtained 0.75 g of ethyl 2-tert-butoxycarbonylamino-5-pyrimidinecarboxylate as a solid: $^1$H NMR (400 MHz, CDCl$_3$) 9.23 (s, 2H), 4.42 (q, 2H), 1.5 (s, 9H), 1.45 (t, 3H).

Step 2: A mixture of 200 mg of ethyl 2-tert-butoxycarbonylamino-5-pyrimidinecarboxylate, 125 mg of potassium hydroxide and 15 mL of ethanol was heated to 70° C. for 3 h, cooled and concentrated under reduced pressure. The residue was dissolved in 50 mL of ice water, washed with 50 mL of ether, acidified to pH=3 with conc. HCl and extracted with 3×50 mL of chloroform. The combined organic extracts were dried (MgSO$_4$) and concentrated under reduced pressure. Drying under vacuum gave 156 mg of 2-tert-butoxycarbonylamino-5-pyrimidinecarboxylic acid as a white solid.

Step 3: From 1,3-dihydro-1-{1-[1-piperidin-4-yl]piperidin-4-yl}-2H-benzimidazol-2-one dihydrochloride salt and 2-tert-butoxycarbonylamino-5-pyrimidinecarboxylic acid using the procedure described for Example 3, there was obtained 1,3-dihydro-1-{1-[1-(2-tert-butoxycarbonylamino-5-pyrimidinecarbonyl)piperidin-4-yl]piperidin-4-yl}-2H-benzimidazol-2-one as a solid: $^1$H NMR (400 MHz, CDCl$_3$) 9.95 (m, 1H), 8.81 (s, 2H), 7.28 (m, 2H), 7.08 (m, 2H), 4.77 (s, 1H), 4.35 (m, 1H), 3.80 (s, 1H), 3.12 (m, 4H), 2.88 (m, 1H), 2.68 (m, 1H), 2.45 (m, 5H), 1.92 (m, 5H), 1.50 (s, 3H).

Step 4: The 1,3-dihydro-1-{1-[1-(2-tert-butoxycarbonylamino-5-pyrimidinylcarbonyl)piperidin-4-yl]piperidin-4-yl}-2H-benzimidazol-2-one was dissolved in ethyl acetate, cooled to –50° C. and treated with a stream of HCl gas for 2 min. The reaction mixture was allowed to warm to room temperature and stir for several hours, and then concentrated to dryness under reduced pressure. The product 1,3-dihydro-1-{1-[1-(2-amino-5-pyrimidinecarbonyl)piperidin-4-yl]piperidin-4-yl}-2H-benzimidazol-2-one dihydrochloride salt, was obtained as white solid: Analysis calculated for C$_{22}$H$_{25}$N$_7$O$_2$.2 HCl.1.0 C$_7$H$_8$.3.0 H$_2$O: C: 54.38, H: 6.77, N: 15.31; found C: 54.31, H: 6.48, N: 15.23.

EXAMPLE 62

(1'''R)-1,3-Dihydro-1-{1'-[1''-(1'''-phenylethyl)piperidin-4''-yl]piperidin-4'-yl}-2H-benzimidazol-2-one From (R)-(+)-1-phenethylamine using the procedures described in Example 30 there was obtained (1'''R)-1,3-dihydro-1-{1'-[1''-(1'''-phenylethyl)piperidin-4''-yl]piperidin-4'-yl}-2H-benzimidazol-2-one as a white solid: $^1$H NMR (400 MHz, CDCl$_3$) 9.4 (br s, 1H), 7.65 (dt, 1H), 7.25–7.32 (m, 6H), 7.02–7.08 (m, 3H), 4.35 (br m, 1H), 3.42 (q, 1H), 3.18 (d, 1H), 3.10 (d, 2H), 2.90 (d, 1H), 2.45–2.30 (m, 5H), 1.98 (t, 1H), 1.86 (br m, 4H), 1.8–1.5 (m, 3H), 1.4 (d, 3H). Analysis calculated for C$_{25}$H$_{32}$N$_4$O.0.5 H$_2$O: C: 72.60, H: 8.04, N: 13.55; found: C: 72.54, H: 7.88, N: 13.17.

EXAMPLE 63

(1'''S)-1,3-Dihydro-1-{1'-[1''-(1'''-phenylethyl)piperidin-4''-yl]piperidin-4'-yl}-2H-benzimidazol-2-one From (S)-(–)-1-phenethylamine using the procedures described in Example 30 there was obtained (1'''S)-1,3-dihydro-1-{1'-[1''-(1'''-phenylethyl)piperidin-4''-yl]piperidin-4'-yl}-2H-benzimidazol-2-one as a white solid: $^1$H NMR (400 MHz, CDCl$_3$) 9.4 (br s, 1H), 7.65 (dt, 1H), 7.25–7.32 (m, 6H), 7.02–7.08 (m, 3H), 4.35 (br m, 1H), 3.42 (q, 1H), 3.18 (d, 1H), 3.10 (d, 2H), 2.90 (d, 1H), 2.45–2.30 (m, 5H), 1.98 (t, 1H), 1.86 (br m, 4H), 1.8–1.5 (m, 3H), 1.4 (d, 3H). Analysis calculated for $C_{25}H_{32}N_4O \cdot 0.5\ H_2O \cdot 0.25\ CH_3CH_2OH$: C: 72.82, H: 8.15, N: 13.32; found C: 72.72 H: 7.85, N: 12.97.

EXAMPLE 64

(1'''R)-1,3-Dihydro-1-{1'-[1''-(2'''-hydroxy-1'''-phenylethyl)piperidin-4''-yl]piperidin-4'-yl}-2H-benzimidazol-2-one From (R)-(–)-2-amino-2-phenylethanol using the procedures described in Example 30 there was obtained (1'''R)-1,3-dihydro-1-{1'-[1''-(2'''-hydroxy-1'''-phenylethyl)piperidin-4''-yl]piperidin-4'-yl}-2H-benzimidazol-2-one as a white solid: $^1$H NMR (400 MHz, CDCl$_3$+CD$_3$OD) 7.35 (m, 5H), 7.25 (d, 2H), 7.05 (m, 3H), 4.35 (br m, 1H), 4.0 (dd, 1H), 3.70 (m, 2H), 3.60 (s, 3H), 3.08 (m, 3H), 2.95 (d, 1H), 2.5–2.2 (m, 5H), 1.98–1.7 (m, 5H), 1.55 (m, 1H). Analysis calculated for $C_{25}H_{32}N_4O \cdot 0.25\ H_2O$: C: 70.64, H: 7.71, N: 13.18; found C: 70.43, H: 7.57, N: 12.99.

EXAMPLE 65

(1'''S)-1,3-Dihydro-1-{1'-[1''-(2'''-hydroxy-1'''-phenylethyl)piperidin-4''-yl]piperidin-4'-yl}-2H-benzimidazol-2-one From (S)-(+)-2-amino-2-phenylethanol using the procedures described in Example 30 there was obtained (1'''R)-1,3-dihydro-1-{1'-[1''-(2'''-hydroxy-1'''-phenylethyl)piperidin-4''-yl]piperidin-4'-yl}-2H-benzimidazol-2-one as a white solid: $^1$H NMR (400 MHz, CDCl$_3$+CD$_3$OD) 7.35 (m, 5H), 7.25 (d, 2H), 7.05 (m, 3H), 4.35 (br m, 1H), 4.0 (dd, 1H), 3.70 (m, 2H), 3.60 (s, 3H), 3.08 (m, 3H), 2.95 (d, 1H), 2.5–2.2 (m, 5H), 1.98–1.7 (m, 5H), 1.55 (m, 1H). Analysis calculated for $C_{25}H_{32}N_4O \cdot 0.25\ H_2O$: C:70.64, H: 7.71, N: 13.18; found C: 70.76, H: 7.62, N: 12.96.

EXAMPLE 66

1,3-Dihydro-1-{1-[trans-4-hydroxycyclohex-1-yl]piperidin-4-yl}-2H-benzimidazol-2-one Step 1: To a stirred solution of 1,3-dihydro-1-{1-[4-oxocyclohex-1-yl]piperidin-4-yl}-2H-benzimidazol-2-one (100 mg) in methanol (4 mL) at 0° C., under nitrogen, was added tert-butylamine-borane (28 mg). The reaction mixture was stirred at 0° C. for 1 h, then quenched with water (2 mL) and concentrated to remove the methanol. The resulting oil was dissolved in ethyl acetate (50 mL) and the organic solution was washed with saturated sodium carbonate (10 mL), then water (10 mL), then brine (10 mL) and then dried over sodium sulfate. Concentration under reduced pressure yielded trans-1,3-dihydro-1-{1-[4-hydroxycyclohex-1-yl]piperidin-4-yl}-2H-benzimidazol-2-one (75 mg) as a colorless solid: $^1$H NMR (400 MHz, CD$_3$OD) 7.42 (m, 1H), 7.04 (m, 3H), 4.28 (m, 1H), 3.50 (m, 1H), 3.09 (m, 2H), 2.45 (m, 5H), 2.03–1.94 (m, 4H), 1.78–1.75 (m, 2H), 1.44–1.26 (m, 4H). The hydrochloride salt was precipitated from diethyl ether/chloroform: analysis calculated for $C_{18}H_{25}N_3O_2 \cdot HCl \cdot 0.50\ H_2O \cdot 0.70\ CHCl_3$ C: 50.54, H: 6.28, N: 9.45; found C: 50.54, H: 6.19, N: 9.64.

EXAMPLE 67 cis-1,3-Dihydro-1-{1-[4-hydroxycyclohex-1-yl]piperidin-4-yl}-2H-benzimidazol-2-one Step 1: To a stirred solution of 1,3-dihydro-1-{1-[4-oxocyclohex-1-yl]piperidin-4-yl}-2H-benzimidazol-2-one (100 mg) in dry tetrahydrofuran (25 mL) at –78° C., under nitrogen, was added L-Selectride (0.385 mL of a 1.0M solution in tetrahydrofuran). The reaction mixture was stirred at –78° C. for 30 min, then quenched with water (3 mL). The solution was allowed to warm to room temperature and ethyl acetate (50 mL) was added. The organic layer was washed with saturated sodium carbonate (10 mL), then water (10 mL), then brine (10 mL) and then dried over sodium sulfate. Concentration under reduced pressure yielded cis-1,3-dihydro-1-{1-[4-hydroxycyclohex-1-yl]piperidin-4-yl}-2H-benzimidazol-2-one (43 mg) as a colorless solid: $^1$H NMR (400 MHz, CD$_3$OD) 7.42 (m, 1H), 7.05 (m, 3H), 4.32 (m, 1H), 3.94 (m, 1H), 3.17 (m, 2H), 2.53 (m, 5H), 1.88–1.71 (m, 8H), 1.59–1.53 (m, 2H). The hydrochloride salt was precipitated from diethyl ether/methylene chloride: analysis calculated for $C_{18}H_{25}N_3O_2 \cdot HCl \cdot 0.70\ H_2O$ C: 59.48, H: 7.32, N: 11.56; found C: 59.46, H: 7.28, N: 11.23.

EXAMPLE 68

Radioligand Binding Studies

The affinity of muscarinic antagonists for m1–m5 receptors expressed in chinese hamster ovary cells (CHO) were determined using the technique described by Dorje et al., J. Pharmacol. Exp. Ther. 256: 727–733 (1991).

When 80–100% confluent, CHO cells were harvested, and transferred to centrifuge tubes containing CHO buffer (20 mM HEPES at pH 7.4 containing 5 mM MgCl$_2$). The cells were homogenized using a Brinkman Polytron homogenizer for 30 seconds at a setting of 5, on ice. The homogenate was centrifuged at 40,000×g for 15 minutes at 4° C. in a Beckman J2-21M centrifuge. The supernatant was discarded and the homogenization/centrifugation step repeated once. Pelleted membranes were resuspended in CHO buffer to a concentration of one flask harvested (75 cm$^2$) per mL of buffer, mixed well and aliquoted in cryovials (1 mL/vial). The vials were stored at –70° C. until used in the assay. The binding incubation was done in polypropylene macrowell tube strips in a final volume of 0.5 mL of HEPES buffer (20 mM; pH 7.4 containing 5 mM MgCl$_2$) containing 0.1 mL of cell membrane suspension, 3H-N-methylscopolamine (NEN Corporation, NET-636, 70–87 C$_i$/mmole) at a final concentration of approximately 0.2 nM and the competing drug in a varying range of concentrations or vehicle. After the addition of the cell homogenate the tubes were agitated on a vortex mixer and then placed in a water bath at 32° C. After 90 minutes of incubation, the membranes were harvested on a Skatron filtermat (#11734) or a Wallac filtermat (#205–404) using three washes of HEPES buffer (4° C.). The radioactivity on the filters was counted in a Packard 2200CA scintillation counter or in a Wallac 1205 Betaplate scintillation counter. Specific binding was defined as the difference in binding observed in the presence and absence of 10 micromolar atropine and accounted for at least 80% of total binding. K$_i$ values were calculated using the program LIGAND. Compounds displayed K$_i$ values at m1, m2 and m4 in the range of 1 nM to 5,000 nM. All compounds described herein displayed typically greater than 300-fold less potency at the m3 receptor subtype, in the range of 300 nM to 114,000 nM.

EXAMPLE 69 m1 receptor antagonist activity on the rabbit vas deferens

The technique described by Feifel et al., Brit. J. Pharmacol. 99: 455–460 (1990) was used as follows: Male Hazelton New Zealand White rabbits weighing 1.5–3 kg, are euthanized (phenobarbital sodium, 85 mg/kg. i. v.). An abdominal incision is made and the vas deferens are removed. The tissues are placed in a Petri dish containing oxygenated Krebs solution [NaCl, 118 mM; KCl, 4.7 mM; $CaCl_2$, 2.5 mM; $KH_2PO_4$, 1.2 mM; $MgSO_4$, 1.2 mM; $NaHCO_3$, 25 mM; dextrose, 11 mM] warmed to 30° C. Each tissue is cut into three 2-cm segments: proximal to the prostate, a middle section, and distal to the prostate. Only the first two segments are used. Tissue segments are attached to platinum electrodes with 4-0 surgical silk and placed in a 10 mL jacketed tissue bath containing Krebs buffer at 30° C., bubbled with 5% $CO_2$/95% $O_2$. The tissues are connected to a Statham-Gould force transducer; 0.75 gram of tension is applied and the tissues are electrically stimulated. [EFS parameters are 0.05 Hz; 0.5 ms duration; voltage is set to 30% of 50 V at 25 ohms and increased until a supramaximal voltage is achieved.] The contractions are recorded on a Gould strip chart recorder. The tissues are washed every 20 minutes and allowed to equilibrate. A concentration response curve to the selective m1 receptor agonist McN-A-343 is determined. Tissues are washed every 20 minutes for 60 minutes. The vehicle or compound is added to the bath and the tissues are incubated for 30 minutes, then the McN-A-343 concentration response is repeated. $EC_{50}$ values are determined for both vehicle and tissues treated with the compound before and after treatment. Antagonist dissociation constants ($K_b$) are calculated by the dose-ratio method. Compounds displayed $K_b$ values at m1 generally consistent with the radioligand binding assay described in Example 30 in the range of 5 to 100 nM.

EXAMPLE 70 m2 receptor antagonist activity on the guinea pig left atria

The technique described by Feifel et al., Brit. J. Pharmacol. 99: 455–460 (1990) was used as follows: Duncan-Hartley guinea pigs (Hazelton) weighing 300–600 g, are asphyxiated with $CO_2$. The abdomen is opened and the left atria is rapidly removed. The tissues are placed in a Petri dish containing oxygenated Krebs solution [NaCl, 118 mM; KCl, 4.7 mM; $CaCl_2$, 2.5 mM; $KH_2PO_4$, 1.2 mM; $MgSO_4$, 1.2 mM; $NaHCO_3$, 25 mM; dextrose, 11 mM] warmed to 37° C. Each atria is attached to platinum electrodes with 4-0 surgical silk and placed in a 10 mL jacketed tissue bath containing Krebs buffer at 37° C., bubbled with 5% $CO_2$/ 95% $O_2$. The tissues are connected to a Statham-Gould force transducer; 0.75 gram of tension is applied and the tissues are electrically stimulated. [EFS parameters are 3 Hz; 4 ms duration; voltage is set to 5 V.] The contractions are recorded on a Gould strip chart recorder. The tissues are washed every 20 minutes and allowed to equilibrate. A concentration response curve to the agonist carbachol is determined. Tissues are washed every 20 minutes for 60 minutes. The vehicle or compound is added to the bath and the tissues are incubated for 30 minutes, then the carbachol concentration response is repeated. $EC_{50}$ values are determined for both vehicle and compound treated tissues before and after treatment. Antagonist dissociation constants ($K_b$) are calculated by the dose-ratio method. Compounds displayed $K_b$ values at M2 generally consistent with the radioligand binding assay described in Example 30 in the range of 5 to 100 nM.

EXAMPLE 71

M3 receptor antagonist activity on the guinea pig ileum longitudinal muscle

The technique described by Feifel et al., Brit. J. Pharmacol. 99: 455–460 (1990) was used as follows: Duncan-Hartley guinea pigs (Hazelton) weighing 300–600 g, are asphyxiated with $CO_2$. The abdomen is opened and the caecum and the distal end of the ileum are identified. The ileum is removed and 5 cm of the terminal end (proximal to the caecum) is discarded. The lumen of the remainder is flushed with oxygenated Krebs solution [NaCl, 118 mM; KCl, 4.7 mM; $CaCl_2$, 2.5 mM; $KH_2PO_4$, 1.2 mM; $MgSO_4$, 1.2 mM; $NaHCO_3$, 25 mM; dextrose, 11 mM] warmed to 30° C. The ileum is cut into 2.5 cm segments and each segment is mounted on a glass pipette. A scalpel is used to lightly cut the surface of the tissue and a cotton swab used to tease the longitudinal muscle free from the underlying circular muscle. Longitudinal muscle segments are attached to glass tissue holders with 4-0 surgical silk and placed in a 10 mL jacketed tissue bath containing Krebs buffer at 30° C., bubbled with 5% $CO_2$/95% $O_2$. The tissues are connected to a Statham-Gould force transducer. One gram of tension is applied and the contractions are recorded on a Gould strip chart recorder. The tissues are washed every 20 minutes and allowed to equilibrate. A concentration response curve to the agonist carbachol is determined. Tissues are washed every 20 minutes for 60 minutes. The vehicle or compound is added to the bath and the tissues are incubated for 30 minutes, then the carbachol concentration response is repeated. $EC_{50}$ values are determined for both vehicle and tissues treated with the compound before and after treatment. Antagonist dissociation constants ($K_b$) are calculated by the dose-ratio method. Compounds displayed $K_b$ values at M3 generally consistent with the radioligand binding assay described in Example 30 in the range of 3900 to 24000 nM.

EXAMPLE 72 m1 and m3 receptor antagonist activity on the human muscarinic receptors expressed in CHO cells Preconfluent CHO cells were labeled for 24 hours with 4 $\mu C_i$/mL of [$^3H$] myo-inositol (specific activity 15–20 $C_i$/mmole). The cells were detached from flasks using 1 mM EDTA in phosphate buffer saline, centrifuged for 5 minutes at 200×g, and resuspended in assay buffer (116 mM NaCl; 10 mM LiCl; 4.7 mM KCl; 1.2 mM $MgSO_4$; 2.5 mM $CaCl_2$; 1.2 mM $KH_2PO_4$; 5 mM $NaHCO_3$; 11 mM dextrose, 20 mM HEPES; pH 7.4 at 37° C.) to the desired volume. Four hundred microliters of the cell suspension (approximately $2 \times 10^6$ cells) was added to tubes containing buffer or compound and left at room temperature for 30 minutes. Muscarinic agonist (carbachol) was then added and the cells incubated for 30 minutes at 37° C. The reaction was stopped using an acid solution (12% perchloric acid/3 mM EDTA/1 mM diethylenetriamine pentaacetic acid) and the tubes placed on ice for 15 minutes. The samples were then neutralized with 3M KOH/0.25 M2-(N-morpholino)ethane sulfonic acid/0.25 M3-(N-morpholino) propane sulfonic acid and centrifuged at 3000×g for 15 minutes. Five hundred microliters of each supernatant was diluted to 5.5 mL with water and the entire tube contents applied to anion exchange columns. The columns are sequentially washed with 5 mL of $H_2O$, 15 mL of 60 mM ammonium formate/5 mM borax and 8 mL of 200 mM ammonium formate/5 mM borax. The radioactivity in the last eluate was determined by liquid scintillation counting and taken as the amount of [$^3H$]-inositol monophosphate formed during the incubation. Two different types of experiments were performed: $IC_{50}$ values for compounds where calculated using a fixed concentration of carbachol, or $K_b$ values were generated by performing carbachol concentration-response curves in the absence and presence of a fixed concentration of compound. Compounds displayed $K_b$ values at m1 and m3 generally consistent with the radioligand binding assay described in Example 30 in the range of 1 to 100 nM at m1 and 4,000 to 20,000 at m3.

EXAMPLE 73 m2 receptor antagonist activity on the human muscarinic receptors expressed in CHO cells Preconfluent CHO cells were harvested using 1 mM EDTA in phosphate buffer saline and washed one time by centrifugation in a HEPES buffered physiological salt solution. The cell concentration was adjusted to $3.3 \times 10^6$ cells/mL in the HEPES buffer containing 1.3 micromolar isobutylmethylxanthine. Three hundred microliters of the cell suspension was added to tubes containing compound and incubated for 15 minutes at room temperature. Muscarinic agonist (50 microliters of carbachol; 1 micromolar final concentration) was then added followed by 20 microliters of 200 μM forskolin and the tubes were incubated at 30° C. for an additional 15 minutes. The reaction was stopped by placing the tubes in boiling water for 5 minutes. The tubes were cooled on ice and then centrifuged at 12,000×g for 10 minutes. Fifty microliters of each supernatant was then analyzed for cAMP using a commercially available radioimmunoassay kit following the manufacturer's instructions. Two different types of experiments were performed: $IC_{50}$ values for compounds where calculated using a fixed concentration of carbachol, or $K_b$ values were generated by performing carbachol concentration-response curves in the absence and presence of a fixed concentration of compound. Compound displayed $K_b$ values at m2 generally consistent with the radioligand binding assay described in Example 30 in the range of 1 to 100 nM.

What is claimed is:

1. A compound of structural formula I;

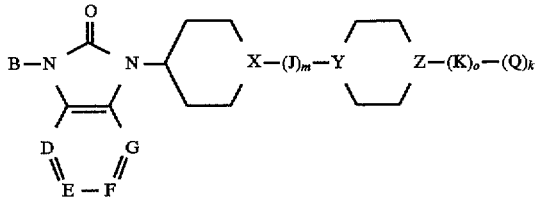

wherein;

C is carbon;

H is hydrogen;

N is nitrogen;

O is oxygen;

S is sulfur;

P is phosphorus;

X and Y are independently N or CH;

Z is N;

J is NB or $CB_2$;

K is NB, $CB_2$, O, carbonyl, thiocarbonyl, sulfonyl, phosphonyl, NBCO, $NBCO_2$, $NBCB_2$, $COCB_2$, CONB, $CO_2$, $CO_2B$, $NB_2$, $NBCONB_2$, $CB_2COCB_2$, $CB_2CONB$, $NBCOCB_2$ or OB;

m and o are 0, 1 or 2;

k is 1 or 2;

B is H, Me, Et, Pr, iPr, $CH_2OH$, $CO_2Me$, $CO_2Et$, $CH_2CH_2OH$, $CONH_2$, OH, $NH_2$, NHMe, OMe, OEt, CONHMe or $CONMe_2$;

Q is phenyl or heterocycle ring unsubstituted or substituted with Me, Et, Pr, Bu, hydroxyl, alkoxy, F, Cl, Br, I alkylsulfonyl, phenyl or heterocyclic; and D,E,F and G are chosen from:

| D | E | F | G |
|---|---|---|---|
| —S— | | CR | CR |
| CR | —S— | | CR |
| CR | CR | CR | CR |
| CR | CR | —S— | |
| —O— | | CR | CR |
| CR | —O— | | CR and |
| CR | CR | | —O— | wherein:

R is H, small alkyl, branched alkyl, halo, alkoxy, OH, amino, dialkylamino or alkylamino.

2. Compounds of claim 1, wherein X=N, Y=CH, m=o, B=H and D, E, F and G are CR.

3. The compound of claim 1 which is 1,3-dihydro-1-{1-[1-(4-nitrobenzoyl)piperidin-4-yl]piperidin-4-yl}-2H-benzimidazol-2-one, 1,3-dihydro-1-{1-[1-(3-nitrobenzoyl)piperidin-4-yl]piperidin-4-yl}-2H-benzimidazol-2-one, 1,3-dihydro-1-{1-[1-benzyl-4-piperidinyl]piperidin-4-yl}-2H-benzimidazol-2-one, 1,3-dihydro-1-{1-[1-(3-pyridinecarbonyl)piperidin-4-yl]piperidin-4-yl}-2H-benzimidazol-2-one, 1,3-dihydro-1-{1-[1-(2-pyridinecarbonyl)piperidin-4-yl]piperidin-4-yl}-2H-benzimidazol-2-one, 1,3-dihydro-1-{1-[1-(4-pyridinecarbonyl)piperidin-4-yl]piperidin-4-yl}-2H-benzimidazol-2-one, 1,3-dihydro-1-{1-[1-benzoylpiperidin-4-yl]piperidin-4-yl}-2H-benzimidazol-2-one, 1,3-dihydro-1-{1-[1-(3-pyridinecarbonyl)-4-piperidinylmethyl]piperidin-4-yl}-2H-benzimidazol-2-one, 1,3-dihydro-1-{1-[1-(4-pyridinecarbonyl)-4-piperidinylmethyl]piperidin-4-yl}-2H-benzimidazol-2-one, 1,3-dihydro-1-{1-[1-(2-furoyl)piperidin-4-yl]piperidin-4-yl}-2H-benzimidazol-2-one, 1,3-dihydro-1-{1-[1-(3,5-dichlorobenzoyl)piperidin-4-yl]piperidin-4-yl}-2H-benzimidazol-2-one, 1,3-dihydro-1-{1-[1-(2,3,4,5,6-pentafluorobenzoyl)piperidin-4-yl]piperidin-4-yl}-2H-benzimidazol-2-one, 1,3-dihydro-1-{1-[1-(3-benzo[b]thiophenecarbonyl)piperidin-4-yl]piperidin-4-yl}-2H-benzimidazol-2-one, 1,3-dihydro-1-{1-[1-(5,6-dichloro-3-pyridinecarbonyl)piperidin-4-yl]piperidin-4-yl}-2H-benzimidazol-2-one, 1,3-dihydro-1-{1-[1-(2-benzofurancarbonyl)piperidin-4-yl]piperidin-4-yl}-2H-benzimidazol-2-one, 1,3-dihydro-1-{1-[trans-1-benzyloxycarbonylamino-4-cyclohexylmethyl]piperidin-4-yl}-2H-benzimidazol-2-one, 1,3-dihydro-1-{1-[trans-1-phthalimido-4-cyclohexylmethyl]piperidin-4-yl}-2H-benzimidazol-2-one, 1,3-dihydro-1-{1-[trans-4-phthalimidomethyl-1-cyclohexyl]piperidin-4-yl}-2H-benzimidazol-2-one, 1,3-dihydro-1-{1-[1-(2-napthyl)piperidin-4-yl]piperidin-4-yl}-2H-benzimidazol-2-one,
1,3-dihydro-1-{1-[1-(3,4-dichlorobenzoyl)piperidin-4-yl]piperidin-4-yl}-2H-benzimidazol-2-one,
1,3-dihydro-1-{1-[1-(2-methoxybenzoyl)piperidin-4-yl]piperidin-4-yl}-2H-benzimidazol-2-one,
1,3-dihydro-1-{1-[1-(3-chloro-2-benzo[b]thiophenecarbonyl)piperidin-4-yl]piperidin-4-yl}-2H-benzimidazol-2-one,
1,3-dihydro-1-{1-[1-(2,4,6-trichlorobenzoyl)piperidin-4-yl]piperidin-4-yl}-2H-benzimidazol-2-one,
1,3-dihydro-1-{1-[1-(5-isoxazolyl)piperidin-4-yl]piperidin-4-yl}-2H-benzimidazol-2-one,
1,3-dihydro-1-{1-[1-(3,5-dimethyl-4-isoxazolyl)piperidin-4-yl]piperidin-4-yl}-2H-benzimidazol-2-one,
1,3-dihydro-1-{1-[trans-1-(4-nitrobenzamido)-4-cyclohexylmethyl]piperidin-4-yl}-2H-benzimidazol-2-one,
1,3-dihydro-1-{1-[trans-4-ethoxycarbonyl-1-cyclohexyl]piperidin-4-yl}-2H-benzimidazol-2-one,
1,3-dihydro-1-{1-[1-(4-nitrobenzyl)-4-piperidinyl]piperidin-4-yl}-2H-benzimidazol-2-one,
1,3-dihydro-1-{1-[1-(benzyloxycarbonyl)piperidin-4-yl]piperidin-4-yl}-2H-benzimidazol-2-one,
1,3-dihydro-1-{1-[trans-4-hydroxymethyl-1-cyclohexyl]piperidin-4-yl}-2H-benzimidazol-2-one,
1,3-dihydro-1-{1-[1-(4-fluorobenzoyl)piperidin-4-yl]piperidin-4-yl}-2H-benzimidazol-2-one,
1,3-dihydro-1-{1-[1-(4-bromobenzoyl)piperidin-4-yl]piperidin-4-yl}-2H-benzimidazol-2-one,
1,3-dihydro-1-{1-[1-(4-iodobenzoyl)piperidin-4-yl]piperidin-4-yl}-2H-benzimidazol-2-one,
1,3-dihydro-1-{1-[1-(3,4-dimethoxybenzoyl)piperidin-4-yl]piperidin-4-yl}-2H-benzimidazol-2-one,
1,3-dihydro-1-{1-[1-(5-nitro-2-pyridinecarbonyl)piperidin-4-yl]piperidin-4-yl}-2H-benzimidazol-2-one,
1,3-dihydro-1-{1-[trans-1-phthalimido-4-cyclohexyl]piperidin-4-yl}-2H-benzimidazol-2-one,
1,3-dihydro-1-{1-[1-(2-methoxy-4-amino-5-chlorobenzoyl)piperidin-4-yl]piperidin-4-yl}-2H-benzimidazol-2-one,
1,3-dihydro-1-{1-[1-(4-dimethylaminobenzoyl)piperidin-4-yl]piperidin-4-yl}-2H-benzimidazol-2-one,
1,3-dihydro-1-{1-[1-(2-nitrobenzoyl)piperidin-4-yl]piperidin-4-yl}-2H-benzimidazol-2-one,
1,3-dihydro-1-{1-[1-(4-cyanobenzoyl)piperidin-4-yl]piperidin-4-yl}-2H-benzimidazol-2-one,
1,3-dihydro-1-{1-[1-(4-methoxycarbonylbenzoyl)piperidin-4-yl]piperidin-4-yl}-2H-benzimidazol-2-one,
1,3-dihydro-1-{1-[1-(3-(3-pyridyl)acrylyl)piperidin-4-yl]piperidin-4-yl}-2H-benzimidazol-2-one,
1,3-dihydro-1-{1-[1-(6-nitro-3-pyridinecarbonyl)piperidin-4-yl]piperidin-4-yl}-2H-benzimidazol-2-one,
1,3-dihydro-1-{1-[1-(3-methyl-2-pyrazolin-1-yl)piperidin-4-yl]piperidin-4yl}-2H-benzimidazol-2-one,
1,3-dihydro-1-{1-[1-(6-quinolinecarbonyl)piperidin-4-yl]piperidin-4-yl}-2H-benzimidazol-2-one,
1,3-dihydro-1-{1-[1-(4-acetylbenzoyl)piperidin-4-yl]piperidin-4-yl}-2H-benzimidazol-2-one,
1,3-dihydro-1-{1-[1-(4-methoxybenzoyl)piperidin-4-yl]piperidin-4-yl}-2H-benzimidazol-2-one,
1,3-dihydro-1-{1-[1-(2-phenylbenzoyl)piperidin-4-yl]piperidin-4-yl}-2H-benzimidazol-2-one,
1,3-dihydro-1-{1-[1-(2-methyl-3-pyridinecarbonyl)piperidin-4-yl]piperidin-4-yl}-2H-benzimidazol-2-one,
1,3-dihydro-1-{1-[1-(6-amino-3-pyridinecarbonyl)piperidin-4-yl]piperidin-4-yl}2H-benzimidazol-2-one,
1,3-dihydro-1-{1-[1-(2-quinolinecarbonyl)piperidin-4-yl]piperidin-4-yl}-2H-benzimidazol-2-one,
1,3-dihydro-1-{1-[1-(5-phenyl-3-pyridinecarbonyl)piperidin-4-yl]piperidin-4-yl}-2H-benzimidazol-2-one,
1,3-dihydro-1-{1-[1-(6-methyl-3-pyridinecarbonyl)piperidin-4-yl]piperidin-4-yl}-2H-benzimidazol-2-one,
1,3-dihydro-1-{1-[1-(6-(4-morpholinyl)-3-pyridinecarbonyl)piperidin-4-yl]piperidin-4-yl}-2H-benzimidazol-2-one,
1,3-dihydro-1-{1-[1-(3-pyridylmethyloxycarbonyl)piperidin-4-yl]piperidin-4-yl}-2H-benzimidazol-2-one,
1,3-dihydro-1-{1-[1-(3-pyridylacetyl)piperidin-4-yl]piperidin-4-yl}-2H-benzimidazol-2-one,
1,3-dihydro-1-{1-[1-(4-methyl-3-pyridinecarbonyl)piperidin-4-yl]piperidin-4-yl}-2H-benzimidazol-2-one,
1,3-dihydro-1-{1-[1-(4-pyridylacetyl)piperidin-4-yl]piperidin-4-yl}-2H-benzimidazol-2-one,
1,3-dihydro-1-{1-[1-(5-methyl-3-pyridinecarbonyl)piperidin-4-yl]piperidin-4-yl}-2H-benzimidazol-2-one,
1,3-dihydro-1-{1-[1-(3-pyridylmethylaminocarbonyl)piperidin-4-yl]piperidin-4-yl}-2H-benzimidazol-2-one,
1,3-dihydro-1-{1-[1-(2R-(1,1-dimethylethoxycarbonylamino)-3-(3-pyridyl)propionyl)piperidin-4-yl]piperidin-4-yl}-2H-benzimidazol-2-one,
1,3-dihydro-1-{1-[1-(2S-(1,1-dimethylethoxycarbonylamino)-3-(3-pyridyl)propionyl)piperidin-4-yl]piperidin-4-yl}-2H-benzimidazol-2-one,
1,3-dihydro-1-{1-[1-(4-pyridylthioacetyl)piperidin-4-yl]piperidin-4-yl}-2H-benzimidazol-2-one,
(4'''R,5'''S) and (4'''S,5'''R) 1,3-dihydro-1-(1'-(1''-(1'''-methyl-2'''-oxo-5'''-(3''''-pyridyl)-4'''-pyrrolidinecarbonyl)piperidin-4''-yl)piperidin-4'-yl)-2H-benzimidazol-2-one,
1,3-dihydro-1-{1-[1-(5-pyrimidinecarbonyl)piperidin-4-yl]piperidin-4-yl}-2H-benzimidazol-2-one,
1,3-dihydro-1-{1-[1-(2S-amino-3-(3-pyridyl)propionyl)piperidin-4-yl]piperidin-4-yl}-2H-benzimidazol-2-one,
1,3-dihydro-1-[1-}1-(2R-amino-3-(3-pyridyl)propionyl)piperidin-4-yl]piperidin-4-yl}-2H-benzimidazol-2-one,
1,3-dihydro-1-{1-[1-(2-pyrazinecarbonyl)piperidin-4-yl]piperidin-4-yl}-2H-benzimidazol-2-one,
1,3-dihydro-1-{1-[1-(3-pyridyloxyacetyl)piperidin-4-yl]piperidin-4-yl}-2H-benzimidazol-2-one,
1,3-dihydro-1-{1-[1-(3-(3-pyridyl)propionyl)piperidin-4-yl]piperidin-4-yl}-2H-benzimidazol-2-one,
1,3-dihydro-1-{trans-4-[4-(3-pyridinecarbonyl)piperazin-1-yl]-1-cyclohexyl}-2H-benzimidazol-2-one,
1,3-dihydro-1-{1-[1-(5-pyrimidinecarbonyl)piperidin-4-yl]piperidin-4-yl}-1H-3,4-dihydroquinazolin-2-one,
1,3-dihydro-1-{1-[1-(4-pyridylsulfonyl)acetyl)piperidin-4-yl]piperidin-4-yl}-2H-benzimidazol-2-one,
1,3-dihydro-1-{1-[1-(3-amino-2-pyrazinecarbonyl)piperidin-4-yl]piperidin-4-yl}-2H-benzimidazol-2-one,
1,3-dihydro-1-{1-[1-(4-pyrimidinecarbonyl)piperidin-4-yl]piperidin-4-yl}-2H-benzimidazol-2-one,
1,3-dihydro-1-{1-[1-(4-imidazolecarbonyl)piperidin-4-yl]piperidin-4-yl}-2H-benzimidazol-2-one,
1,3-dihydro-1-{trans-4-[4-(4-nitrobenzoyl)piperazin-1-yl]-1-cyclohexyl}-2H-benzimidazol-2-one,
1,3-dihydro-1-{trans-4-[1-(3-pyridinecarbonyl)-4-piperidinylamino]-1-cyclohexyl}-2H-benzimidazol-2-one,
5-methyl-1,3-dihydro-1-{1-[1-(3-pyridinecarbonyl)piperidin-4-yl]piperidin-4-yl}-2H-benzimidazol-2-one,
1,3-dihydro-1-{trans-4-[4-(5-pyrimidinecarbonyl)piperazin-1-yl]-1-cyclohexyl}-2H-benzimidazol-2-one,
1,3-dihydro-1-{1-[1-(4-amino-5-pyrimidinecarbonyl)piperidin-4-yl]piperidin-4-yl}-2H-benzimidazol-2-one,
1,3-dihydro-1-{1-[1-(3-pyridinemethyl)piperidin-4-yl]piperidin-4-yl}-2H-benzimidazol-2-one, 1,3-dihydro-1-{1-[1-(6-methoxy-2-pyrazinecarbonyl) piperidin-4-yl]piperidin-4-yl}-2H-benzimidazol-2-one, 5-methyl-1,3-dihydro-1-{1-[1-(5-pyrimidinecarbonyl) piperidin-4-yl]piperidin-4-yl}-2H-benzimidazol-2-one, 5-fluoro-1,3-dihydro-1-{1-[1-(5-pyrimidinecarbonyl) piperidin-4-yl]piperidin-4-yl}-2H-benzimidazol-2-one, 5-chloro-1,3-dihydro-1-{1-[1-(5-pyrimidinecarbonyl) piperidin-4-yl]piperidin-4-yl}-2H-benzimidazol-2-one, 4-fluoro-1,3-dihydro-1-{1-[1-(5-pyrimidinecarbonyl) piperidin-4-yl]piperidin-4-yl}-2H-benzimidazol-2-one, 6-fluoro-1,3-dihydro-1-{1-[1-(5-pyrimidinecarbonyl) piperidin-4-yl]piperidin-4-yl}-2H-benzimidazol-2-one, 7-fluoro-1,3-dihydro-1-{1-[1-(5-pyrimidinecarbonyl) piperidin-4-yl]piperidin-4-yl}-2H-benzimidazol-2-one, 6-methyl-1,3-dihydro-1-{1-[1-(5-pyrimidinecarbonyl) piperidin-4-yl]piperidin-4-yl}-2H-benzimidazol-2-one, 1,3-dihydro-1-{1-[1-(2-amino-5-pyrimidinecarbonyl) piperidin-4-yl]piperidin-4-yl}-2H-benzimidazol-2-one, 1,3-dihydro-1-{1-[1-(5-pyrimidinecarbonyl)piperidin-4-yl] piperidin-4-yl}-2H-benzimidazol-2-one, 1,3-dihydro-1-{1-[1-(6-methylamino-2-pyrazinecarbonyl) piperidin-4-yl]piperidin-4-yl}-2H-benzimidazol-2-one, 1,3-dihydro-1-{1-[1-(6-dimethylamino-2-pyrazinecarbonyl) piperidin-4-yl]piperidin-4-yl}-2H-benzimidazol-2-one, 1,3-dihydro-1-{1-[1-(6-piperidino-2-pyrazinecarbonyl) piperidin-4-yl]piperidin-4-yl}-2H-benzimidazol-2-one, 1,3-dihydro-1-{1-[1-(6-pyrrolidinyl-2-pyrazinecarbonyl) piperidin-4-yl]piperidin-4-yl}-2H-benzimidazol-2-one, 5-methyl-1,3-dihydro-1-{1-[1-(5-pyrimidinemethyl) piperidin-4-yl]piperidin-4-yl}-2H-benzimidazol-2-one, 1,3-dihydro-1-{trans-4-[4-(5-pyridinecarbonylamino) piperidin-1-yl]-1-cyclohexyl}-2H-benzimidazol-2-one, 1,3-dihydro-1-{1-[1-(4-pyridazinecarbonyl)piperidin-4-yl] piperidin-4-yl}-2H-benzimidazol-2-one, 1,3-dihydro-1-{1-[1-(6-benzyloxy-2-pyrazinecarbonyl) piperidin-4-yl]piperidin-4-yl}-2H-benzimidazol-2-one, 1,3-dihydro-1-{1-[1-(6-chloro-2-pyrazinecarbonyl) piperidin-4-yl]piperidin-4-yl}-2H-benzimidazol-2-one, 4-methyl-1,3-dihydro-1-{1-[1-(3-pyridinecarbonyl) piperidin-4-yl]piperidin-4-yl}-2H-benzimidazol-2-one, 5-ethyl-1,3-dihydro-1-{1-[1-(5-pyrimidinecarbonyl) piperidin-4-yl]piperidin-4-yl}-2H-benzimidazol-2-one, 5-methoxy-1,3-dihydro-1-{1-[1-(5-pyrimidinecarbonyl) piperidin-4-yl]piperidin-4-yl}-2H-benzimidazol-2-one, 5-hydroxy-1,3-dihydro-1-{1-[1-(5-pyrimidinecarbonyl) piperidin-4-yl]piperidin-4-yl}-2H-benzimidazol-2-one, 5-ethoxy-1,3-dihydro-1-{1-[1-(5-pyrimidinecarbonyl) piperidin-4-yl]piperidin-4-yl}-2H-benzimidazol-2-one, 5-(2-hydroxyethoxy)-1,3-dihydro-1-{1-[1-(5-pyrimidinecarbonyl)piperidin-4-yl]piperidin-4-yl}-2H-benzimidazol-2-one, 1,3-dihydro-1-{1-[1-(6-amino-2-pyrazinecarbonyl) piperidin-4-yl]piperidin-4-yl}-2H-benzimidazol-2-one, 1,3-dihydro-3-{1-[1-(3-pyridinecarbonyl)piperidin-4-yl] piperidin-4-yl}-2H-2-oxo-imidazo[4,5-b]pyridine, 1,3-dihydro-1-{1-[trans-4-(3-pyridinecarbonylamino) cyclohexyl]piperidin-4-yl}-2H-benzimidazol-2-one, 1,3-dihydro-1-{1-[4-(1,3-dihydro-2-oxo-2H-benzimidazolin-1-yl)cyclohexyl]piperidin-4-yl}-2H-benzimidazol-2-one, 1,3-dihydro-1-{1-[cis-4-(3-pyridinecarbonylamino) cyclohexyl]piperidin-4-yl}-2H-benzimidazol-2-one, 5-propyl-1,3-dihydro-1-{1-[1-(5-pyrimidinecarbonyl) piperidin-4-yl]piperidin-4-yl}-2H-benzimidazol-2-one, 5-butyl-1,3-dihydro-1-{1-[1-(5-pyrimidinecarbonyl) piperidin-4-yl]piperidin-4-yl}-2H-benzimidazol-2-one, 5-(1-methylethyl)-1,3-dihydro-1-{1-[1-(5-pyrimidinecarbonyl)piperidin-4-yl]piperidin-4-yl}-2H-benzimidazol-2-one, 5-(1-hydroxyethyl)-1,3-dihydro-1-{1-[1-(5-pyrimidinecarbonyl)piperidin-4-yl]piperidin-4-yl}-2H-benzimidazol-2-one, 4-methyl-1,3-dihydro-1-{1-[1-(5-pyrimidinecarbonyl) piperidin-4-yl]piperidin-4-yl}-2H-benzimidazol-2-one, 4-ethyl-1,3-dihydro-1-{1-[1-(5-pyrimidinecarbonyl) piperidin-4-yl]piperidin-4-yl}-2H-benzimidazol-2-one, 5,6-dimethyl-1,3-dihydro-1-{1-[1-(5-pyrimidinecarbonyl) piperidin-4-yl]piperidin-4-yl}-2H-benzimidazol-2-one, 4,5-dimethyl-1,3-dihydro-1-{1-[1-(5-pyrimidinecarbonyl) piperidin-4-yl]piperidin-4-yl}-2H-benzimidazol-2-one, 1,3-Dihydro-1-{1-[1-(5-pyrimidinylcarbonyl)piperidin-4-yl]piperidin-4-yl}-1H-3,4-dihydroquinazolin-2-one, (±)-1,3-Dihydro-1-{1-[1-(1-(5-pyrimidinyl)-ethyl) piperidin-4-yl]piperidin-4-yl}-2H-benzimidazol-2-one, (1'''S) 1,3-Dihydro-1-{1'-[1''-(1'''-(5''''-pyrimidinyl)-ethyl) piperidin-4''-yl]piperidin-4'-yl}-2H-benzimidazol-2-one, (1'''R) 1,3-Dihydro-1-{1'-[1''-(1'''-(5''''-pyrimidinyl)-ethyl) piperidin-4''-yl]piperidin-4'-yl}-2H-benzimidazol-2-one, (1'''S) 1,3-Dihydro-1-{1'-[1''-(1'''-(5''''-pyrimidinyl)-ethyl) piperidin-4''-yl]piperidin-4'-yl}-5-chloro-2H-benzimidazol-2-one, (1'''R) 1,3-Dihydro-1-{1'-[1''-(1'''-(5''''-pyrimidinyl)-ethyl)piperidin-4''-yl]piperidin-4'-yl}-5-chloro-2H-benzimidazol-2-one, (1'''S) 1,3-Dihydro-1-{1'-[1''-(1'''-(5''''-pyrimidinyl)-ethyl)piperidin-4''-yl]piperidin-4'-yl}-5-methyl-2H-benzimidazol-2-one, (1'''R) 1,3-Dihydro-1-{1'-[1''-(1'''-(5''''-pyrimidinyl)-ethyl) piperidin-4''-yl]piperidin-4'-yl}-5-methyl-2H-benzimidazol-2-one, 1,3-Dihydro-1-{1-[4-oxocyclohex-1-yl]piperidin-4-yl}-2H-benzimidazol-2-one, cis-1,3-Dihydro-1-{1-[1-(5-pyrimidinylamino)cyclohex-4-yl]piperidin-4-yl}-2H-benzimidazol-2-one, trans-1,3-Dihydro-1-{1-[1-(5-pyrimidinylamino)cyclohex-4-yl]piperidin-4-yl}-2H-benzimidazol-2-one, trans-1,3-Dihydro-1-{4-[4-(3-pyridinylmethyl)piperazin-1-yl]-1-cyclohexyl}-2H-benzimidazol-2-one, 1,3-Dihydro-1-{1-[1-(2-pyrazinylmethyl)piperidin-4-yl] piperidin-4-yl}-2H-benzimidazol-2-one, (±)-cis-1,3-Dihydro-1-(1-{4-[(5-pyrimidinyl) hydroxymethyl]cyclohex-1-yl}piperidin-4-yl)-2H-benzimidazol-2-one, (±)-trans-1,3-Dihydro-1-(1-{4-[(5-pyrimidinyl) hydroxymethyl]cyclohex-1-yl}piperidin-4-yl)-2H-benzimidazol-2-one, trans-1,3-Dihydro-1-{1-[4-(5-pyrimidinylcarbonyl) cyclohex-1-yl]piperidin-4-yl}-2H-benzimidazol-2-one, cis-1,3-Dihydro-1-{1-[1-(3-pyridylamino)cyclohex-4-yl] piperidin-4-yl}-2H-benzimidazol-2-one, trans-1,3-Dihydro-1-{1-[1-(3-pyridylamino)cyclohex-4-yl] piperidin-4-yl}-2H-benzimidazol-2-one, (±)-1,3-Dihydro-1-(1-{1-[1-(2-pyrazinyl)-ethyl]piperidin-4-yl}piperidin-4-yl)-2H-benzimidazol-2-one, (±) 1,3-Dihydro-1-{1'-[1''-(1'''-(5''''-pyridinyl)-ethyl) piperidin-4''-yl]piperidin-4'-yl}-2H-benzimidazol-2-one, (1'''R) 1,3-Dihydro-1-{1'-[1''-(1'''-(5''''-pyridinyl)-ethyl) piperidin-4''-yl]piperidin-4'-yl}-2H-benzimidazol-2-one, (1'''R) 1,3-Dihydro-1-{1'-[1''-(1'''-(5''''-pyridinyl)-ethyl) piperidin-4''-yl]piperidin-4'-yl}-5-chloro-2H-benzimidazol-2-one, (1'''R) 1,3-Dihydro-1-{1'-[1''-(1'''-(5''''-pyridinyl)-ethyl) piperidin-4''-yl]piperidin-4'-yl}-5-methyl-2H-benzimidazol-2-one, (±)-1,3-Dihydro-1-(1-{1-[1-(2-pyrazinyl)-1-ethyl]piperidin-4-yl}piperidin-4-yl)-5-methyl-2H-benzimidazol-2-one, (±)-1,3-Dihydro-1-(1-{1-[1-(2-pyrazinyl)-1-ethyl]piperidin-4-yl}piperidin-4-yl)-5-chloro-2H-benzimidazol-2-one, 1,3-dihydro-1-(1-{1-[2-(5-pyrimidinyl)-prop-2-yl]piperidin-4-yl}piperidin-4-yl)-2H-benzimidazol-2-one, 1,3-dihydro-1-(1-{1-[2-(5-pyrimidinyl)-prop-2-yl]piperidin-4-yl}piperidin-4yl)-5-methyl-2H-benzimidazol-2-one, 1,3-dihydro-1-(1-{1-[2-(5-pyrimidinyl)-prop-2-yl]piperidin-4-yl}piperidin-4yl)-5-chloro-2H-benzimidazol-2-one, 1,3-dihydro-5-methyl-1-(1-{1-[2-(3-pyridyl)-prop-2-yl]piperidin-4-yl}piperidin-4-yl)-2H-benzimidazol-2-one, 1,3-dihydro-(1-{1-[2-(3-pyridyl)-prop-2-yl]piperidin-4-yl}piperidin-4-yl)-2H-benzimidazol-2-one, 1,3-dihydro-1-{1-[1-(2-phenyl-5-pyrimidinylcarbonyl)piperidin-4-yl]piperidin-4-yl}-2H-benzimidazol-2-one, 1,3-Dihydro-1-{1-[1-(3-pyridinesulfonyl)piperidin-4-yl]piperidin-4-yl}-2H-benzimidazol-2-one, 1,3-dihydro-1-{1-[1-(2-methyl-5-pyrimidinylcarbonyl)piperidin-4-yl]piperidin-4-yl}-2H-benzimidazol-2-one, 1,3-Dihydro-1-{1-[1-(5-pyrimidinylmethyl)piperidin-4-yl]piperidin-4-yl}-2H-benzimidazol-2-one, 1,3-Dihydro-1-{1-[1-(4-imidazolylmethyl)piperidin-4-yl]piperidin-4-yl}-2H-benzimidazol-2-one, 1,3-dihydro-1-{1-[1-(2-amino-5-pyrimidinylcarbonyl)piperidin-4-yl]piperidin-4-yl}-2H-benzimidazol-2-one, (1'''R)-1,3-Dihydro-1-{1'-[1''-(1'''-phenylethyl)piperidin-4''-yl]piperidin-4'-yl}-2H-benzimidazol-2-one, (1'''S)-1,3-Dihydro-1-{1'-[1''-(1'''-phenylethyl)piperidin-4''-yl]piperidin-4'-yl}-2H-benzimidazol-2-one, (1'''R)-1,3-Dihydro-1-{1'-[1''-(2'''-hydroxy-1'''-phenylethyl)piperidin-4''-yl]piperidin-4'-yl}-2H-benzimidazol-2-one, (1'''S)-1,3-Dihydro-1-{1'-[1''-(2'''-hydroxy-1'''-phenylethyl)piperidin-4''-yl]piperidin-4'-yl}-2H-benzimidazol-2-one, trans-1,3-Dihydro-1-{1-[4-hydroxycyclohex-1-yl]piperidin-4-yl}-2H-benzimidazol-2-one, or cis-1,3-Dihydro-1-{1-[4-hydroxycyclohex-1-yl]piperidin-4-yl}-2H-benzimidazol-2-one.

4. The compound of claim 3 which is 5-methyl-1,3-dihydro-1-{1-[1-(3-pyridinecarbonyl)piperidin-4-yl]piperidin-4-yl}-2H-benzimidazol-2-one, 1,3-dihydro-1-{1-[1-(5-pyrimidinecarbonyl)piperidin-4-yl]piperidin-4-yl}-2H-benzimidazol-2-one, 1,3-dihydro-1-{1-[1-(2-pyrazinecarbonyl)piperidin-4-yl]piperidin-4-yl}-2H-benzimidazol-2-one, 1,3-dihydro-1-{1-[1-(3-pyridinemethyl)piperidin-4-yl]piperidin-4-yl}-2H-benzimidazol-2-one, 5-methoxy-1,3-dihydro-1-{1-[1-(5-pyrimidinecarbonyl)piperidin-4-yl]piperidin-4-yl}-2H-benzimidazol-2-one, 5-methyl-1,3-dihydro-1-{1-[1-(5-pyrimidinecarbonyl)piperidin-4-yl]piperidin-4-yl}-2H-benzimidazol-2-one, 5-ethyl-1,3-dihydro-1-{1-[1-(5-pyrimidinecarbonyl)piperidin-4-yl]piperidin-4-yl}-2H-benzimidazol-2-one, (1'''R) 1,3-Dihydro-1-{1'-[1''-(1'''-(5''''-pyrimidinyl)-ethyl)piperidin-4''-yl]piperidin-4'-yl}-2H-benzimidazol-2-one, (1'''R) 1,3-Dihydro-1-{1'-[1''-(1'''-(5''''-pyrimidinyl)-ethyl)piperidin-4''-yl]piperidin-4'-yl}-5-chloro-2H-benzimidazol-2-one, (1'''R) 1,3-Dihydro-1-{1'-[1''-(1'''-(5''''-pyrimidinyl)-ethyl)piperidin-4''-yl]piperidin-4'-yl}-5-methyl-2H-benzimidazol-2-one, 1,3-Dihydro-1-{1-[4-oxocyclohex-1-yl]piperidin-4-yl}-2H-benzimidazol-2-one, trans-1,3-Dihydro-1-{1-[1-(5-pyrimidinylamino)cyclohex-4-yl]piperidin-4-yl}-2H-benzimidazol-2-one, trans-1,3-Dihydro-1-{1-[1-(3-pyridylamino)cyclohex-4-yl]piperidin-4-yl}-2H-benzimidazol-2-one, (1'''R) 1,3-Dihydro-1-{1'-[1''-(1'''-(5''''-pyridinyl)-ethyl)piperidin-4''-yl]piperidin-4'-yl}-2H-benzimidazol-2-one, (1'''R) 1,3-Dihydro-1-{1'-[1''-(1'''-(5''''-pyridinyl)-ethyl)piperidin-4''-yl]piperidin-4'-yl}-5-chloro-2H-benzimidazol-2-one, or (1'''R) 1,3-Dihydro-1-{1'-[1''-(1'''-(5''''-pyridinyl)-ethyl)piperidin-4''-yl]piperidin-4'-yl}-5-methyl-2H-benzimidazol-2-one.

5. A method for the treatment or prevention of abnormal increase in eye axial length in an animal in need thereof, which comprises the step of ocularly administering to said animal a pharmacologically effective amount of a muscarinic pharmacological agent known to be selective for m1, m2 and m4 receptors, but less active at m3 receptors.

6. A method for the treatment or prevention of abnormal increase in eye axial length in an animal in need thereof, which comprises the step of ocularly administering to said animal a pharmacologically effective amount of a muscarinic pharmacological agent of claim 1, known to be selective for m1, m2 and m4 receptors, but less active at m3 receptors.

7. A method of alleviating or controlling the development of amblyopia in the eye of an animal in need thereof, which comprises administering to such an animal a pharmacologically effective amount of a compound of claim 1.

8. A composition useful for the treatment or prevention of abnormal increase in eye axial length in an animal in need thereof, which comprises a pharmacologically effective amount of a muscarinic pharmacological agent, known to be selective for m1, m2 and m4 receptors, but less active at m3 receptors, in a carrier or diluent buffered to a pH suitable for ocular administration.

9. A composition useful for the treatment or prevention of abnormal increase in eye axial length in an animal in need thereof, which comprises a pharmacologically effective amount of a muscarinic pharmacological agent of claim 1, known to be selective for m1, m2 and m4 receptors, but less active at m3 receptors, in a carrier or diluent buffered to a pH suitable for ocular administration.

* * * * *